United States Patent
Suo et al.

(10) Patent No.: US 10,000,521 B2
(45) Date of Patent: *Jun. 19, 2018

(54) SUBSTITUTED GEMCITABINE BICYCLIC AMIDE ANALOGS AND TREATMENT METHODS USING SAME

(71) Applicant: Nucorion Pharmaceuticals, Inc., Wilmington, DE (US)

(72) Inventors: Zucai Suo, Dublin, OH (US); Vinod P. Vyavhare, Columbus, OH (US); David J. Taggart, Columbus, OH (US)

(73) Assignee: Nucorion Pharmaceuticals, Inc., Wilmington, DE (US)

( * ) Notice: Subject to any disclaimer, the term of this patent is extended or adjusted under 35 U.S.C. 154(b) by 88 days.

This patent is subject to a terminal disclaimer.

(21) Appl. No.: 14/783,199

(22) PCT Filed: Mar. 15, 2014

(86) PCT No.: PCT/US2014/029929
§ 371 (c)(1),
(2) Date: Oct. 8, 2015

(87) PCT Pub. No.: WO2014/145207
PCT Pub. Date: Sep. 18, 2014

(65) Prior Publication Data
US 2016/0052952 A1    Feb. 25, 2016

Related U.S. Application Data

(60) Provisional application No. 61/786,501, filed on Mar. 15, 2013.

(51) Int. Cl.
| | |
|---|---|
| A61K 31/70 | (2006.01) |
| A01N 43/04 | (2006.01) |
| C07H 19/00 | (2006.01) |
| C12N 5/00 | (2006.01) |
| C12N 5/02 | (2006.01) |
| C07H 19/06 | (2006.01) |
| A61K 31/7052 | (2006.01) |
| A61K 31/7068 | (2006.01) |

(52) U.S. Cl.
CPC ......... C07H 19/06 (2013.01); A61K 31/7052 (2013.01); A61K 31/7068 (2013.01)

(58) Field of Classification Search
CPC ....................... A61K 31/7068; A61K 31/7052
See application file for complete search history.

(56) References Cited

U.S. PATENT DOCUMENTS 4,966,891 A    10/1990   Fujiu 8,741,858 B2 *   6/2014   Ren .................. A61K 47/48215
                                                                  514/42
9,447,137 B2    9/2016   Suo
2010/0286084 A1   11/2010   Ren

FOREIGN PATENT DOCUMENTS

| EP | 2423215 A1 | 2/2012 |
|---|---|---|
| EP | 2615101 A1 | 7/2013 |
| WO | WO 2012/031539 | 3/2012 |
| WO | WO 2016/138026 | 9/2016 |

OTHER PUBLICATIONS

National Center for Biotechnology Information. PubChem Compound Database; CID=53839260, https://pubchem.ncbi.nlm.nih.gov/compound/53839260 (accessed Oct. 7, 2015).
Written Opinion of the International Searching Authority issued in PCT/US2014/29929, dated Jul. 2, 2014.
Kroep, J. R., et al. Pretreatment Deoxycytidine Kinase Levels Predict in Vivo Gemcitabine Sensitivity, Mol. Cancer Ther. 1, 371-376 (2002).
Saiki, T., et al. DCK is frequently inactivated in acquired gemcitabine-resistant human cancer cells, Biochim. Biophys. Res. Commun. 421, 98-104 (2012).
Zhao, C., et al., Synthesis and Biological Evaluation of Oral Prodrugs Based on the Structure of Gemicitabine, Chemical Biology & Drug Design, 80(3):479-488 (2012).

* cited by examiner

*Primary Examiner* — Lawrence E Crane
(74) *Attorney, Agent, or Firm* — Knobbe, Martens, Olson & Bear, LLP

(57) ABSTRACT

In one aspect, the invention relates to substituted gemcitabine aryl amide analogs, derivatives thereof, and related compounds; synthesis methods for making the compounds; pharmaceutical compositions comprising the compounds; and methods of treating viral disorders and disorders of uncontrolled cellular proliferation using the compounds and compositions. In certain aspects, the compounds have the following structure:

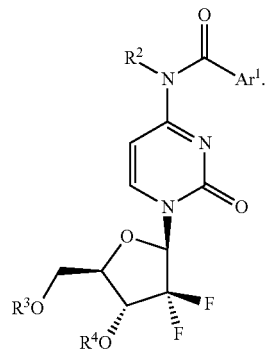

16 Claims, 7 Drawing Sheets

SUBSTITUTED GEMCITABINE BICYCLIC AMIDE ANALOGS AND TREATMENT METHODS USING SAME

CROSS-REFERENCE TO RELATED APPLICATIONS

This Application is the U.S. National Phase of Application No. PCT/US2014/029929 entitled "SUBSTITUTED GEMCITABINE BICYCLIC AMIDE ANALOGS AND TREATMENT METHODS USING SAME" filed Mar. 15, 2014 and published in English on Sep. 18, 2014 as WO 2014/145207 which claims the benefit of U.S. Provisional Application No. 61/786,501, filed on Mar. 15, 2013, which is incorporated herein by reference in its entirety.

BACKGROUND

An estimated 170 million people throughout the world are infected with the hepatitis C virus (HCV). More than 70% of these individuals remain chronically infected for life, of which 15-20% eventually develops liver cirrhosis and hepatocellular carcinoma. The current therapy for HCV infections is the combination of ribavirin and interferon-α (IFN-α), as well as a limited number of protease inhibitors (e.g. telaprevir or boceprevir). Unfortunately, in addition to severe side effects, the sustained response rate of this therapy is no better than about 80% and it is genotype-dependent.

More recently, a new nucleotide analog drug, sofosbuvir (isopropyl (2S)-2-[[[(2R,3R,4R,5R)-5-(2,4-dioxopyrimidin-1-yl)-4-fluoro-3-hydroxy-4-methyl-tetrahydrofuran-2-yl]methoxy-phenoxy-phosphoryl]amino]propanoate; brand name Sovaldi®) has been approved as the first all-oral, interferon-free treatment for treating chronic HCV infections. Sofosbuvir inhibits NS5B, the virus-encoded RNA-dependent RNA polymerase that replicates the RNA genome of HCV. In 2013, the FDA approved sofosbuvir in combination with ribavirin for oral dual therapy of HCV genotypes 2 and 3, as well as for triple therapy with injected pegylated interferon-α (pegIFN) and ribavirin for treatment-naive patients with HCV genotypes 1 and 4. Although, the clinical responses seen with sofosbuvir, alone and in combination therapy, are encouraging, further research is required to provide further options in the clinical arsenal to combat the widespread infections of HCV.

Accordingly, new and improved HCV treatments remain urgently needed to combat the widespread infections of HCV, including more selective and potent drugs with improved toxicity profiles that can be used alone or as part of combination therapy regimens. This need and other needs are addressed by the present invention.

SUMMARY

In accordance with the purpose(s) of the invention, as embodied and broadly described herein, the invention, in one aspect, relates to substituted gemcitabine aryl amide analogs, methods of making same, pharmaceutical compositions comprising same, and methods of treating viral disorders and disorders of uncontrolled cellular proliferation using same.

Disclosed are compounds having a structure represented by a formula:

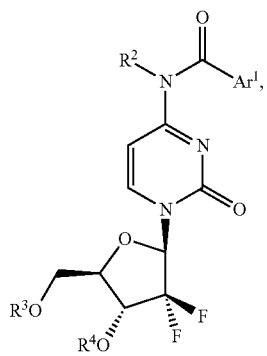

wherein $Ar^1$ is a bicyclic fused ring system comprising an aryl ring fused to a 5-, 6-, or 7-membered heterocycloalkyl; wherein the aryl ring is selected from phenyl, pyridinyl, pyrimidinyl, pyridazinyl, pyrazinyl, and triazinyl; wherein the aryl ring is substituted with 0, 1, 2, or 3 groups independently selected from halogen, —OH, —CN, —NH$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$; wherein each R$^5$ is independently selected from hydrogen, C1-C8 alkyl, and a hydroxyl protecting group; wherein each of R$^{6a}$ and R$^{6b}$ is independently selected from hydrogen, C1-C4 alkyl, and an amine protecting group; wherein R$^2$ is selected from hydrogen, C1-C4 alkyl, and an amine protecting group; wherein R$^3$ is selected from hydrogen and a hydroxyl protecting group; and wherein R$^4$ is selected from hydrogen, C1-C8 alkyl, and a hydroxyl protecting group, or wherein R$^3$ and R$^4$ together comprise a divalent moiety having a structure represented by a formula:

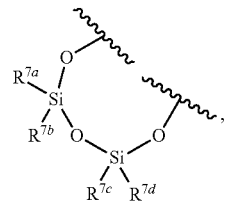

wherein each of $R^{7a}$, $R^{7b}$, $R^{7c}$, and $R^{7d}$ is independently selected from methyl, ethyl, propyl, and butyl; or a pharmaceutically acceptable salt, solvate, or polymorph thereof.

Also disclosed are compounds having a structure represented by a formula:

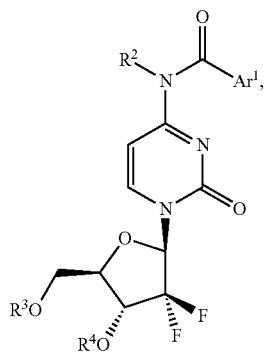

wherein Ar¹ is a bicyclic fused ring system comprising an aryl ring fused to a 5-, 6-, or 7-membered heterocycloalkyl; wherein the aryl ring is selected from phenyl, pyridinyl, pyrimidinyl, pyridazinyl, pyrazinyl, and triazinyl; wherein the aryl ring is substituted with 0, 1, 2, or 3 groups independently selected from halogen, —OH, —CN, —NH₂, —NO₂, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl is substituted with 0, 1, 2, 3, 4, or 5 groups independently selected from halogen, —OH, —CN, —NH₂, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR⁵, and —(C=O)NR⁶ᵃR⁶ᵇ; wherein each R⁵ is independently selected from hydrogen, C1-C8 alkyl, and a hydroxyl protecting group; wherein each of R⁶ᵃ and R⁶ᵇ is independently selected from hydrogen, C1-C4 alkyl, and an amine protecting group; wherein R² is selected from hydrogen, C1-C4 alkyl, and an amine protecting group; wherein R³ is selected from hydrogen and a hydroxyl protecting group; and wherein R⁴ is selected from hydrogen, C1-C8 alkyl, and a hydroxyl protecting group, or wherein R³ and R⁴ together comprise a divalent moiety having a structure represented by a formula:

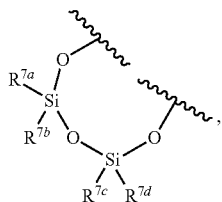

wherein each of R⁷ᵃ, R⁷ᵇ, R⁷ᶜ, and R⁷ᵈ is independently selected from methyl, ethyl, propyl, and butyl; or a pharmaceutically acceptable salt, solvate, or polymorph thereof.

Also disclosed are methods for making a compound comprising the steps of: (a) providing a first compound having a structure represented by a formula:

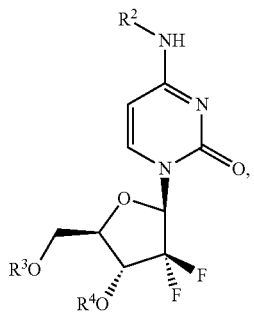

wherein R² is selected from hydrogen, C1-C4 alkyl, and amine protecting group; wherein R³ is selected from hydrogen and hydroxyl protecting group; and wherein R⁴ is selected from hydrogen, C1-C8 alkyl, and hydroxyl protecting group, or wherein R³ and R⁴ together comprise a divalent moiety having a structure represented by a formula:

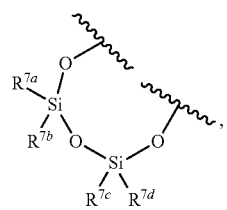

wherein each of R⁷ᵃ, R⁷ᵇ, R⁷ᶜ, and R⁷ᵈ is independently selected from methyl, ethyl, propyl, and butyl; and (b) reacting with a second compound having a structure represented by a formula:

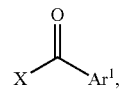

wherein X is halogen or pseudohalogen; wherein Ar¹ is a bicyclic fused ring system comprising an aryl ring fused to a 5-, 6-, or 7-membered heterocycloalkyl; wherein the aryl ring is selected from phenyl, pyridinyl, pyrimidinyl, pyridazinyl, pyrazinyl, and triazinyl; wherein the aryl ring is substituted with 0, 1, 2, or 3 groups independently selected from halogen, —OH, —CN, —NH₂, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl is substituted with 0, 1, 2, 3, 4, or 5 groups independently selected from halogen, —OH, —CN, —NH₂, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR⁵, and —(C=O)NR⁶ᵃR⁶ᵇ; wherein each R⁵ is independently selected from hydrogen, C1-C8 alkyl, and a hydroxyl protecting group; wherein each of R⁶ᵃ and R⁶ᵇ is independently selected from hydrogen, C1-C4 alkyl, and an amine protecting group; thereby forming an amide bond.

Also disclosed are methods for making a compound comprising the steps of: (a) providing a first compound having a structure represented by a formula:

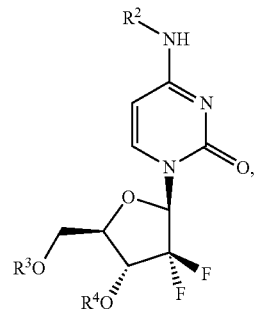

wherein R² is selected from hydrogen, C1-C4 alkyl, and amine protecting group; wherein R³ is selected from hydrogen and hydroxyl protecting group; and wherein R⁴ is selected from hydrogen, C1-C8 alkyl, and hydroxyl protecting group, or wherein R³ and R⁴ together comprise a divalent moiety having a structure represented by a formula:

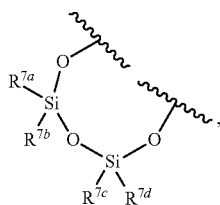

wherein each of $R^{7a}$, $R^{7b}$, $R^{7c}$, and $R^{7d}$ is independently selected from methyl, ethyl, propyl, and butyl; and (b) reacting with a second compound having a structure represented by a formula:

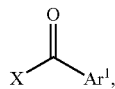

wherein X is halogen or pseudohalogen; wherein $Ar^1$ is a bicyclic fused ring system comprising an aryl ring fused to a 5-, 6-, or 7-membered heterocycloalkyl; wherein the aryl ring is selected from phenyl, pyridinyl, pyrimidinyl, pyridazinyl, pyrazinyl, and triazinyl; wherein the aryl ring is substituted with 0, 1, 2, or 3 groups independently selected from halogen, —OH, —CN, —NH$_2$, —NO$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O) OR$^5$, and —(C=O)NR$^{6a}$R$^{6b}$; wherein each R$^5$ is independently selected from hydrogen, C1-C8 alkyl, and a hydroxyl protecting group; wherein each of R$^{6a}$ and R$^{6b}$ is independently selected from hydrogen, C1-C4 alkyl, and an amine protecting group; thereby forming an amide bond.

Also disclosed are products of the disclosed methods.

Also disclosed are pharmaceutical compositions comprising a pharmaceutically acceptable carrier and an effective amount of a disclosed compound or the product of a disclosed method.

Also disclosed are kits comprising a disclosed compound or the product of a disclosed method or a disclosed pharmaceutical composition and one or more of: (a) an antiviral agent; (b) a substance known to increase risk of viral infection; (c) instructions for treating a viral infection; (d) a drug known to treat a disorder of uncontrolled cellular proliferation; (e) a substance known to increase risk of uncontrolled cellular proliferation; and (f) instructions for treating a disorder of uncontrolled cellular proliferation.

Also disclosed are methods for treating a subject for viral infection, the method comprising the step of administering to the subject an effective amount of a disclosed compound or the product of a disclosed method or a disclosed pharmaceutical composition.

Also disclosed are methods for inhibiting viral replication within at least one cell, the method comprising the step of administering to the cell an effective amount of a disclosed compound or a product of a disclosed method or a disclosed pharmaceutical composition.

Also disclosed are methods for treating a disorder of uncontrolled cellular proliferation, the method comprising administering to a subject an effective amount of a disclosed compound or a disclosed product or a disclosed pharmaceutical composition.

Also disclosed are methods for arresting tumor growth, the method comprising administering to at least one tumor cell an effective amount of a disclosed compound or a product of a disclosed method or a disclosed pharmaceutical composition.

Also disclosed are uses of a disclosed compound, a disclosed product of making, or a pharmaceutically acceptable salt, hydrate, solvate, or polymorph thereof.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
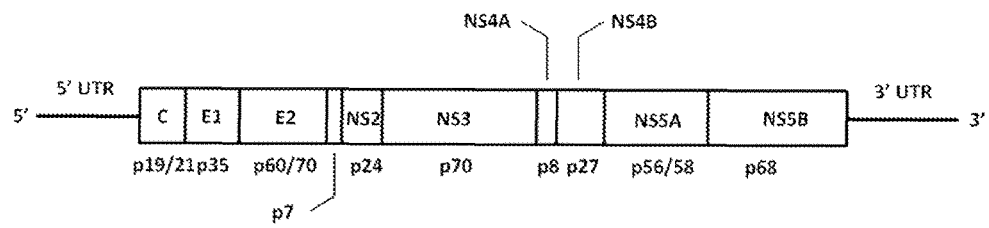
FIG. 1 shows a schematic representation of the HCV genome showing the open reading frames of the capsid (C), envelope proteins (E1 and E2), membrane protein p7 and non-structural proteins NS2, NS3, NS4A, NS4B, NS5A and NS5B. The protein products are shown below the genome schematic (p19/21, p 35, p60/70, p7, etc.).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment prior to the administering step. In further aspects, the disclosed methods further comprise the step of identifying a subject in need of treatment for the disorder. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor, or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay.

As used herein, "$TC_{50}$," is intended to refer to toxic concentration of a substance (e.g., a compound or a drug) for 50% of the population. For example, $TC_{50}$ can refer to the half maximal (50%) toxicity concentration (TC) of a substance as determined in a suitable assay, for example, an assay disclosed herein.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

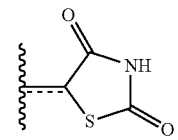

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $(CH_2)_a$, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or $OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide" as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl" as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, $S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent.

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$, $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)$O-N(R^\circ)_2$; or $-(C_{1-4}$ straight or branched)alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

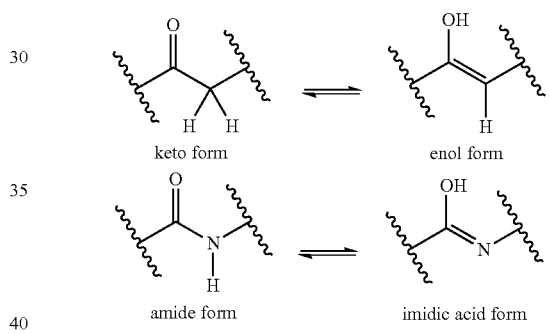

keto form      enol form amide form      imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

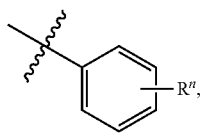

which is understood to be equivalent to a formula:

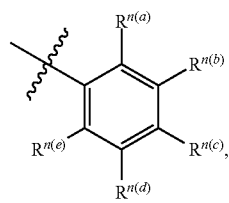

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to gemcitabine amide analog compounds. More specifically, in one aspect, the present invention relates to compounds useful for treatment of cancers or hepatitis.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In various aspects, "optionally substituted" refers to substitution with 0-3 groups independently selected from fluoro, chloro, bromo, iodo, methyl, methoxy, fluoromethyl, fluoromethoxy, difluoromethyl, difluoromethoxy, trifluoromethyl, trifluoromethoxy, ethyl, ethoxy, propyl, butyl, cyano, hydroxy, thiol, alkylthiol, acetamide, optionally substituted aryl, optionally substituted heteroaryl, phenoxy, nitro, —$NH_2$, amino, monoalkylamino, dialkylamino, acetyl, acetoxy, carboxy, alkyl carboxy, and sulfamido; wherein valence is satisfied.

1. Structure

In one aspect, the invention relates to a compound having a structure represented by a formula:

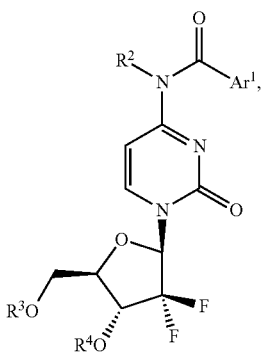

wherein Ar¹ is a bicyclic fused ring system comprising an aryl ring fused to a 5-, 6-, or 7-membered heterocycloalkyl; wherein the aryl ring is selected from phenyl, pyridinyl, pyrimidinyl, pyridazinyl, pyrazinyl, and triazinyl; wherein the aryl ring is substituted with 0, 1, 2, or 3 groups independently selected from halogen, —OH, —CN, —NH$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$; wherein each R$^5$ is independently selected from hydrogen, C1-C8 alkyl, and a hydroxyl protecting group; wherein each of R$^{6a}$ and R$^{6b}$ is independently selected from hydrogen, C1-C4 alkyl, and an amine protecting group; wherein R$^2$ is selected from hydrogen, C1-C4 alkyl, and an amine protecting group; wherein R$^3$ is selected from hydrogen and a hydroxyl protecting group; and wherein R$^4$ is selected from hydrogen, C1-C8 alkyl, and a hydroxyl protecting group, or wherein R$^3$ and R$^4$ together comprise a divalent moiety having a structure represented by a formula:

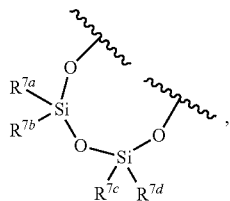

wherein each of R$^{7a}$, R$^{7b}$, R$^{7c}$, and R$^{7d}$ is independently selected from methyl, ethyl, propyl, and butyl; or a pharmaceutically acceptable salt, solvate, or polymorph thereof.

Also disclosed are compounds having a structure represented by a formula:

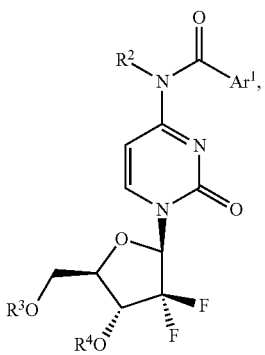

wherein Ar¹ is a bicyclic fused ring system comprising an aryl ring fused to a 5-, 6-, or 7-membered heterocycloalkyl; wherein the aryl ring is selected from phenyl, pyridinyl, pyrimidinyl, pyridazinyl, pyrazinyl, and triazinyl; wherein the aryl ring is substituted with 0, 1, 2, or 3 groups independently selected from halogen, —OH, —CN, —NH$_2$, —NO$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$; wherein each R$^5$ is independently selected from hydrogen, C1-C8 alkyl, and a hydroxyl protecting group; wherein each of R$^{6a}$ and R$^{6b}$ is independently selected from hydrogen, C1-C4 alkyl, and an amine protecting group; wherein R$^2$ is selected from hydrogen, C1-C4 alkyl, and an amine protecting group; wherein R$^3$ is selected from hydrogen and a hydroxyl protecting group; and wherein R$^4$ is selected from hydrogen, C1-C8 alkyl, and a hydroxyl protecting group, or wherein R$^3$ and R$^4$ together comprise a divalent moiety having a structure represented by a formula:

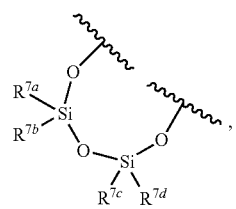

wherein each of R$^{7a}$, R$^{7b}$, R$^{7c}$, and R$^{7d}$ is independently selected from methyl, ethyl, propyl, and butyl; or a pharmaceutically acceptable salt, solvate, or polymorph thereof.

In various aspects, the invention can include the following substituent groups.

a. Ar¹ Groups

In one aspect, Ar¹ is a bicyclic fused ring system comprising an aryl ring fused to a 5-, 6-, or 7-membered heterocycloalkyl; wherein the aryl ring is selected from phenyl, pyridinyl, pyrimidinyl, pyridazinyl, pyrazinyl, and triazinyl; wherein the aryl ring is substituted with 0, 1, 2, or 3 groups independently selected from halogen, —OH, —CN, —NH$_2$, C1-C6 alkyl, C1-C6 alkoxy, C1-C6 monohaloalkyl, C1-C6 polyhaloalkyl, C1-C6 alkylamino, and C1-C6 dialkylamino; and wherein the heterocycloalkyl is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$;

In a further aspect, Ar¹ is a bicyclic fused ring system comprising a phenyl ring fused to a 5-, 6-, or 7-membered heterocycloalkyl. In a still further aspect, Ar¹ is a bicyclic fused ring system comprising a phenyl ring fused to a 5-membered heterocycloalkyl. In a yet further aspect, Ar¹ is a bicyclic fused ring system comprising a phenyl ring fused to a 6-membered heterocycloalkyl. In an even further aspect, Ar¹ is a bicyclic fused ring system comprising a phenyl ring fused to a 7-membered heterocycloalkyl.

In a further aspect, Ar¹ is a bicyclic fused ring system comprising a pyridinyl ring fused to a 5-, 6-, or 7-membered heterocycloalkyl. In a still further aspect, Ar¹ is a bicyclic fused ring system comprising a pyridinyl ring fused to a 5-membered heterocycloalkyl. In a yet further aspect, Ar¹ is a bicyclic fused ring system comprising a pyridinyl ring fused to a 6-membered heterocycloalkyl. In an even further aspect, Ar¹ is a bicyclic fused ring system comprising a pyridinyl ring fused to a 7-membered heterocycloalkyl.

In a further aspect, Ar¹ is a bicyclic fused ring system comprising a pyrimidinyl ring fused to a 5-, 6-, or 7-membered heterocycloalkyl. In a still further aspect, Ar¹ is a bicyclic fused ring system comprising a pyrimidinyl ring fused to a 5-membered heterocycloalkyl. In a yet further aspect, Ar¹ is a bicyclic fused ring system comprising a pyrimidinyl ring fused to a 6-membered heterocycloalkyl. In an even further aspect, Ar¹ is a bicyclic fused ring system comprising a pyrimidinyl ring fused to a 7-membered heterocycloalkyl.

In a further aspect, Ar¹ is a bicyclic fused ring system comprising a pyridazinyl ring fused to a 5-, 6-, or 7-membered heterocycloalkyl. In a still further aspect, Ar¹ is a bicyclic fused ring system comprising a pyridazinyl ring fused to a 5-membered heterocycloalkyl. In a yet further aspect, Ar¹ is a bicyclic fused ring system comprising a pyridazinyl ring fused to a 6-membered heterocycloalkyl. In an even further aspect, Ar¹ is a bicyclic fused ring system comprising a pyridazinyl ring fused to a 7-membered heterocycloalkyl.

In a further aspect, Ar¹ is a bicyclic fused ring system comprising a pyrazinyl ring fused to a 5-, 6-, or 7-membered heterocycloalkyl. In a still further aspect, Ar¹ is a bicyclic fused ring system comprising a pyrazinyl ring fused to a 5-membered heterocycloalkyl. In a yet further aspect, Ar¹ is a bicyclic fused ring system comprising a pyrazinyl ring fused to a 6-membered heterocycloalkyl. In an even further aspect, Ar¹ is a bicyclic fused ring system comprising a pyrazinyl ring fused to a 7-membered heterocycloalkyl.

In a further aspect, Ar¹ is a bicyclic fused ring system comprising a triazinyl ring fused to a 5-, 6-, or 7-membered heterocycloalkyl. In a still further aspect, Ar¹ is a bicyclic fused ring system comprising a triazinyl ring fused to a 5-membered heterocycloalkyl. In a yet further aspect, Ar¹ is a bicyclic fused ring system comprising a triazinyl ring fused to a 6-membered heterocycloalkyl. In an even further aspect, Ar¹ is a bicyclic fused ring system comprising a triazinyl ring fused to a 7-membered heterocycloalkyl.

In various further aspects, Ar¹ is selected from tetrahydronaphthalenyl, chromanyl, dihydrobenzodioxinyl, dihydrobenzooxazinyl, tetrahydroquinoxalinyl, benzodioxinyl, dihydrobenzooxathiinyl, dihydrodioxinopyridinyl, dihydrobenzooxazinyl, tetrahydroquinolinyl, and tetrahydroquinoxalinyl. In a still further aspect, Ar¹ is selected from dihydroindenyl, dihydrobenzofuranyl, benzodioxolyl, benzooxathiolyl, dihydrobenzoxazolyl, and dioxolopyridinyl. In a yet further aspect, Ar¹ is selected from tetrahydrobenzoannulenyl, tetrahydrobenzooxepinyl, and dihydrobenzodioxepinyl.

In a further aspect, the aryl ring of Ar¹ is unsubstituted.

In a further aspect, the aryl ring of Ar¹ is substituted with 0, 1, 2, or 3 groups independently selected from —F, —Cl, —CN, —NH₂, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, and —N(CH₃)CH(CH₃)₂. In a still further aspect, the aryl ring of Ar¹ is substituted with 0, 1, 2, or 3 groups independently selected from —F, —Cl, —CN, —NH₂, methyl, —CH₂F, —CH₂Cl, —CHF₂, —CF₃, —CHCl₂, —CCl₃, —OCH₃, —NHCH₃, and —N(CH₃)₂. In a yet further aspect, the aryl ring of Ar¹ is substituted with 0, 1, 2, or 3 groups independently selected from —F, —CN, —NH₂, methyl, —CH₂F, —CHF₂, —CF₃, —OCH₃, —NHCH₃, and —N(CH₃)₂.

In a further aspect, the aryl ring of Ar¹ is substituted with 0, 1, or 2 groups independently selected from halogen, —OH, —CN, —NH₂, C1-C6 alkyl, C1-C6 alkoxy, C1-C6 monohaloalkyl, C1-C6 polyhaloalkyl, C1-C6 alkylamino, and C1-C6 dialkylamino. In a still further aspect, the aryl ring of Ar¹ is substituted with 0, 1, or 2 groups independently selected from —F, —Cl, —CN, —NH₂, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, and —N(CH₃)CH(CH₃)₂. In a yet further aspect, the aryl ring of Ar¹ is substituted with 0, 1, or 2 groups independently selected from —F, —Cl, —CN, —NH₂, methyl, —CH₂F, —CH₂Cl, —CHF₂, —CF₃, —CHCl₂, —CCl₃, —OCH₃, —NHCH₃, and —N(CH₃)₂. In an even further aspect, the aryl ring of Ar¹ is substituted with 0, 1, or 2 groups independently selected from —F, —CN, —NH₂, methyl, —CH₂F, —CHF₂, —CF₃, —OCH₃, —NHCH₃, and —N(CH₃)₂.

In a further aspect, the aryl ring of Ar¹ is substituted with 0 or 1 group selected from halogen, —OH, —CN, —NH₂, C1-C6 alkyl, C1-C6 alkoxy, C1-C6 monohaloalkyl, C1-C6 polyhaloalkyl, C1-C6 alkylamino, and C1-C6 dialkylamino. In a still further aspect, the aryl ring of Ar¹ is substituted with 0 or 1 group selected from —F, —Cl, —CN, —NH₂, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, and —N(CH₃)CH(CH₃)₂. In a yet further aspect, the aryl ring of Ar¹ is substituted with 0 or 1 group selected from —F, —Cl, —CN, —NH₂, methyl, —CH₂F, —CH₂Cl, —CHF₂, —CF₃, —CHCl₂, —CCl₃, —OCH₃, —NHCH₃, and —N(CH₃)₂. In an even further aspect, the aryl ring of Ar¹ is substituted with 0 or 1 group selected from —F, —CN, —NH₂, methyl, —CH₂F, —CHF₂, —CF₃, —OCH₃, —NHCH₃, and —N(CH₃)₂.

In a further aspect, the aryl ring of Ar¹ is monosubstituted with a group selected from halogen, —OH, —CN, —NH₂, C1-C6 alkyl, C1-C6 alkoxy, C1-C6 monohaloalkyl, C1-C6 polyhaloalkyl, C1-C6 alkylamino, and C1-C6 dialkylamino. In a still further aspect, the aryl ring of Ar¹ is monosubstituted with a group selected from —F, —Cl, —CN, —NH₂, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, and —N(CH₃)CH(CH₃)₂. In a yet further aspect, the aryl ring of Ar¹ is monosubstituted with a group selected from —F, —Cl, —CN, —NH₂, methyl, —CH₂F, —CH₂Cl, —CHF₂, —CF₃, —CHCl₂, —CCl₃, —OCH₃, —NHCH₃, and —N(CH₃)₂. In an even further aspect, the aryl ring of Ar¹ is monosubstituted with a group selected from —F, —CN, —NH₂, methyl, —CH₂F, —CHF₂, —CF₃, —OCH₃, —NHCH₃, and —N(CH₃)₂.

In a further aspect, the heterocycloalkyl ring of Ar¹ is unsubstituted.

In a further aspect, the heterocycloalkyl ring of Ar¹ is substituted with 0, 1, 2, 3, 4, or 5 groups independently selected from —F, —Cl, —CN, —NH₂, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, —N(CH₃)CH(CH₃)₂, —(CH₂)₃CH₂OH, —(CH₂)₂CH₂OH, —CH₂CH₂OH, —CH₂OH, —(CH₂)₃CH₂NH₂, —(CH₂)₂CH₂NH₂, —CH₂CH₂NH₂, —CH₂NH₂, —(C═O)OH, —(C═O)OCH₃, —(C═O)OCH₂CH₃, —(C═O)O(CH₂)₂CH₃, —(C═O)OCH(CH₃)₂, —(C═O)NHCH₃, —(C═O)NHCH₂CH₃, —(C═O)NH(CH₂)₂CH₃, —(C═O)NHCH(CH₃)₂, —(C═O)N(CH₃)₂, —(C═O)N(CH₃)CH₂CH₃, and —(C═O)N(CH₃)CH(CH₃)₂. In a still further aspect, the heterocycloalkyl ring of Ar¹ is substituted with 0, 1, 2, 3, 4, or 5 groups independently selected from —F, —Cl, —CN, —NH₂, methyl, —CH₂F, —CH₂Cl, —CHF₂, —CF₃, —CHCl₂, —CCl₃, —OCH₃, —NHCH₃, —N(CH₃)₂, —CH₂CH₂OH, —CH₂OH, —CH₂CH₂NH₂, —CH₂NH₂, —(C═O)OH, —(C═O)OCH₃, —(C═O)OCH₂CH₃, —(C═O)NHCH₃, —(C═O)NHCH₂CH₃, and —(C═O)N(CH₃)₂. In a yet further aspect, the heterocycloalkyl ring of Ar¹ is substituted with 0, 1, 2, 3, 4, or 5 groups independently selected from —F, —CN, —NH₂, methyl, —CH₂F, —CHF₂, —CF₃, —OCH₃, —NHCH₃, —N(CH₃)₂, —CH₂OH, —CH₂NH₂, —(C═O)OH, —(C═O)OCH₃, —(C═O)NHCH₃, and —(C═O)N(CH₃)₂.

In a further aspect, the heterocycloalkyl ring of Ar¹ is substituted with 0, 1, 2, 3, or 4 groups independently selected from halogen, —OH, —CN, —NH₂, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C═O)OR⁵, and —(C═O)NR⁶ᵃR⁶ᵇ.

In a further aspect, the heterocycloalkyl ring of Ar¹ is substituted with 0, 1, 2, 3, or 4 groups independently selected from —F, —Cl, —CN, —NH₂, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, —N(CH₃)CH(CH₃)₂, —(CH₂)₃CH₂OH, —(CH₂)₂CH₂OH, —CH₂CH₂OH, —CH₂OH, —(CH₂)₃CH₂NH₂, —(CH₂)₂CH₂NH₂, —CH₂CH₂NH₂, —CH₂NH₂, —(C═O)OH, —(C═O)OCH₃, —(C═O)OCH₂CH₃, —(C═O)O(CH₂)₂CH₃, —(C═O)OCH(CH₃)₂, —(C═O)NHCH₃, —(C═O)NHCH₂CH₃, —(C═O)NH(CH₂)₂CH₃, —(C═O)NHCH(CH₃)₂, —(C═O)N(CH₃)₂, —(C═O)N(CH₃)CH₂CH₃, and —(C═O)N(CH₃)CH(CH₃)₂. In a still further aspect, the heterocycloalkyl ring of Ar¹ is substituted with 0, 1, 2, 3, or 4 groups independently selected from —F, —Cl, —CN, —NH₂, methyl, —CH₂F, —CH₂Cl, —CHF₂, —CF₃, —CHCl₂, —CCl₃, —OCH₃, —NHCH₃, —N(CH₃)₂, —CH₂CH₂OH, —CH₂OH, —CH₂CH₂NH₂, —CH₂NH₂, —(C═O)OH, —(C═O)OCH₃, —(C═O)OCH₂CH₃, —(C═O)NHCH₃, —(C═O)NHCH₂CH₃, and —(C═O)N(CH₃)₂. In a yet further aspect, the heterocycloalkyl ring of Ar¹ is substituted with 0, 1, 2, 3, or 4 groups independently selected from —F, —CN, —NH₂, methyl, —CH₂F, —CHF₂, —CF₃, —OCH₃, —NHCH₃, —N(CH₃)₂, —CH₂OH, —CH₂NH₂, —(C═O)OH, —(C═O)OCH₃, —(C═O)NHCH₃, and —(C═O)N(CH₃)₂.

In a further aspect, the heterocycloalkyl ring of Ar¹ is substituted with 0, 1, 2, or 3 groups independently selected from halogen, —OH, —CN, —NH₂, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C═O)OR⁵, and —(C═O)NR⁶ᵃR⁶ᵇ.

In a further aspect, the heterocycloalkyl ring of Ar¹ is substituted with 0, 1, 2, or 3 groups independently selected from —F, —Cl, —CN, —NH₂, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, —N(CH₃)CH(CH₃)₂, —(CH₂)₃CH₂OH, —(CH₂)₂CH₂OH, —CH₂CH₂OH, —CH₂OH, —(CH₂)₃CH₂NH₂, —(CH₂)₂CH₂NH₂, —CH₂CH₂NH₂, —CH₂NH₂, —(C═O)OH, —(C═O)OCH₃, —(C═O)OCH₂CH₃, —(C═O)O(CH₂)₂CH₃, —(C═O)OCH(CH₃)₂, —(C═O)NHCH₃, —(C═O)NHCH₂CH₃, —(C═O)NH(CH₂)₂CH₃, —(C═O)NHCH(CH₃)₂, —(C═O)N(CH₃)₂, —(C═O)N(CH₃)CH₂CH₃, and —(C═O)N(CH₃)CH(CH₃)₂. In a still further aspect, the heterocycloalkyl ring of Ar¹ is substituted with 0, 1, 2, or 3 groups independently selected from —F, —Cl, —CN, —NH₂, methyl, —CH₂F, —CH₂Cl, —CHF₂, —CF₃, —CHCl₂, —CCl₃, —OCH₃, —NHCH₃, —N(CH₃)₂, —CH₂CH₂OH, —CH₂OH, —CH₂CH₂NH₂, —CH₂NH₂, —(C═O)OH, —(C═O)OCH₃, —(C═O)OCH₂CH₃, —(C═O)NHCH₃, —(C═O)NHCH₂CH₃, and —(C═O)N(CH₃)₂. In a yet further aspect, the heterocycloalkyl ring of Ar¹ is substituted with 0, 1, 2, or 3 groups independently selected from —F, —CN, —NH₂, methyl, —CH₂F, —CHF₂, —CF₃, —OCH₃, —NHCH₃, —N(CH₃)₂, —CH₂OH, —CH₂NH₂, —(C═O)OH, —(C═O)OCH₃, —(C═O)NHCH₃, and —(C═O)N(CH₃)₂.

In a further aspect, the heterocycloalkyl ring of Ar¹ is substituted with 0, 1, or 2 groups independently selected from halogen, —OH, —CN, —NH₂, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C═O)OR⁵, and —(C═O)NR⁶ᵃR⁶ᵇ.

In a further aspect, the heterocycloalkyl ring of Ar¹ is substituted with 0, 1, or 2 groups independently selected from —F, —Cl, —CN, —NH₂, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, —N(CH₃)CH(CH₃)₂, —(CH₂)₃CH₂OH, —(CH₂)₂CH₂OH, —CH₂CH₂OH, —CH₂OH, —(CH₂)₃CH₂NH₂, —(CH₂)₂CH₂NH₂, —CH₂CH₂NH₂, —CH₂NH₂, —(C═O)OH, —(C═O)OCH₃, —(C═O)OCH₂CH₃, —(C═O)O(CH₂)₂CH₃, —(C═O)OCH(CH₃)₂, —(C═O) NHCH₃, —(C═O)NHCH₂CH₃, —(C═O)NH (CH$_2$)$_2$CH$_3$, —(C=O)NHCH(CH$_3$)$_2$, —(C=O)N(CH$_3$)$_2$, —(C=O)N(CH$_3$)CH$_2$CH$_3$, and —(C=O)N(CH$_3$)CH(CH$_3$)$_2$. In a still further aspect, the heterocycloalkyl ring of Ar$^1$ is substituted with 0, 1, or 2 groups independently selected from —F, —Cl, —CN, —NH$_2$, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —CH$_2$CH$_2$OH, —CH$_2$OH, —CH$_2$CH$_2$NH$_2$, —CH$_2$NH$_2$, —(C=O)OH, —(C=O)OCH$_3$, —(C=O)OCH$_2$CH$_3$, —(C=O)NHCH$_3$, —(C=O)NHCH$_2$CH$_3$, and —(C=O)N(CH$_3$)$_2$. In a yet further aspect, the heterocycloalkyl ring of Ar$^1$ is substituted with 0, 1, or 2 groups independently selected from —F, —CN, —NH$_2$, methyl, —CH$_2$F, —CHF$_2$, —CF$_3$, —OCH$_3$, —NHCH$_3$, —N(CH$_3$)$_2$, —CH$_2$OH, —CH$_2$NH$_2$, —(C=O)OH, —(C=O)OCH$_3$, —(C=O)NHCH$_3$, and —(C=O)N(CH$_3$)$_2$.

In a further aspect, the heterocycloalkyl ring of Ar$^1$ is monosubstituted with a group selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$.

In a further aspect, the heterocycloalkyl ring of Ar$^1$ is monosubstituted with a group selected from —F, —Cl, —CN, —NH$_2$, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)CH(CH$_3$)$_2$, —(CH$_2$)$_3$CH$_2$OH, —(CH$_2$)$_2$CH$_2$OH, —CH$_2$CH$_2$OH, —CH$_2$OH, —(CH$_2$)$_3$CH$_2$NH$_2$, —(CH$_2$)$_2$CH$_2$NH$_2$, —CH$_2$CH$_2$NH$_2$, —CH$_2$NH$_2$, —(C=O)OH, —(C=O)OCH$_3$, —(C=O)OCH$_2$CH$_3$, —(C=O)O(CH$_2$)$_2$CH$_3$, —(C=O)OCH(CH$_3$)$_2$, —(C=O)NHCH$_3$, —(C=O)NHCH$_2$CH$_3$, —(C=O)NH(CH$_2$)$_2$CH$_3$, —(C=O)NHCH(CH$_3$)$_2$, —(C=O)N(CH$_3$)$_2$, —(C=O)N(CH$_3$)CH$_2$CH$_3$, and —(C=O)N(CH$_3$)CH(CH$_3$)$_2$. In a still further aspect, the heterocycloalkyl ring of Ar$^1$ is monosubstituted with a group selected from —F, —Cl, —CN, —NH$_2$, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —CH$_2$CH$_2$OH, —CH$_2$OH, —CH$_2$CH$_2$NH$_2$, —CH$_2$NH$_2$, —(C=O)OH, —(C=O)OCH$_3$, —(C=O)OCH$_2$CH$_3$, —(C=O)NHCH$_3$, —(C=O)NHCH$_2$CH$_3$, and —(C=O)N(CH$_3$)$_2$. In a yet further aspect, the heterocycloalkyl ring of Ar$^1$ is monosubstituted with a group selected from —F, —CN, —NH$_2$, methyl, —CH$_2$F, —CHF$_2$, —CF$_3$, —OCH$_3$, —NHCH$_3$, —N(CH$_3$)$_2$, —CH$_2$OH, —CH$_2$NH$_2$, —(C=O)OH, —(C=O)OCH$_3$, —(C=O)NHCH$_3$, and —(C=O)N(CH$_3$)$_2$.

b. R$^2$ Groups

In one aspect, R$^2$ is selected from hydrogen, C1-C4 alkyl, and an amine protecting group. In a further aspect, R$^2$ is hydrogen.

In a further aspect, R$^2$ is selected from hydrogen and C1-C4 alkyl. In a still further aspect, R$^2$ is selected from hydrogen, methyl, ethyl, n-propyl, s-propyl, i-propyl, n-butyl, s-butyl, i-butyl, and t-butyl. In a yet further aspect, R$^2$ is selected from hydrogen, methyl, ethyl, n-propyl, s-propyl, and i-propyl. In an even further aspect, R$^2$ is selected from hydrogen, methyl, and ethyl. In a still further aspect, R$^2$ is selected from hydrogen and methyl.

In a further aspect, R$^2$ is an amine protecting group. In a still further aspect, R$^2$ is selected from Fmoc, BOC, Cbz, acetyl, trifluoroacetamide, phthalimide, benzyl, triphenylmethylamine, benzylideneamine, and p-toluenesulfonamide. In a yet further aspect, R$^2$ is selected from Fmoc, BOC, and Cbz. In an even further aspect, R$^2$ is Fmoc. In a still further aspect, R$^2$ is BOC. In a yet further aspect, R$^2$ is Cbz.

In a further aspect, R$^2$ is a C1-C4 alkyl. In a still further aspect, R$^2$ is selected from methyl, ethyl, n-propyl, s-propyl, i-propyl, n-butyl, s-butyl, i-butyl, and t-butyl. In a yet further aspect, R$^2$ is selected from methyl, ethyl, n-propyl, s-propyl, and i-propyl. In an even further aspect, R$^2$ is selected from methyl and ethyl. In a still further aspect, R$^2$ is methyl. In a yet further aspect, R$^2$ is ethyl.

In a further aspect, R$^2$ is selected from hydrogen and an amine protecting group. In a still further aspect, R$^2$ is selected from hydrogen, Fmoc, BOC, Cbz, acetyl, trifluoroacetamide, phthalimide, benzyl, triphenylmethylamine, benzylideneamine, and p-toluenesulfonamide. In a yet further aspect, R$^2$ is selected from hydrogen, Fmoc, BOC, and Cbz. In an even further aspect, R$^2$ is selected from hydrogen and Fmoc. In a still further aspect, R$^2$ is selected from hydrogen and BOC. In a yet further aspect, R$^2$ is selected from hydrogen and Cbz.

c. R$^3$ Groups

In one aspect, R$^3$ is selected from hydrogen and a hydroxyl protecting group, or wherein R$^3$ and R$^4$ together comprise a divalent moiety having a structure represented by a formula:

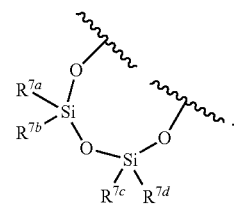

In a further aspect, R$^3$ is hydrogen. In a still further aspect, each of R$^2$ and R$^3$ are hydrogen.

In various further aspects, R$^3$ is selected from hydrogen, MOM, THP, t-butyl ether, allyl ether, benzyl, TIPDS, TBDMS, TBDPS, acetyl, pivalic acid ester, acetonide, benzoyl, and benzylidene acetal.

In a further aspect, R$^3$ is a hydroxyl protecting group. In a still further aspect, R$^3$ is selected from MOM, THP, t-butyl ether, allyl ether, benzyl, TIPDS, TBDMS, TBDPS, acetyl, pivalic acid ester, acetonide, benzoyl, and benzylidene acetal. In a yet further aspect, R$^3$ is MOM. In an even further aspect, R$^3$ is THP. In a still further aspect, R$^3$ is t-butyl ether. In a yet further aspect, R$^3$ is allyl ether. In an even further aspect, R$^3$ is TIPDS. In a still further aspect, R$^3$ is TBDMS. In a yet further aspect, R$^3$ is TBDPS. In an even further aspect, R$^3$ is acetyl. In a still further aspect, R$^3$ is pivalic acid ester. In a yet further aspect, R$^3$ is acetonide. In an even further aspect, R$^3$ is benzoyl. In a still further aspect, R$^3$ is benzylidene acetal.

d. R$^4$ Groups

In one aspect, R$^4$ is selected from hydrogen, C1-C8 alkyl, and a hydroxyl protecting group. In a further aspect, R$^4$ is hydrogen. In a still further aspect, each of R$^2$, R$^3$, and R$^4$ are hydrogen. In a yet further aspect, In a yet further aspect, each of R$^2$ and R$^4$ are hydrogen.

In various further aspects, $R^4$ is selected from hydrogen and C1-C8 alkyl. In a further aspect, $R^4$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, hexyl, heptyl, cyclopropyl, cyclobutyl, cyclopentyl, cyclohexyl, cycloheptyl, and cyclooctyl. In a still further aspect, $R^4$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, hexyl, cyclopropyl, cyclobutyl, cyclopentyl, and cyclohexyl. In a yet further aspect, $R^4$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, cyclopropyl, cyclobutyl, and cyclopentyl. In an even further aspect, $R^4$ is selected from hydrogen, methyl, ethyl, propyl, isopropyl, tert-butyl, sec-butyl, isobutyl, cyclopropyl, and cyclobutyl. In a still further aspect, $R^4$ is selected from hydrogen, methyl, ethyl, propyl, isopropyl, and cyclopropyl. In a yet further aspect, $R^4$ is selected from hydrogen, methyl, and ethyl. In an even further aspect, $R^4$ is selected from hydrogen and methyl.

In a further aspect, $R^4$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, hexyl, and heptyl. In a still further aspect, $R^4$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, and hexyl. In a yet further aspect, $R^4$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In an even further aspect, $R^4$ is selected from hydrogen, methyl, ethyl, propyl, isopropyl, tert-butyl, sec-butyl, and isobutyl. In a still further aspect, $R^4$ is selected from hydrogen, methyl, ethyl, propyl, and isopropyl.

In a further aspect, $R^4$ is selected from hydrogen and a hydroxyl protecting group. In a still further aspect, $R^4$ is selected from hydrogen, MOM, THP, t-butyl ether, allyl ether, benzyl, TIPDS, TBDMS, TBDPS, acetyl, pivalic acid ester, acetonide, benzoyl, and benzylidene acetal.

In a further aspect, $R^4$ is a hydroxyl protecting group. In a still further aspect, $R^4$ is a hydroxyl protecting group selected from MOM, THP, t-butyl ether, allyl ether, benzyl, TIPDS, TBDMS, TBDPS, acetyl, pivalic acid ester, acetonide, benzoyl, and benzylidene acetal. In a yet further aspect, $R^4$ is MOM. In an even further aspect, $R^4$ is THP. In a still further aspect, $R^4$ is t-butyl ether. In a yet further aspect, $R^4$ is allyl ether. In an even further aspect, $R^4$ is TIPDS. In a still further aspect, $R^4$ is TBDMS. In a yet further aspect, $R^4$ is TBDPS. In an even further aspect, $R^4$ is acetyl. In a still further aspect, $R^4$ is pivalic acid ester. In a yet further aspect, $R^4$ is acetonide. In an even further aspect, $R^4$ is benzoyl. In a still further aspect, $R^4$ is benzylidene acetal.

e. $R^5$ Groups

In one aspect, each $R^5$ is independently selected from hydrogen, C1-C8 alkyl, and a hydroxyl protecting group. In a further aspect, each $R^5$ is hydrogen.

In various further aspects, each $R^5$ is selected from hydrogen and C1-C8 alkyl. In a further aspect, each $R^5$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, hexyl, heptyl, cyclopropyl, cyclobutyl, cyclopentyl, cyclohexyl, cycloheptyl, and cyclooctyl. In a still further aspect, each $R^5$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, hexyl, cyclopropyl, cyclobutyl, cyclopentyl, and cyclohexyl. In a yet further aspect, each $R^5$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, cyclopropyl, cyclobutyl, and cyclopentyl. In an even further aspect, each $R^5$ is selected from hydrogen, methyl, ethyl, propyl, isopropyl, tert-butyl, sec-butyl, isobutyl, cyclopropyl, and cyclobutyl. In a still further aspect, each $R^5$ is selected from hydrogen, methyl, ethyl, propyl, isopropyl, and cyclopropyl. In a yet further aspect, each $R^5$ is selected from hydrogen, methyl, and ethyl. In an even further aspect, each $R^5$ is selected from hydrogen and methyl.

In a further aspect, each $R^5$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, hexyl, and heptyl. In a still further aspect, each $R^5$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, and hexyl. In a yet further aspect, each $R^5$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In an even further aspect, each $R^5$ is selected from hydrogen, methyl, ethyl, propyl, isopropyl, tert-butyl, sec-butyl, and isobutyl. In a still further aspect, each $R^5$ is selected from hydrogen, methyl, ethyl, propyl, and isopropyl.

In a further aspect, each $R^5$ is selected from hydrogen and a hydroxyl protecting group. In a still further aspect, each $R^5$ is selected from hydrogen, MOM, THP, t-butyl ether, allyl ether, benzyl, TIPDS, TBDMS, TBDPS, acetyl, pivalic acid ester, acetonide, benzoyl, and benzylidene acetal.

In a further aspect, each $R^5$ is a hydroxyl protecting group. In a still further aspect, each $R^5$ is hydroxyl protecting group selected from MOM, THP, t-butyl ether, allyl ether, benzyl, TIPDS, TBDMS, TBDPS, acetyl, pivalic acid ester, acetonide, benzoyl, and benzylidene acetal. In a yet further aspect, each $R^5$ is MOM. In an even further aspect, each $R^5$ is THP. In a still further aspect, each $R^5$ is t-butyl ether. In a yet further aspect, each $R^5$ is allyl ether. In an even further aspect, each $R^5$ is TIPDS. In a still further aspect, each $R^5$ is TBDMS. In a yet further aspect, each $R^5$ is TBDPS. In an even further aspect, each $R^5$ is acetyl. In a still further aspect, each $R^5$ is pivalic acid ester. In a yet further aspect, each $R^5$ is acetonide. In an even further aspect, each $R^5$ is benzoyl. In a still further aspect, each $R^5$ is benzylidene acetal.

f. $R^6$ Groups

In one aspect, each of $R^{6a}$ and $R^{6b}$ is independently selected from hydrogen, C1-C4 alkyl, and an amine protecting group. In a further aspect, each of $R^{6a}$ and $R^{6b}$ is hydrogen. In a still further aspect, each of $R^{6a}$ and $R^{6b}$ is methyl. In a yet further aspect, each of $R^{6a}$ and $R^{6b}$ is ethyl.

In various further aspects, each of $R^{6a}$ and $R^{6b}$ is independently selected from hydrogen and C1-C4 alkyl. In a further aspect, each of $R^{6a}$ and $R^{6b}$ is independently selected from hydrogen, methyl, ethyl, n-propyl, s-propyl, i-propyl, n-butyl, s-butyl, i-butyl, and t-butyl. In a still further aspect, each of $R^{6a}$ and $R^{6b}$ is independently selected from hydrogen, methyl, ethyl, n-propyl, s-propyl, and i-propyl. In a yet further aspect, each of $R^{6a}$ and $R^{6b}$ is independently selected from hydrogen, methyl, and ethyl. In an even further aspect, each of $R^{6a}$ and $R^{6b}$ is independently selected from hydrogen and methyl.

In a further aspect, each of $R^{6a}$ and $R^{6b}$ is an amine protecting group. In a still further aspect, each of $R^{6a}$ and $R^{6b}$ is an amine protecting group selected from Fmoc, BOC, Cbz, acetyl, trifluoroacetamide, phthalimide, benzyl, triphenylmethylamine, benzylideneamine, and p-toluenesulfonamide. In a yet further aspect, each of $R^{6a}$ and $R^{6b}$ is selected from Fmoc, BOC, and Cbz. In an even further aspect, each of $R^{6a}$ and $R^{6b}$ is Fmoc. In a still further aspect, each of $R^{6a}$ and $R^{6b}$ is BOC. In a yet further aspect, each of $R^{6a}$ and $R^{6b}$ is Cbz.

In a further aspect, each of $R^{6a}$ and $R^{6b}$ is independently a C1-C4 alkyl. In a still further aspect, each of $R^{6a}$ and $R^{6b}$ is independently selected from methyl, ethyl, n-propyl, s-propyl, i-propyl, n-butyl, s-butyl, i-butyl, and t-butyl. In a yet further aspect, each of $R^{6a}$ and $R^{6b}$ is independently selected from methyl, ethyl, n-propyl, s-propyl, and i-propyl. In an even further aspect, each of $R^{6a}$ and $R^{6b}$ is independently selected from methyl and ethyl. In a still further aspect, each of $R^{6a}$ and $R^{6b}$ is methyl. In a yet further aspect, each of $R^{6a}$ and $R^{6b}$ is ethyl.

In a further aspect, each of $R^{6a}$ and $R^{6b}$ is independently selected from hydrogen and an amine protecting group. In a still further aspect, each of $R^{6a}$ and $R^{6b}$ is independently selected from hydrogen, Fmoc, BOC, Cbz, acetyl, trifluoroacetamide, phthalimide, benzyl, triphenylmethylamine, benzylideneamine, and p-toluenesulfonamide. In a yet further aspect, each of $R^{6a}$ and $R^{6b}$ is independently selected from hydrogen, Fmoc, BOC, and Cbz. In an even further aspect, each of $R^{6a}$ and $R^{6b}$ is independently selected from hydrogen and Fmoc. In a still further aspect, each of $R^{6a}$ and $R^{6b}$ is independently selected from hydrogen and BOC. In a yet further aspect, each of $R^{6a}$ and $R^{6b}$ is independently selected from hydrogen and Cbz.

In a further aspect, $R^{6a}$ is hydrogen and $R^{6b}$ is selected from hydrogen and C1-C4 alkyl. In a still further aspect, $R^{6a}$ is hydrogen and $R^{6b}$ is selected from hydrogen, methyl, ethyl, n-propyl, s-propyl, i-propyl, n-butyl, s-butyl, i-butyl, and t-butyl. In a yet further aspect, $R^{6a}$ is hydrogen and $R^{6b}$ is selected from hydrogen, methyl, ethyl, n-propyl, s-propyl, and i-propyl. In an even further aspect, $R^{6a}$ is hydrogen and $R^{6b}$ is selected from hydrogen, methyl, and ethyl. In a still further aspect, $R^{6a}$ is hydrogen and $R^{6b}$ is selected from hydrogen and methyl.

In a further aspect, $R^{6a}$ is hydrogen and $R^{6b}$ is a C1-C4 alkyl. In a still further aspect, $R^{6a}$ is hydrogen and $R^{6b}$ is selected from methyl, ethyl, n-propyl, s-propyl, i-propyl, n-butyl, s-butyl, i-butyl, and t-butyl. In a yet further aspect, $R^{6a}$ is hydrogen and $R^{6b}$ is selected from methyl, ethyl, n-propyl, s-propyl, and i-propyl. In an even further aspect, $R^{6a}$ is hydrogen and $R^{6b}$ is selected from methyl and ethyl. In a still further aspect, $R^{6a}$ is hydrogen and $R^{6b}$ is methyl. In a yet further aspect, $R^{6a}$ is hydrogen and $R^{6b}$ is ethyl.

g. $R^{7A}$, $R^{7B}$, $R^{7C}$, and $R^{7D}$ Groups

In one aspect, each of $R^{7a}$, $R^{7b}$, $R^{7c}$, and $R^{7d}$ is independently selected from methyl, ethyl, propyl, and butyl.

In a further aspect, each of $R^{7a}$, $R^{7b}$, $R^{7c}$, and $R^{7d}$ is methyl. In a still further aspect, each of $R^{7a}$, $R^{7b}$, $R^{7c}$, and $R^{7d}$ is ethyl. In a yet further aspect, each of $R^{7a}$, $R^{7b}$, $R^{7c}$, and $R^{7d}$ is propyl. In an even further aspect, each of $R^{7a}$, $R^{7b}$, $R^{7c}$, and $R^{7d}$ is butyl.

In a further aspect, $R^{7a}$ is methyl and each of $R^{7b}$, $R^{7c}$, and $R^{7d}$ is independently selected from methyl, ethyl, propyl, and butyl. In a still further aspect, $R^{7b}$ is methyl and each of $R^{7a}$, $R^{7c}$, and $R^{7d}$ is independently selected from methyl, ethyl, propyl, and butyl. In a yet further aspect, $R^{7c}$ is methyl and each of $R^{7a}$, $R^{7b}$, and $R^{7d}$ is independently selected from methyl, ethyl, propyl, and butyl. In an even further aspect, $R^{7d}$ is methyl and each of $R^{7a}$, $R^{7b}$, and $R^{7c}$ is independently selected from methyl, ethyl, propyl, and butyl.

2. Example Compounds

In one aspect, a compound can have a structure represented by a formula:

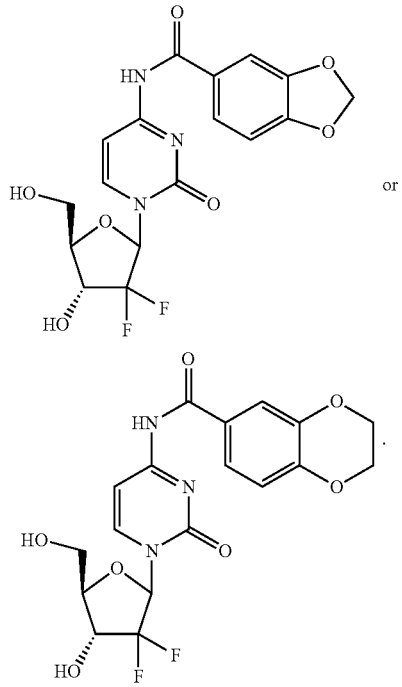

or

In one aspect, a compound can have a structure represented by a formula:

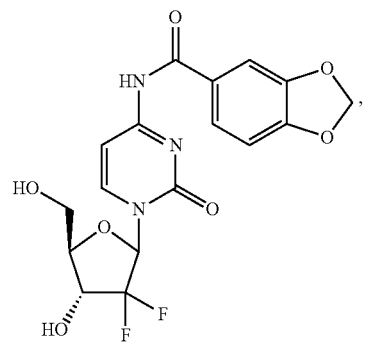

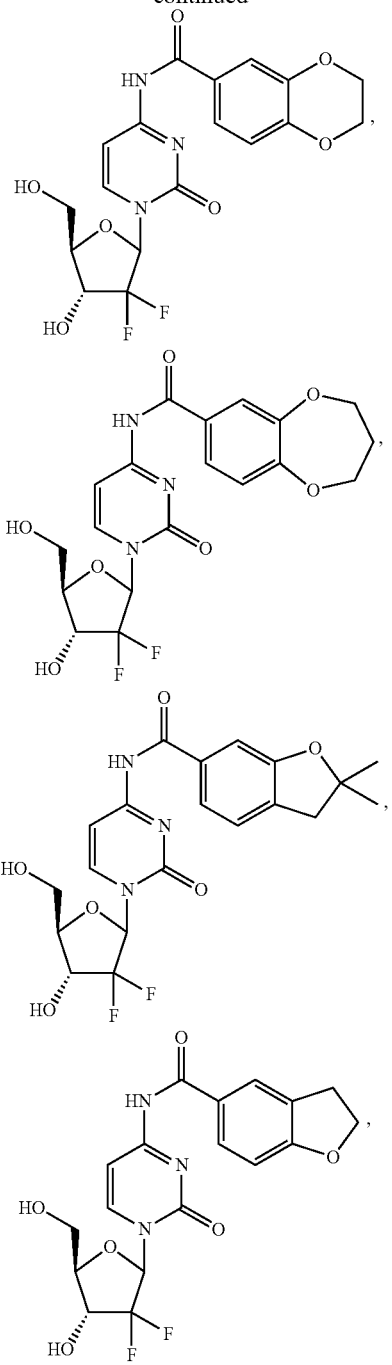
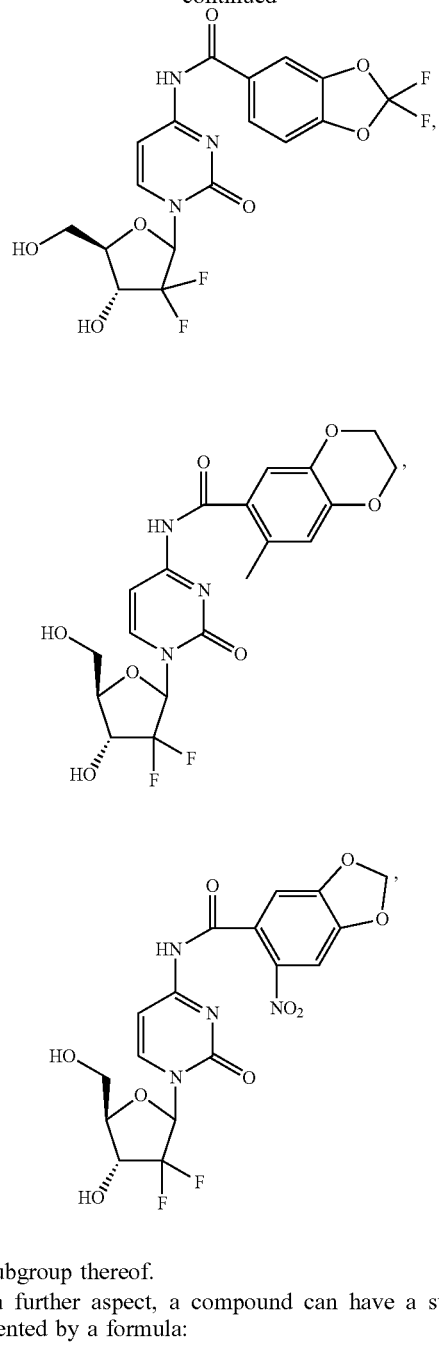
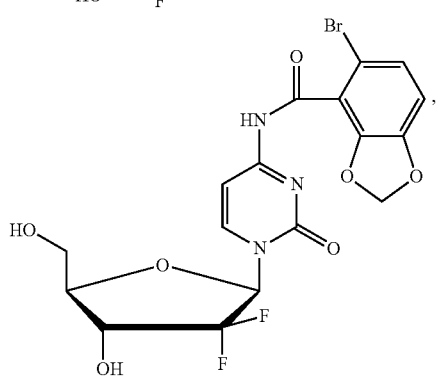
or a subgroup thereof.
In a further aspect, a compound can have a structure represented by a formula:
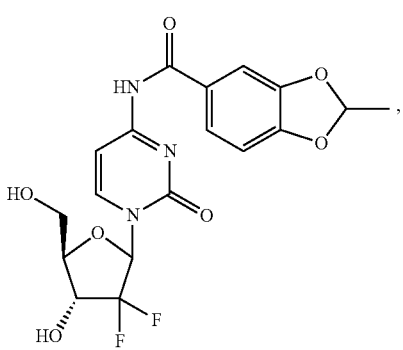

41
-continued
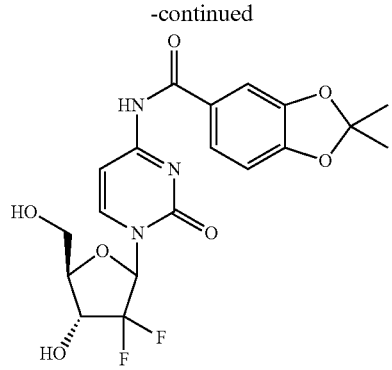
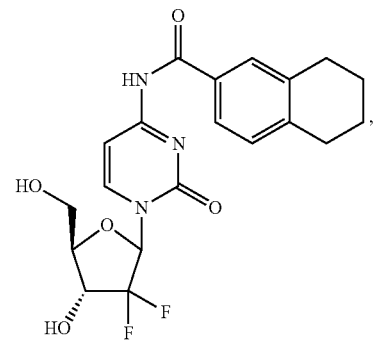
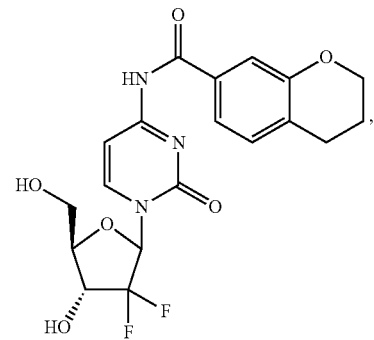
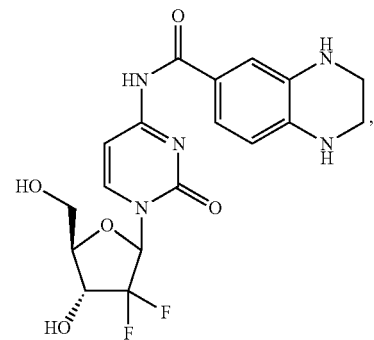
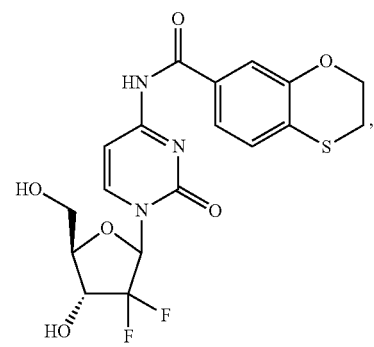
42
-continued
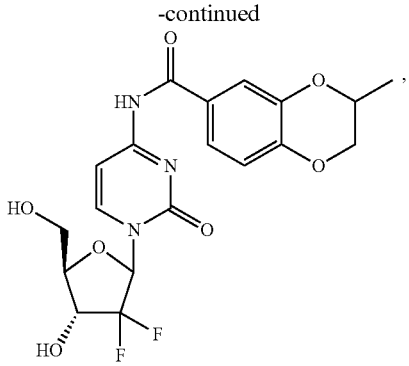
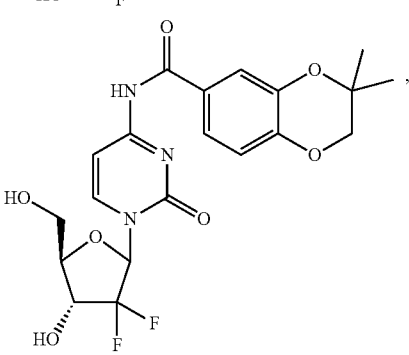
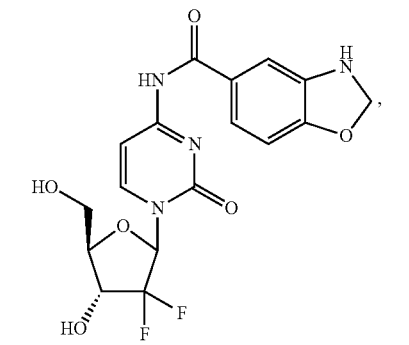
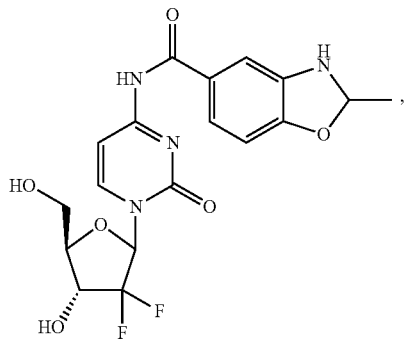

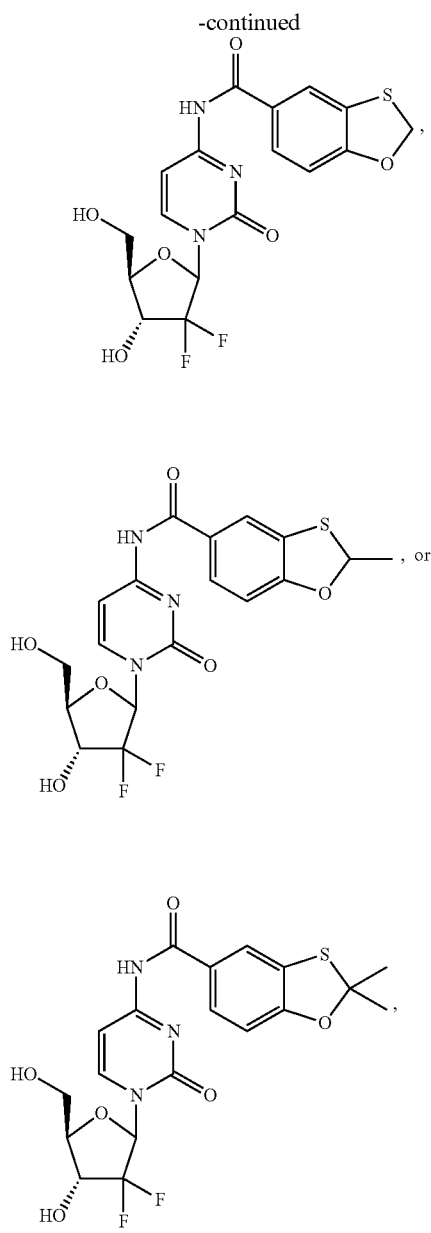
or a subgroup thereof.
In a further aspect, a compound can have a structure represented by a formula:
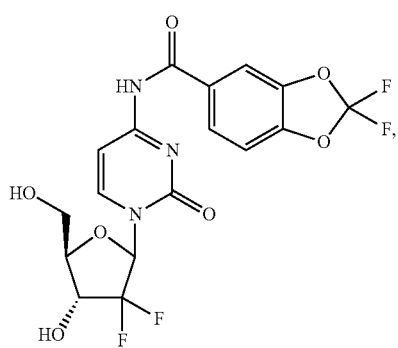 [SMILES: CC1(C)Cc2ccc(C(=O)Nc3ccn(C4O[C@H](CO)[C@@H](O)C4(F)F)c(=O)n3)cc2O1]
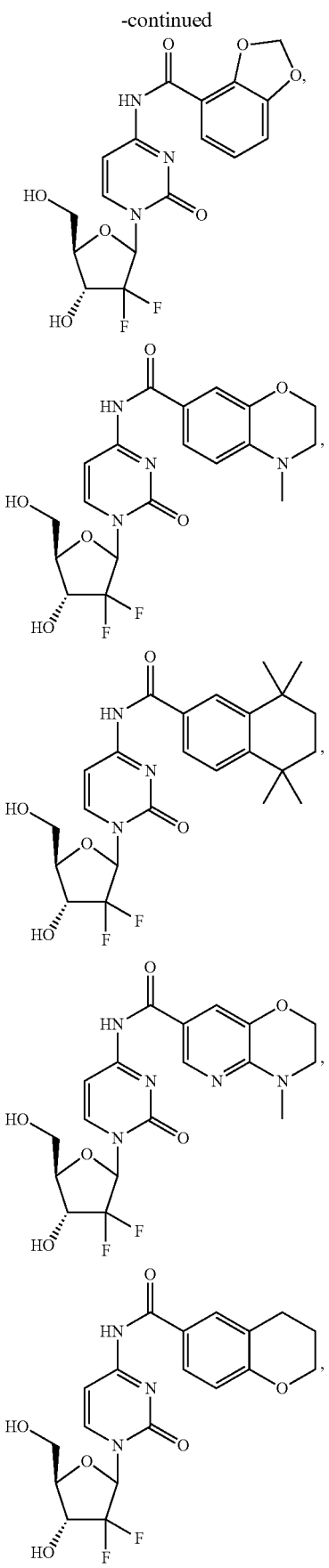

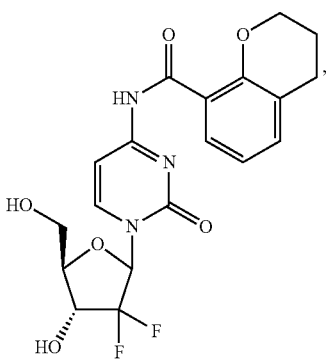
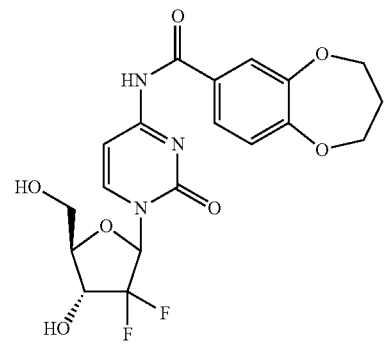
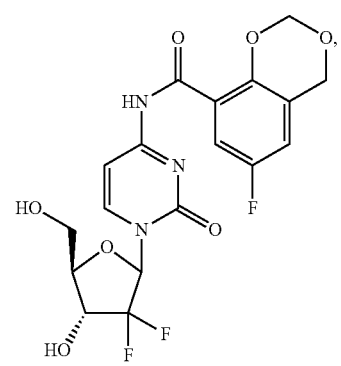
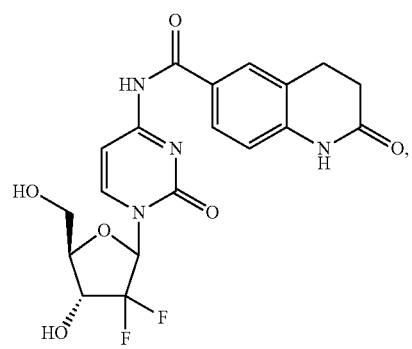
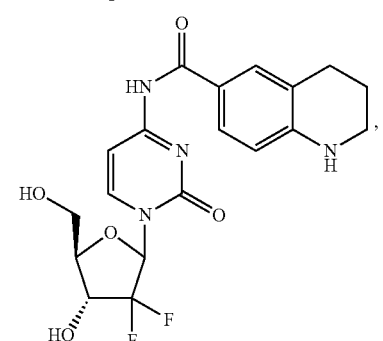
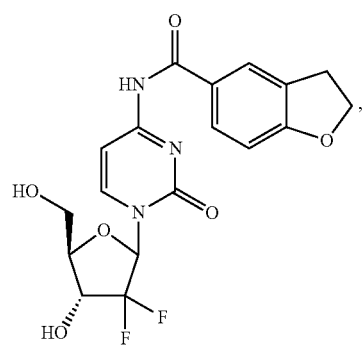
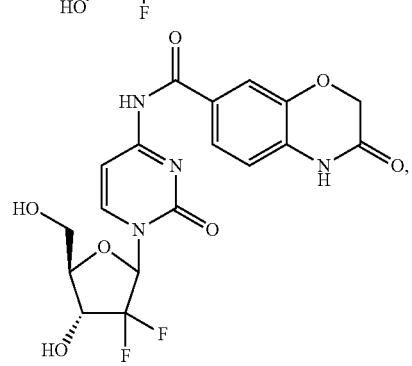
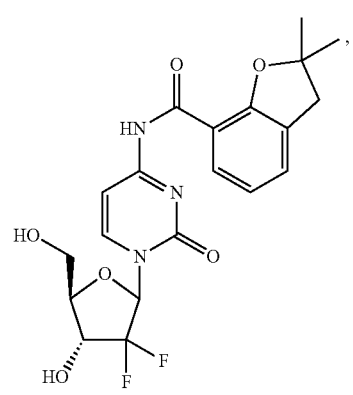
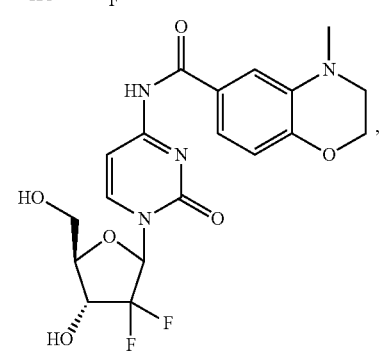

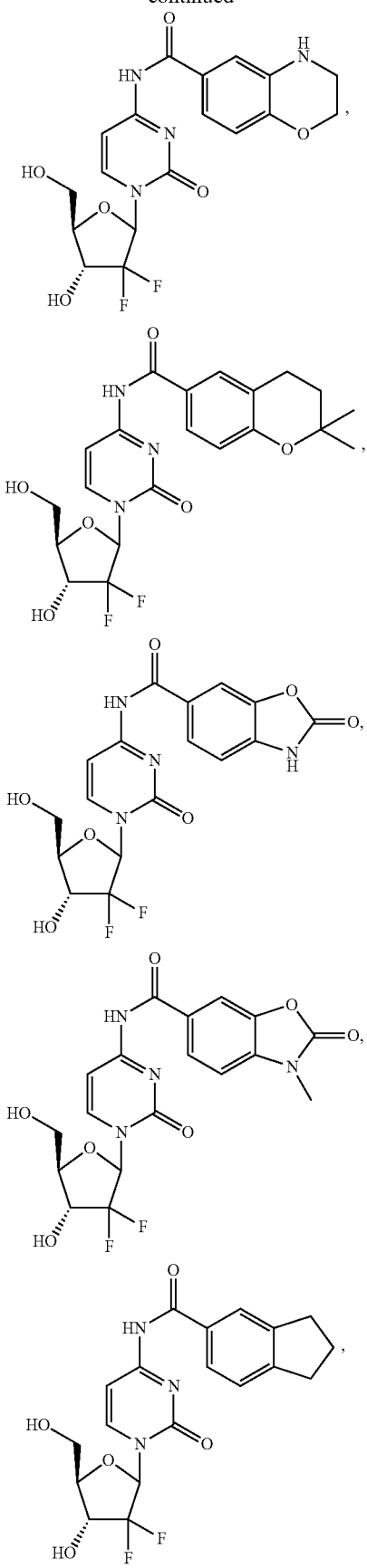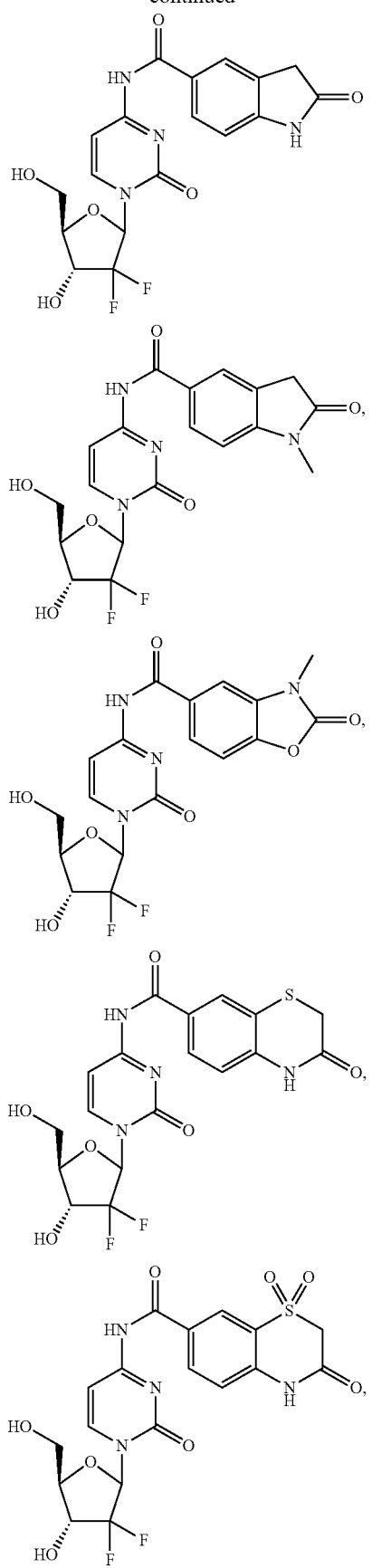

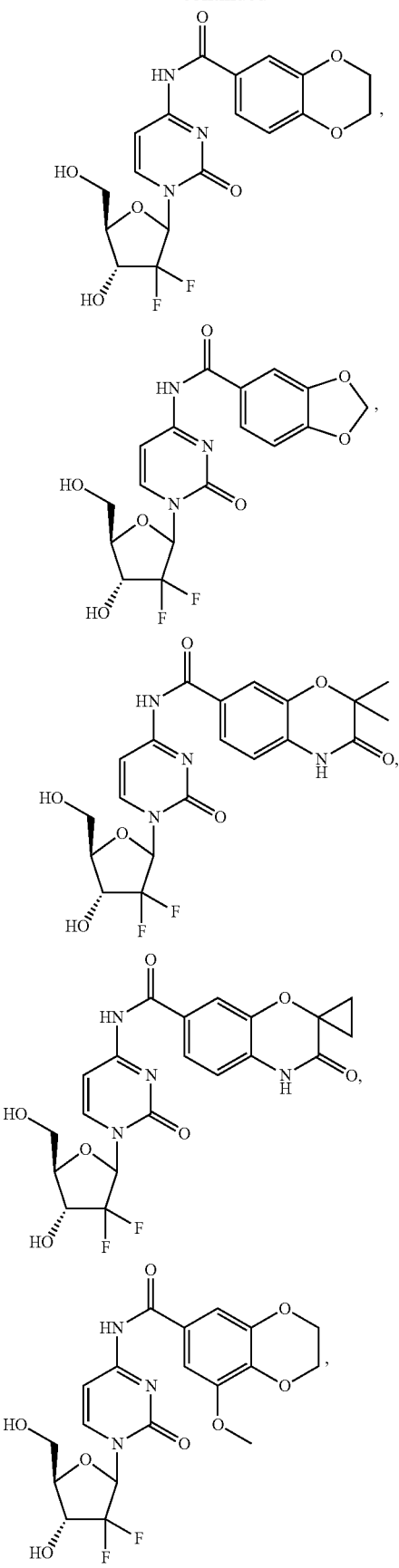
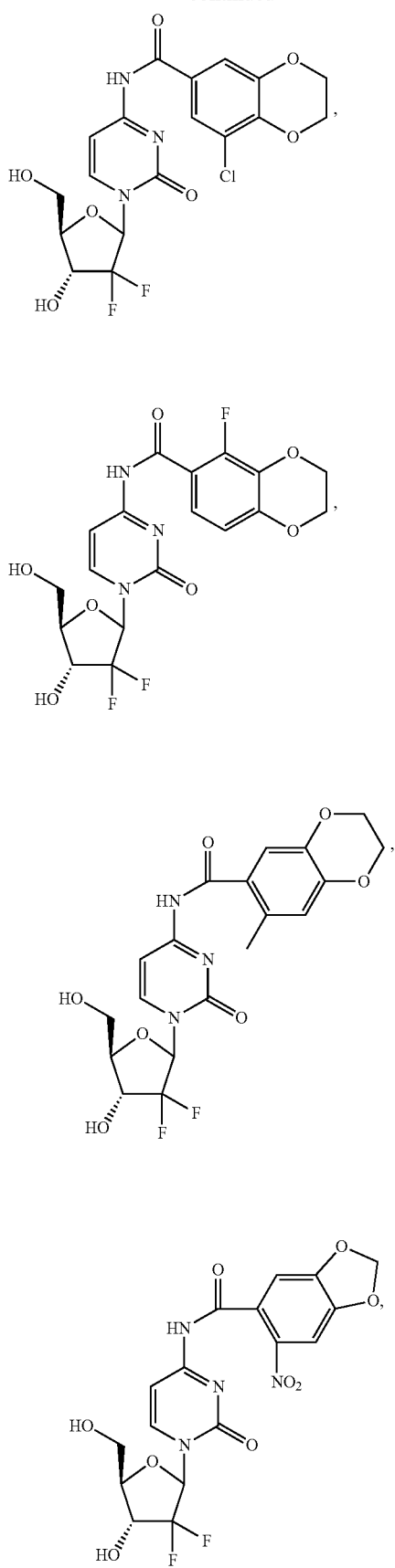

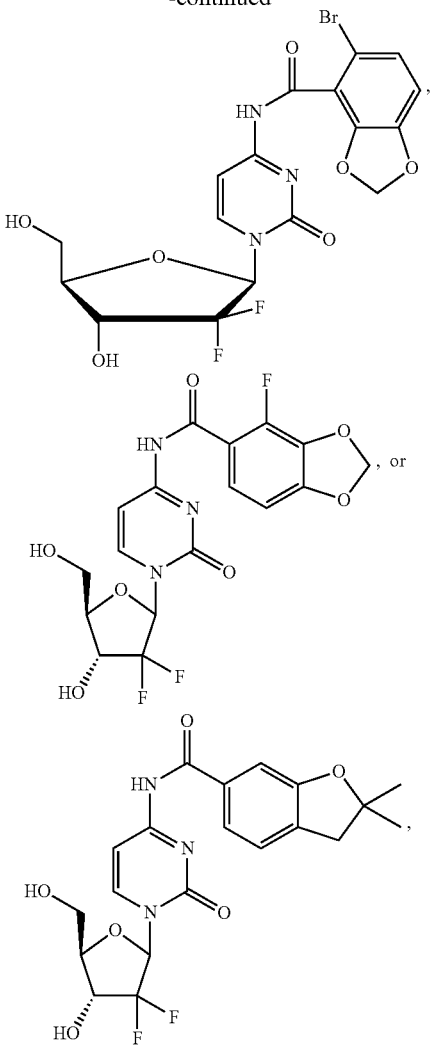

or a subgroup thereof.

It is understood that the disclosed compounds can be used in connection with the disclosed methods, compositions, kits, and uses.

C. Flaviviridae Viruses

The Flaviviridae are a large family of positive-stranded RNA viruses, including: hepatitis C virus (HCV), yellow fever virus, dengue virus, tick-born encephalitis virus and West Nile virus. Although members of this family exhibit a number of unique biological properties, all members of the Flaviviridae possess a similar genome organization and replication strategy. All flavivirus genomes consist of a single strand of RNA, which contains a single open reading frame, flanked by a 5' and a 3' non-coding region. After cellular entry and genome uncoating, this positive-sense RNA is translated by the host ribosomes as a single, long polyprotein that is co- and post-translationally cleaved by host and viral proteases into separate proteins. The N-terminus of the flavivirus polyprotein is processed into the capsid and virus envelope structural proteins. The C-terminus of the polyprotein is processed to generate the nonstructural proteins necessary to replicate the virus genome, including: a protease, a helicase and a RNA-dependent RNA polymerase. The replication of flavivirus genomes takes place within intracellular membrane compartments and begins with the synthesis of a genome-length negative strand, which is subsequently used as a template to produce additional positive-sense genomes for both genome replication and translation of virus proteins. After replication, single-stranded, positive-sense genomes are packaged into virions at membrane-bound vesicles, and subsequently transported by the host secretory pathway to the cell surface for release.

Unique among the Flaviviridae, HCV replicates exclusively within liver cells. The HCV genome is a positive-sense, single-stranded RNA of ~9.5 kb (see FIG. 1 for schematic illustration of the HCV genome), which encodes a single polyprotein precursor of approximately 3,000 residues which is translated under the control of an internal ribosome entry site ("IRIS") located within the 5' nontranslated region ("NTR"; see Choo, Q. L., et al. (1991) *Proc Natl Acad Sci USA* 88, 2451-2455). The HCV precursor, C-E1-E2-p7-NS2-NS3-NS4A-NS4B-NS5A-NS5B, is proteolytically processed by host signal peptidase into a core protein (C), three envelop proteins (E1, E2 type A, and E2 type B), and a small polytopic membrane protein p7, and by two viral proteases into six nonstructural (NS) proteins (NS2, NS3, NS4A, NS4B, NS5A, and NS5B). HCV follows a replication strategy similar to that of other plus-strand RNA viruses: following entry and uncoating in the cytoplasm of host cells, the viral genome acts as a template for the synthesis of a minus-strand RNA, which then serves as a template for the synthesis of progeny genomic RNA (see Choo, Q. L., et al., ibid; and Hwang, S. B., et al. (1997) *Virology* 227, 439-446). HCV NS5B, a membrane-associated RNA polymerase, catalyzes the synthesis of both plus and minus RNA strands. Replication appears to take place at the perinuclear endoplasmic reticulum and requires a replication complex of NS5B, NS3, NS4A, and possibly other viral or cellular proteins.

D. Inhibition of Viral and Cellular Replication

Without wishing to be bound by a particular theory, it is believed that the disclosed compounds of the present invention and products of disclosed methods of making may be converted to gemcitabine (dFdC) upon intracellular cleavage of the amine protecting group by the action of carboxylesterase 2, an enzyme that is predominantly expressed in liver cells. Subsequently, the disclosed analogs and metabolites of the disclosed analogs, such as dFdC, will be activated by a "self-potentiation mechanism" (see FIG. 2; Mackey, J. R., et al. (1999) *J Natl Cancer Inst* 91, 1876-1881). Thus, the antiproliferative activities are believed to be exerted through multiple mechanisms. Initially, the disclosed analogs and metabolites of the disclosed analogs are believed to be intracellularly phosphorylated by deoxycytidine kinase (dCK) in a rate-limiting step (Blackstock, A. W., et al. (2001) *Clin Cancer Res* 7, 3263-3268) to generate a monophosphate form. This monophosphate form is subsequently phosphorylated by nucleotide kinases to produce the active metabolites such as the diphosphate and triphosphate derivatives of the disclosed compounds and metabolites of the disclosed analogs. It has been shown that the triphosphate form of gemcitabine (dFdCTP) can function as a masked chain terminator when incorporated into DNA (Richardson, K. A., et al. (2004) *Biochem Pharmacol* 68, 2337-2346) or RNA (Ruiz van Haperen, V. W., et al. (1993) *Biochem Pharmacol* 46, 762-766), due to the fact that once dFdCTP is incorporated into a newly-synthesized DNA strand, DNA polymerases are able to incorporate one additional nucleotide before replication is blocked. Thus, at a stalled replication fork, the incorporated gemcitabine is shielded from the exonuclease activity of replicative DNA polymerases. Without wishing to be bound by a particular theory, it is believed that the disclosed compounds of the present invention and metabolites of the disclosed analogs can directly interrupt viral genome synthesis by being incorporated into a replicating virus genome to block further genome replication.

Figure 2:
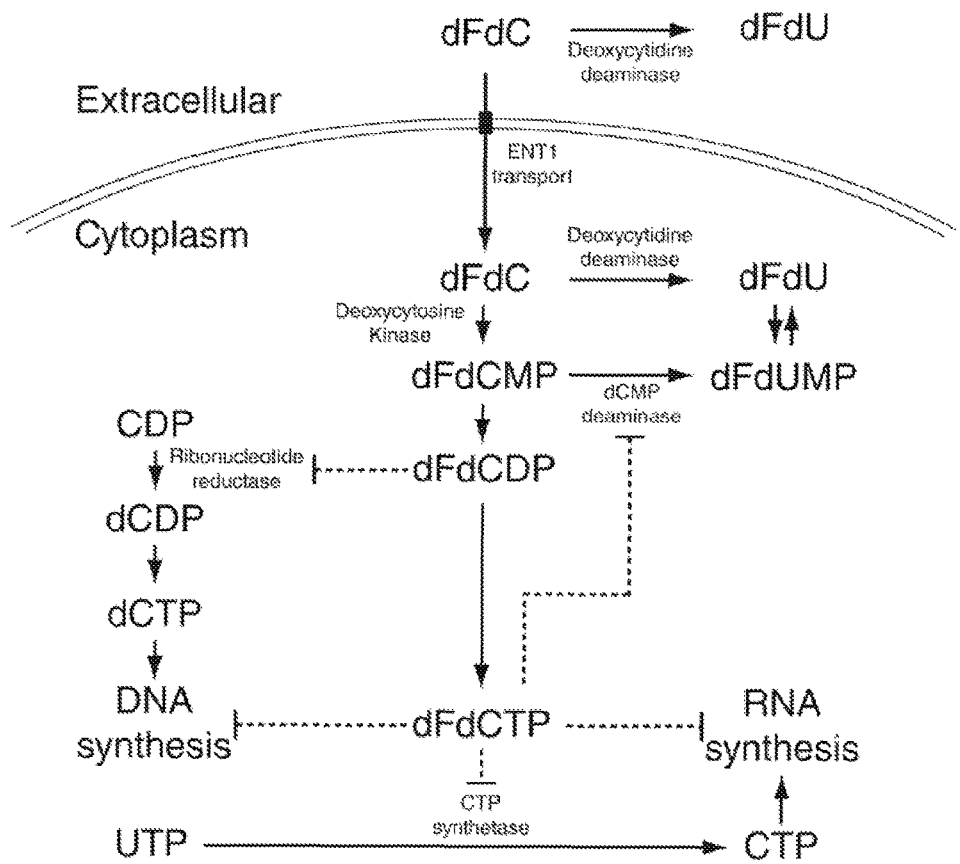
FIG. 2 shows a cellular scheme for gemcitabine activation and self-potentiation pathways. In the figure, the follow symbols or abbreviations are used: a) dashed lines represent an inhibitory effect on an enzyme; b) gemcitabine is denoted as dFdC; c) gemcitabine monophosphate is denoted as dFdCMP; d) gemcitabine diphosphate is denoted as dFdCDP; e) gemcitabine triphosphate is denoted as dFdCTP; f) deaminated gemcitabine is denoted as dFdU; and g) deaminated gemcitabine monophosphate is denoted as dFdUMP.

Again, without wishing to be bound by a particular theory, it is believed the disclosed compounds can also inhibit RNA virus replication through a second, additional mechanism. For example, gemcitabine also inhibits multiple steps within the pyrimidine biosynthesis pathway. The diphosphate form of gemcitabine (dFdCDP) inhibits ribonucleotide reductase while the triphosphate form (dFdCTP) inhibits both CTP synthetase and deoxycytidine monophosphate deaminase (FIG. 2). The inhibition of these three enzymes leads to a reduction in cellular CTP and dCTP pools, and ultimately, an increase in the molar ratio of gemcitabine to natural nucleotides within cells. This ability of gemcitabine to reduce the cellular levels of competing natural pyrimidines and thereby increase the likelihood of incorporation of dFdCTP into DNA and RNA chains is termed "self-potentiation" (Heinemann, V., et al. (1992) *Cancer Res* 52, 533-539; Plunkett, W., et al. (1995) *Semin Oncol* 22, 3-10; and Huang, P., et al. (1991) *Cancer Res* 51, 6110-6117). It is believed that the disclosed compounds can inhibit the synthesis of RNA viruses indirectly by reducing intracellular CTP pools. Detrimental to its activity, gemcitabine is rapidly deaminated by cytidine deaminase both intracellularly and in plasma to yield the inactive metabolite 2',2'-difluorodeoxyuridine (dFdU). Additionally, dFdCMP is deaminated intracellularly by deoxycytidylate deaminase to form the inactive metabolite dFdUMP. It is believed that protecting the amine group of the cytosine base of the disclosed compounds reduces inactivation of the compounds by deamination.

Interestingly, part of the current standard of care for patients diagnosed with chronic HCV is ribavirin, a nucleoside analog with broad spectrum antiviral activities. Although ribavirin has been proposed to inhibit viral replication through multiple mechanisms (Hong, Z. and Cameron, C. E. (2002) *Prog Drug Res* 59, 41-69), the predominant mechanism by which ribavirin inhibits replication of RNA viruses has been proposed to be the reduction of intracellular GTP pools through the inhibition of IMP dehydrogenase (Blackstock, A. W., et al., ibid). Importantly, the activities of ribavirin as an inhibitor of purine biosynthesis mirror the activities of gemcitabine as an inhibitor of pyrimidine biosynthesis. Therefore, gemcitabine may inhibit HCV replication through a similar molecular mechanism as ribavirin, the nucleoside analog that is currently prescribed to treat chronic HCV infections.

E. Methods of Making the Compounds

In one aspect, the invention relates to methods of making gemcitabine amide analogs, which can be useful in the treatment of cancers and hepatitis. In one aspect, the invention relates to the disclosed synthetic manipulations. In a further aspect, the disclosed compounds comprise the products of the synthetic methods described herein.

1. Synthesis

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

Thus, in one aspect, the invention relates to a method of making a compound comprising the steps of: (a) providing a first compound having a structure represented by a formula:

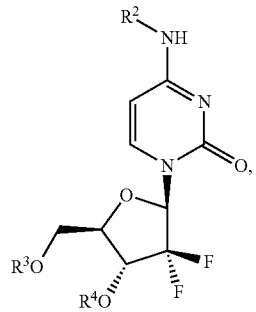

wherein $R^2$ is selected from hydrogen, C1-C4 alkyl, and amine protecting group; wherein $R^3$ is selected from hydrogen and hydroxyl protecting group; and wherein $R^4$ is selected from hydrogen, C1-C8 alkyl, and hydroxyl protecting group, or wherein $R^3$ and $R^4$ together comprise a divalent moiety having a structure represented by a formula:

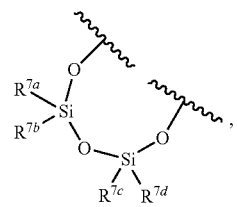

wherein each of $R^{7a}$, $R^{7b}$, $R^{7c}$, and $R^{7d}$ is independently selected from methyl, ethyl, propyl, and butyl; and (b) reacting with a second compound having a structure represented by a formula:

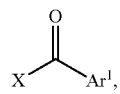

wherein X is halogen or pseudohalogen; wherein $Ar^1$ is a bicyclic fused ring system comprising an aryl ring fused to a 5-, 6-, or 7-membered heterocycloalkyl; wherein the aryl ring is selected from phenyl, pyridinyl, pyrimidinyl, pyridazinyl, pyrazinyl, and triazinyl; wherein the aryl ring is substituted with 0, 1, 2, or 3 groups independently selected from halogen, —OH, —CN, —NH$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$; wherein each R$^5$ is independently selected from hydrogen, C1-C8 alkyl, and a hydroxyl protecting group; wherein each of R$^{6a}$ and R$^{6b}$ is independently selected from hydrogen, C1-C4 alkyl, and an amine protecting group; thereby forming an amide bond.

Thus, in one aspect, the invention relates to a method of making a compound comprising the steps of: (a) providing a first compound having a structure represented by a formula:

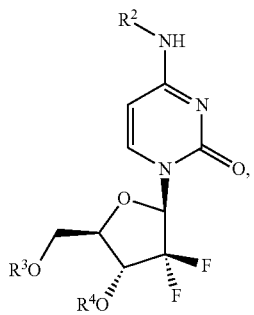

wherein R$^2$ is selected from hydrogen, C1-C4 alkyl, and amine protecting group; wherein R$^3$ is selected from hydrogen and hydroxyl protecting group; and wherein R$^4$ is selected from hydrogen, C1-C8 alkyl, and hydroxyl protecting group, or wherein R$^3$ and R$^4$ together comprise a divalent moiety having a structure represented by a formula:

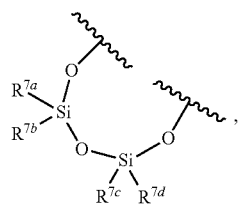

wherein each of R$^{7a}$, R$^{7b}$, R$^{7c}$, and R$^{7d}$ is independently selected from methyl, ethyl, propyl, and butyl; and (b) reacting with a second compound having a structure represented by a formula:

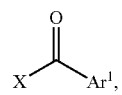

wherein X is halogen or pseudohalogen; wherein Ar$^1$ is a bicyclic fused ring system comprising an aryl ring fused to a 5-, 6-, or 7-membered heterocycloalkyl; wherein the aryl ring is selected from phenyl, pyridinyl, pyrimidinyl, pyridazinyl, pyrazinyl, and triazinyl; wherein the aryl ring is substituted with 0, 1, 2, or 3 groups independently selected from halogen, —OH, —CN, —NH$_2$, —NO$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$; wherein each R$^5$ is independently selected from hydrogen, C1-C8 alkyl, and a hydroxyl protecting group; wherein each of R$^{6a}$ and R$^{6b}$ is independently selected from hydrogen, C1-C4 alkyl, and an amine protecting group; thereby forming an amide bond.

In a further aspect, providing is conversion of R$^2$ from hydrogen to amine protecting group. In a further aspect, providing is conversion of R$^3$ from hydrogen to hydroxyl protecting group. In a further aspect, providing is conversion of R$^4$ from hydrogen to hydroxyl protecting group. In a further aspect, providing is conversion of R$^3$ and R$^4$ from hydrogen to a divalent moiety having a structure represented by a formula:

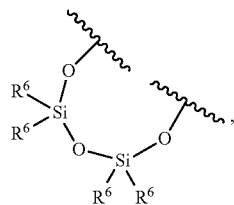

wherein each R$^6$ is independently selected from methyl, ethyl, propyl, and butyl. In a further aspect, providing is accomplished by treatment with TIPDSiCl$_2$.

In various aspects, the invention relates to a method of making a compound comprising the steps of: (a) providing a first compound having a structure represented by a formula:

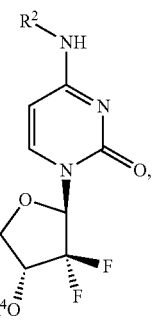

wherein R$^2$ is selected from hydrogen, C1-C4 alkyl, and amine protecting group; wherein R$^3$ is selected from hydrogen and hydroxyl protecting group; and wherein R$^4$ is selected from hydrogen, C1-C8 alkyl, and hydroxyl protecting group, or wherein R$^3$ and R$^4$ together comprise a divalent moiety having a structure represented by a formula:

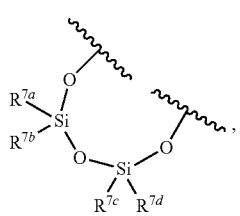

wherein each of $R^{7a}$, $R^{7b}$, $R^{7c}$, and $R^{7d}$ is independently selected from methyl, ethyl, propyl, and butyl; and (b) reacting with a second compound having a structure represented by a formula:

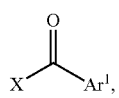

wherein X is halogen or pseudohalogen; wherein $Ar^1$ is a bicyclic fused ring system comprising an aryl ring fused to heterocycloalkyl, and wherein $Ar^1$ is selected from tetrahydronaphthalenyl, chromanyl, dihydrobenzodioxinyl, dihydrobenzooxazinyl, tetrahydroquinoxalinyl, benzodioxinyl, dihydrobenzooxathiinyl, dihydrodioxinopyridinyl, dihydrobenzooxazinyl, tetrahydroquinolinyl, and tetrahydroquinoxalinyl; wherein the aryl ring is selected from phenyl, pyridinyl, pyrimidinyl, pyridazinyl, pyrazinyl, and triazinyl; wherein the aryl ring of $Ar^1$ is substituted with 0, 1, 2, or 3 groups independently selected from halogen, —OH, —CN, —NH$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl of $Ar^1$ is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$; wherein each R$^5$ is independently selected from hydrogen, C1-C8 alkyl, and a hydroxyl protecting group; wherein each of R$^{6a}$ and R$^{6b}$ is independently selected from hydrogen, C1-C4 alkyl, and an amine protecting group; thereby forming an amide bond.

In various aspects, the invention relates to a method of making a compound comprising the steps of: (a) providing a first compound having a structure represented by a formula:

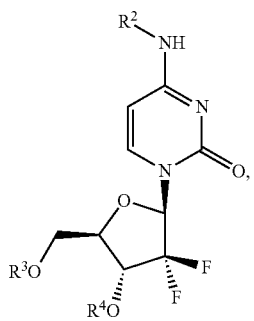

wherein R$^2$ is selected from hydrogen, C1-C4 alkyl, and amine protecting group; wherein R$^3$ is selected from hydrogen and hydroxyl protecting group; and wherein R$^4$ is selected from hydrogen, C1-C8 alkyl, and hydroxyl protecting group, or wherein R$^3$ and R$^4$ together comprise a divalent moiety having a structure represented by a formula:

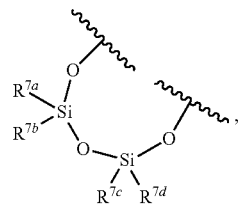

wherein each of $R^{7a}$, $R^{7b}$, $R^{7c}$, and $R^{7d}$ is independently selected from methyl, ethyl, propyl, and butyl; and (b) reacting with a second compound having a structure represented by a formula:

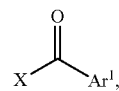

wherein X is halogen or pseudohalogen; wherein $Ar^1$ is a bicyclic fused ring system comprising an aryl ring fused to heterocycloalkyl, and wherein $Ar^1$ is selected from tetrahydronaphthalenyl, chromanyl, dihydrobenzodioxinyl, dihydrobenzooxazinyl, tetrahydroquinoxalinyl, benzodioxinyl, dihydrobenzooxathiinyl, dihydrodioxinopyridinyl, dihydrobenzooxazinyl, tetrahydroquinolinyl, and tetrahydroquinoxalinyl; wherein the aryl ring is selected from phenyl, pyridinyl, pyrimidinyl, pyridazinyl, pyrazinyl, and triazinyl; wherein the aryl ring of $Ar^1$ is substituted with 0, 1, 2, or 3 groups independently selected from halogen, —OH, —CN, —NH$_2$, —NO$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl of $Ar^1$ is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$; wherein each R$^5$ is independently selected from hydrogen, C1-C8 alkyl, and a hydroxyl protecting group; wherein each of R$^{6a}$ and R$^{6b}$ is independently selected from hydrogen, C1-C4 alkyl, and an amine protecting group; thereby forming an amide bond.

In various aspects, the invention relates to a method of making a compound comprising the steps of: (a) providing a first compound having a structure represented by a formula:

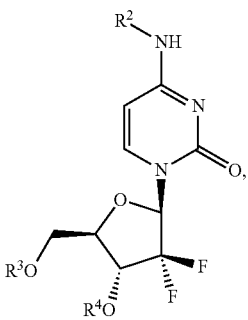

wherein $R^2$ is selected from hydrogen, C1-C4 alkyl, and amine protecting group; wherein $R^3$ is selected from hydrogen and hydroxyl protecting group; and wherein $R^4$ is selected from hydrogen, C1-C8 alkyl, and hydroxyl protecting group, or wherein $R^3$ and $R^4$ together comprise a divalent moiety having a structure represented by a formula:

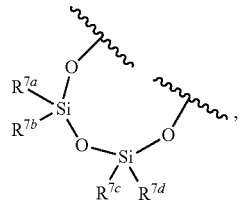

wherein each of $R^{7a}$, $R^{7b}$, $R^{7c}$, and $R^{7d}$ is independently selected from methyl, ethyl, propyl, and butyl; and (b) reacting with a second compound having a structure represented by a formula:

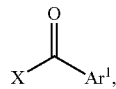

wherein X is halogen or pseudohalogen; wherein $Ar^1$ is a bicyclic fused ring system comprising an aryl ring fused to heterocycloalkyl, and wherein $Ar^1$ is selected from dihydroindenyl, dihydrobenzofuranyl, benzodioxolyl, benzooxathiolyl, dihydrobenzoxazolyl, and dioxolopyridinyl; wherein the aryl ring is selected from phenyl, pyridinyl, pyrimidinyl, pyridazinyl, pyrazinyl, and triazinyl; wherein the aryl ring of $Ar^1$ is substituted with 0, 1, 2, or 3 groups independently selected from halogen, —OH, —CN, —NH$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl of $Ar^1$ is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$; wherein each $R^5$ is independently selected from hydrogen, C1-C8 alkyl, and a hydroxyl protecting group; wherein each of $R^{6a}$ and $R^{6b}$ is independently selected from hydrogen, C1-C4 alkyl, and an amine protecting group; thereby forming an amide bond.

In various aspects, the invention relates to a method of making a compound comprising the steps of: (a) providing a first compound having a structure represented by a formula:

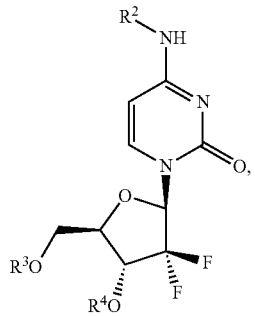

wherein $R^2$ is selected from hydrogen, C1-C4 alkyl, and amine protecting group; wherein $R^3$ is selected from hydrogen and hydroxyl protecting group; and wherein $R^4$ is selected from hydrogen, C1-C8 alkyl, and hydroxyl protecting group, or wherein $R^3$ and $R^4$ together comprise a divalent moiety having a structure represented by a formula:

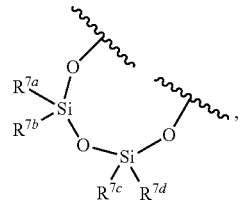

wherein each of $R^{7a}$, $R^{7b}$, $R^{7c}$, and $R^{7d}$ is independently selected from methyl, ethyl, propyl, and butyl; and (b) reacting with a second compound having a structure represented by a formula:

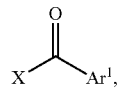

wherein X is halogen or pseudohalogen; wherein $Ar^1$ is a bicyclic fused ring system comprising an aryl ring fused to heterocycloalkyl, and wherein $Ar^1$ is selected from dihydroindenyl, dihydrobenzofuranyl, benzodioxolyl, benzooxathiolyl, dihydrobenzoxazolyl, and dioxolopyridinyl; wherein the aryl ring is selected from phenyl, pyridinyl, pyrimidinyl, pyridazinyl, pyrazinyl, and triazinyl; wherein the aryl ring of $Ar^1$ is substituted with 0, 1, 2, or 3 groups independently selected from halogen, —OH, —CN, —NH$_2$, —NO$_2$, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl of $Ar^1$ is substituted with 0, 1, 2, 3, 4, or 5 groups independently selected from halogen, —OH, —CN, —NH$_2$, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR$^5$, and —(C=O)NR$^{6a}$R$^{6b}$; wherein each $R^5$ is independently selected from hydrogen, C1-C8 alkyl, and a hydroxyl protecting group; wherein each of $R^{6a}$ and $R^{6b}$ is independently selected from hydrogen, C1-C4 alkyl, and an amine protecting group; thereby forming an amide bond.

In various aspects, the invention relates to a method of making a compound comprising the steps of: (a) providing a first compound having a structure represented by a formula:

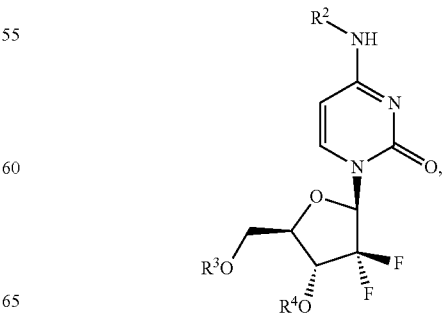

wherein R² is selected from hydrogen, C1-C4 alkyl, and amine protecting group; wherein R³ is selected from hydrogen and hydroxyl protecting group; and wherein R⁴ is selected from hydrogen, C1-C8 alkyl, and hydroxyl protecting group, or wherein R³ and R⁴ together comprise a divalent moiety having a structure represented by a formula:

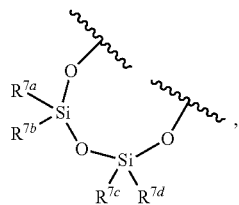

wherein each of $R^{7a}$, $R^{7b}$, $R^{7c}$, and $R^{7d}$ is independently selected from methyl, ethyl, propyl, and butyl; and (b) reacting with a second compound having a structure represented by a formula:

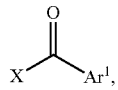

wherein X is halogen or pseudohalogen; wherein $Ar^1$ is a bicyclic fused ring system comprising an aryl ring fused to heterocycloalkyl, and wherein $Ar^1$ is selected from tetrahydrobenzoannulenyl, tetrahydrobenzooxepinyl, and dihydrobenzodioxepinyl; wherein the aryl ring is selected from phenyl, pyridinyl, pyrimidinyl, pyridazinyl, pyrazinyl, and triazinyl; wherein the aryl ring of $Ar^1$ is substituted with 0, 1, 2, or 3 groups independently selected from halogen, —OH, —CN, —NH₂, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl of $Ar^1$ is substituted with 0, 1, 2, 3, 4, or 5 groups independently selected from halogen, —OH, —CN, —NH₂, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O)OR⁵, and —(C=O)NR⁶ᵃR⁶ᵇ; wherein each R⁵ is independently selected from hydrogen, C1-C8 alkyl, and a hydroxyl protecting group; wherein each of $R^{6a}$ and $R^{6b}$ is independently selected from hydrogen, C1-C4 alkyl, and an amine protecting group; thereby forming an amide bond.

In various aspects, the invention relates to a method of making a compound comprising the steps of: (a) providing a first compound having a structure represented by a formula:

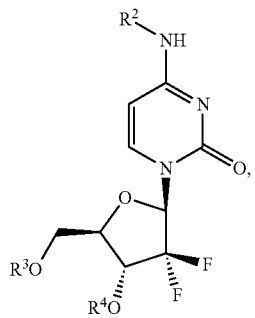

wherein R² is selected from hydrogen, C1-C4 alkyl, and amine protecting group; wherein R³ is selected from hydrogen and hydroxyl protecting group; and wherein R⁴ is selected from hydrogen, C1-C8 alkyl, and hydroxyl protecting group, or wherein R³ and R⁴ together comprise a divalent moiety having a structure represented by a formula:

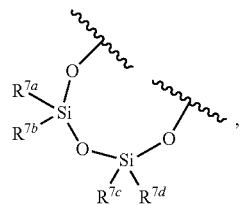

wherein each of $R^{7a}$, $R^{7b}$, $R^{7c}$, and $R^{7d}$ is independently selected from methyl, ethyl, propyl, and butyl; and (b) reacting with a second compound having a structure represented by a formula:

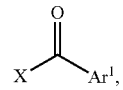

wherein X is halogen or pseudohalogen; wherein $Ar^1$ is a bicyclic fused ring system comprising an aryl ring fused to heterocycloalkyl, and wherein $Ar^1$ is selected from tetrahydrobenzoannulenyl, tetrahydrobenzooxepinyl, and dihydrobenzodioxepinyl; wherein the aryl ring is selected from phenyl, pyridinyl, pyrimidinyl, pyridazinyl, pyrazinyl, and triazinyl; wherein the aryl ring of $Ar^1$ is substituted with 0, 1, 2, or 3 groups independently selected from halogen, —OH, —CN, —NH₂, C1-C6 alkyl, C1-C6 alkoxy, C1-C6 monohaloalkyl, C1-C6 polyhaloalkyl, C1-C6 alkylamino, and C1-C6 dialkylamino; wherein the heterocycloalkyl of $Ar^1$ is substituted with 0, 1, 2, 3, 4, or 5 groups independently selected from halogen, —OH, —CN, —NH₂, —NO₂, oxo, C1-C6 alkyl, C1-C6 alkoxy, C1-C6 monohaloalkyl, C1-C6 polyhaloalkyl, C1-C6 alkylamino, C1-C6 dialkylamino, C1-C6 aminoalkyl, C1-C6 hydroxyalkyl, —(C=O) OR⁵, and —(C=O)NR⁶ᵃR⁶ᵇ; wherein each R⁵ is independently selected from hydrogen, C1-C8 alkyl, and a hydroxyl protecting group; wherein each of $R^{6a}$ and $R^{6b}$ is independently selected from hydrogen, C1-C4 alkyl, and an amine protecting group; thereby forming an amide bond.

In a further aspect, providing is conversion of R² from hydrogen to amine protecting group. In a further aspect, providing is conversion of R³ from hydrogen to hydroxyl protecting group. In a further aspect, providing is conversion of R⁴ from hydrogen to hydroxyl protecting group. In a further aspect, providing is conversion of R³ and R⁴ from hydrogen to a divalent moiety having a structure represented by a formula:

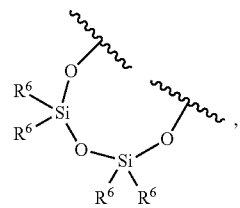

63 wherein each $R^6$ is independently selected from methyl, ethyl, propyl, and butyl. In a further aspect, providing is accomplished by treatment with $TIPDSiCl_2$.

In a further aspect, the method further comprises the step of deprotecting $R^2$. In a further aspect, the method further comprises the step of deprotecting $R^3$. In a further aspect, the method further comprises the step of deprotecting $R^4$.

In a further aspect, the invention pertains to a product of a disclosed method of making.

a. Synthesis Scheme 1

In one aspect, substituted gemcitabine aryl amide analogs of the present invention can be prepared generically by the synthetic scheme as shown in Scheme 1a, below.

64

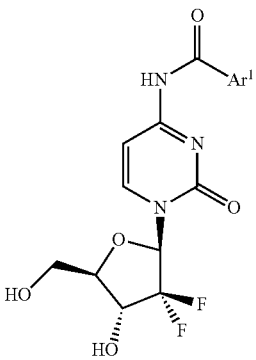

Compounds are represented in generic form, with substituents as noted in compound descriptions elsewhere herein. A more specific example is set forth below, which is discussed in further detail in Synthesis Schemes 2-4.

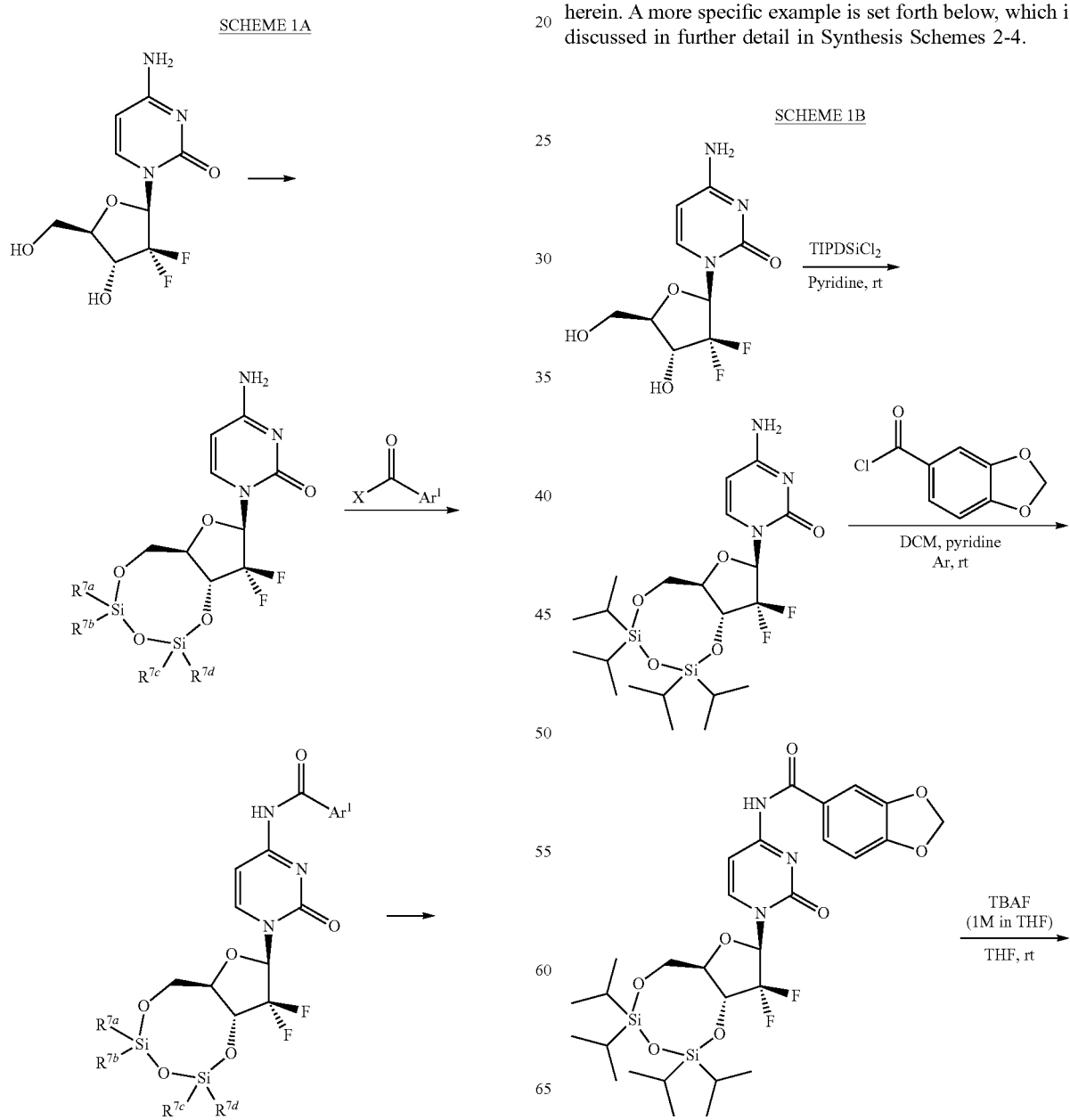

-continued

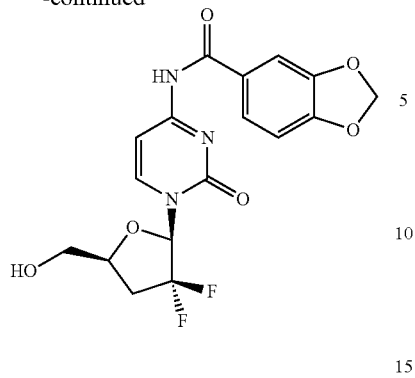

b. Synthesis Scheme 2

In one aspect, the first step in the synthesis sequence involves protection of the hydroxyl groups as shown generically in Scheme 2a, below.

SCHEME 2A

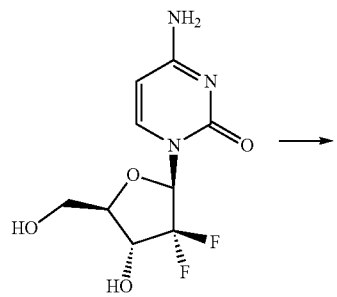

Compounds are represented in generic form, with substituents as noted in compound descriptions elsewhere herein. A more specific example of a protected gemcitabine can be prepared as shown in Scheme 2B, below.

SCHEME 2B

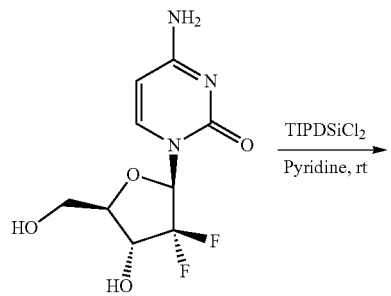

-continued

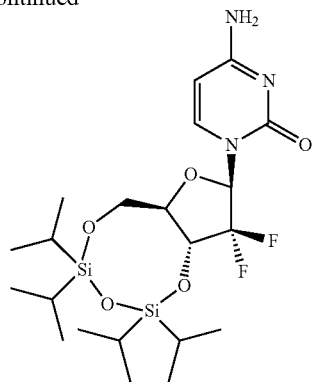

As shown above, gemcitabine (4-amino-1-((2R,4R,5R)-3,3-difluoro-4-hydroxy-5-(hydroxymethyl)tetrahydrofuran-2-yl)pyrimidin-2(1H)-one) can be treated with 1,3-dichloro-1,1,3,3-tetraisopropyldisiloxane (TIPDSiCl$_2$) in dry pyridine to provide 4-amino-1-((6aR,8R,9aR)-9,9-difluoro-2,2,4,4-tetraisopropyltetrahydro-6H-furo[3,2-f][1,3,5,2,4]trioxadisilocin-8-yl)pyrimidin-2(1H)-one. It is contemplated that other 1,3-dihalo-1,1,3,3-tetraalkyldisiloxanes can be used in place of TIPDSiCl$_2$. It is also contemplated that two monofunctional halosiloxane protecting groups can be used in place of the difunctional TIPDSiCl$_2$. Further, it is also contemplated that other hydroxyl protecting groups (e.g., tetrahydropyranyl (THP) or acetyl (Ac)) can be used in place of TIPDSiCl$_2$.

c. Synthesis Scheme 3

In a further aspect, the second step in the synthesis sequence involves formation of an amide moiety, as shown in Scheme 3A, below.

SCHEME 3A

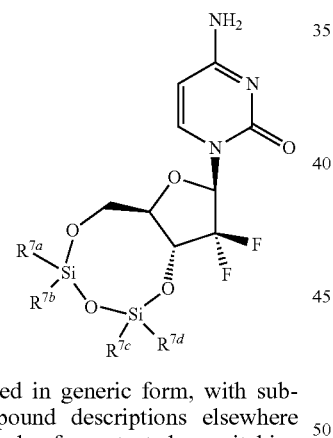

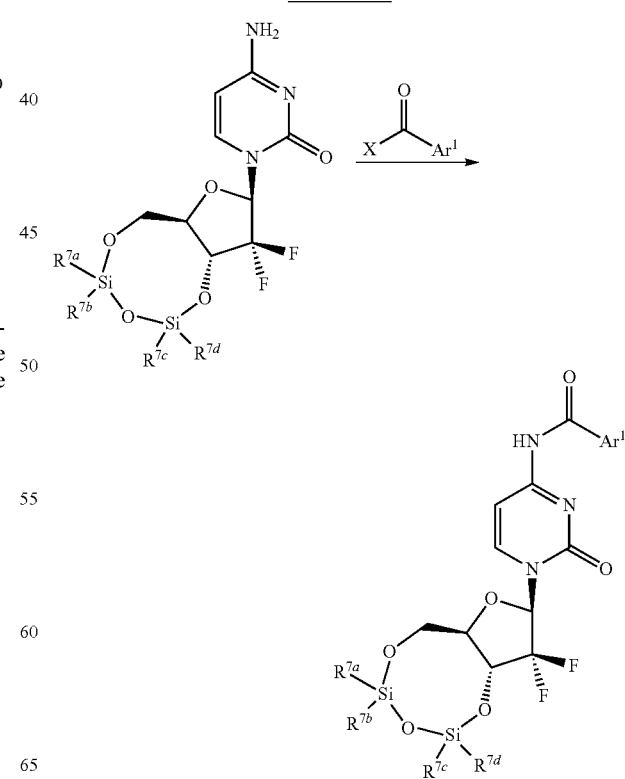

Compounds are represented in generic form, with substituents as noted in compound descriptions elsewhere herein. A more specific example of a protected substituted gemcitabine aryl amide analog can be prepared as shown in Scheme 3B, below.

SCHEME 3B

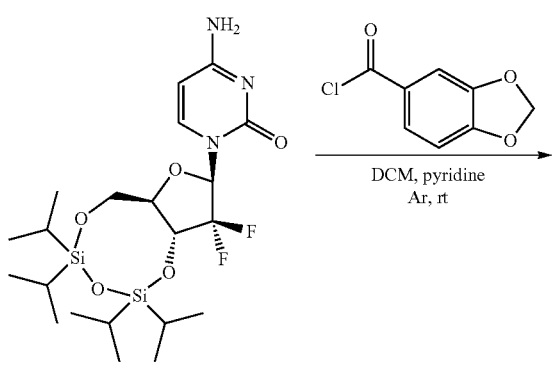

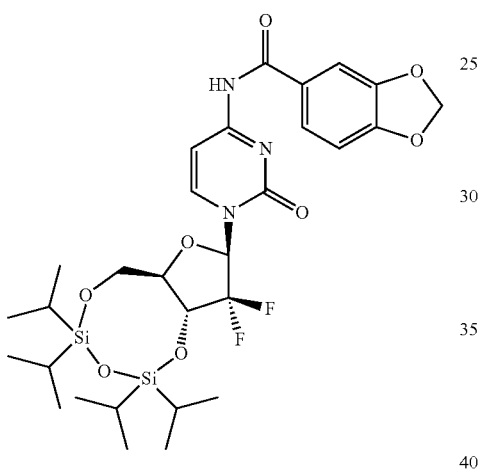

As shown above, a protected substituted gemcitabine aryl amide analog (here, 4-amino-1-((6aR,8R,9aR)-9,9-difluoro-2,2,4,4-tetraisopropyltetrahydro-6H-furo[3,2-f][1,3,5,2,4]trioxadisilocin-8-yl)pyrimidin-2(1H)-one) can be treated with an appropriate acyl halide (here, benzo[d][1,3]dioxole-5-carbonyl chloride) to form an amide bond, thereby providing N-(1-((6aR,8R,9aR)-9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-yl)benzo[d][1,3]dioxole-5-carboxamide. It is contemplated that other activated carboxyl compounds (e.g., a benzoyl bromide or anhydride) can be used in place of the benzoyl chloride. It is also contemplated that the corresponding carboxyl acid can be used to firm the amide directly with appropriate peptide coupling reagents. Further, it is also contemplated that the product of this transformation can, if desired, be carried into the next step without isolation and/or with minimal or no purification.

d. Synthesis Scheme 4

In one aspect, the first step in the synthesis sequence involves deprotection of the hydroxyl groups as shown generically in Scheme 4A, below.

SCHEME 4A

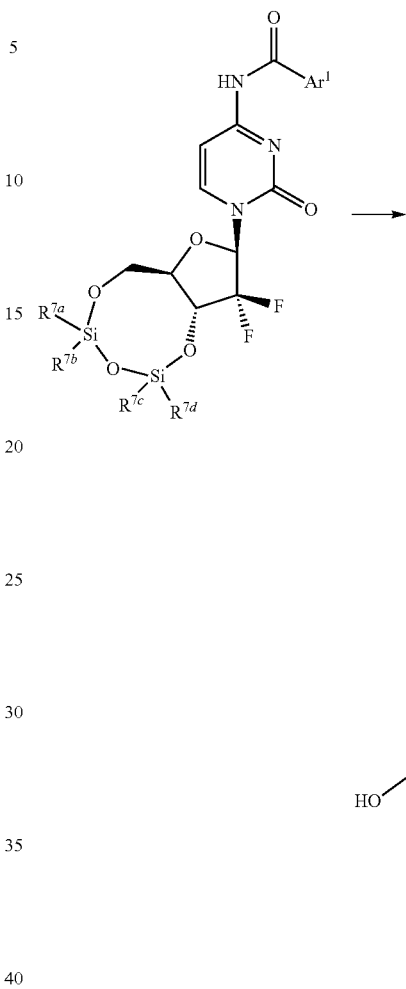

Compounds are represented in generic form, with substituents as noted in compound descriptions elsewhere herein. A more specific example of a deprotected substituted gemcitabine aryl amide analog can be prepared as shown in Scheme 4B, below.

SCHEME 4B

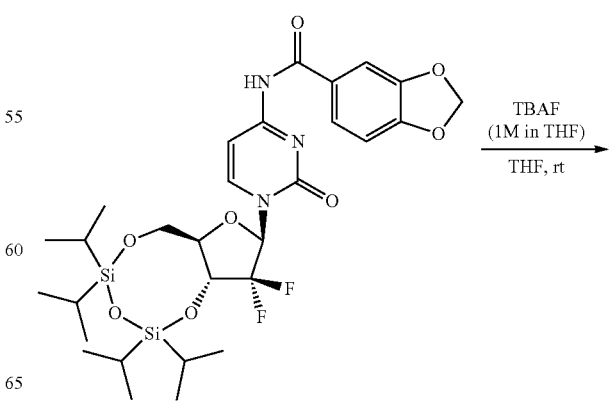

69

-continued

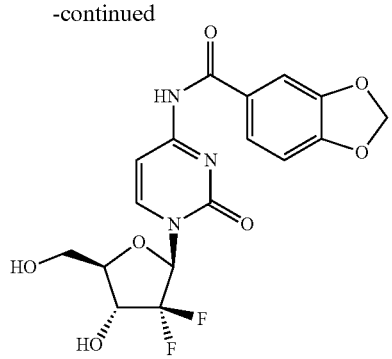

As shown above, a protected substituted gemcitabine amide analog (here, N-(1-((6aR,8R,9aR)-9,9-difluoro-2,2,4,4-tetraisopropyltetrahydro-6H-furo[3,2-f][1,3,5,2,4]trioxa-disilocin-8-yl)-2-oxo-1,2-dihydropyrimidin-4-yl)benzo[d][1,3]dioxole-5-carboxamide)) can be treated with tetrabutylammonium fluoride (TBAF) to deprotect the hydroxyl groups. Deprotection provides the corresponding deprotected substituted gemcitabine aryl amide analog (here, N-(1-((2R,4R,5R)-3,3-difluoro-4-hydroxy-5-(hydroxymethyl)tetrahydrofuran-2-yl)-2-oxo-1,2-dihydropyrimidin-4-yl)benzo[d][1,3]dioxole-5-carboxamide). It is contemplated that other sources of fluoride ion can be used in place of the TBAF. It is also contemplated that deprotection of the silyl groups can be accomplished with acid. Further, it is also contemplated that other reagents (e.g., acid or base) can be used to liberate the hydroxyl groups when other protecting groups (e.g., tetrahydropyranyl (THP) or acetyl (Ac)) have been employed.

e. Synthesis Scheme 5

In one aspect, acyl halide derivatives of Ar¹ with protected hydroxyl moieties can be prepared by generalized scheme shown below.

SCHEME 5A

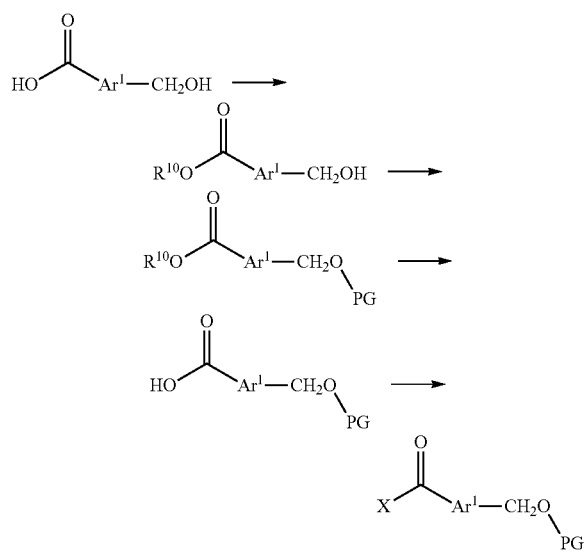

PG: protecting group
R¹⁰: C1-C4 alkyl
X: halogen

70

Compounds are represented in generic form, with substituents as noted in compound descriptions elsewhere herein. A more specific example is set forth below.

SCHEME 5B

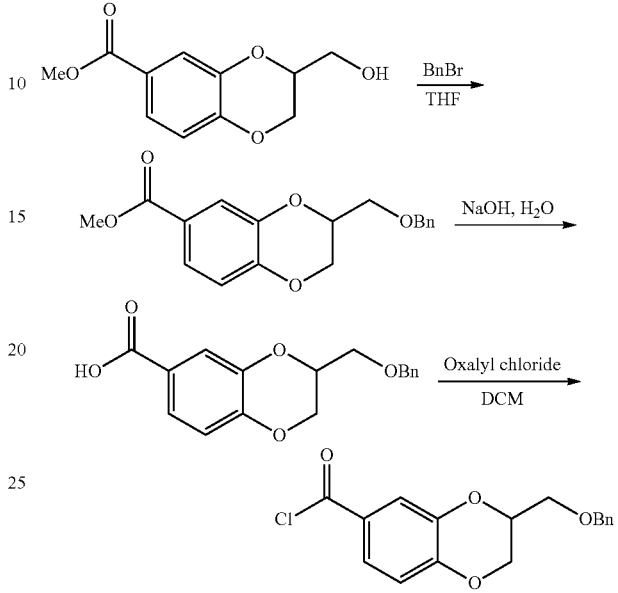

As shown above, an acyl halide derivatives of Ar¹ with protected hydroxyl moieties, e.g. a compound such as that shown above, 3-((benzyloxy)methyl)-2,3-dihydrobenzo[b][1,4]dioxine-6-carbonyl chloride, can be prepared begin with a suitable ester analogue, in this case methyl 3-(hydroxymethyl)-2,3-dihydrobenzo[b][1,4]dioxine-6-carboxylate. The ester derivative can be prepared from the corresponding acid by methods known to one skilled in the art. The ester is treated with a suitable reagent to provide a suitable protecting group. As shown above, bromomethylbenzene is used to provide a benzyl protecting group at the hydroxyl moiety to yield methyl 3-((benzyloxy)methyl)-2,3-dihydrobenzo[b][1,4]dioxine-6-carboxylate. The ester is removed to provide the corresponding carboxylic acid used standard techniques, e.g. aqueous base such as NaOH, to provide 3-((benzyloxy)methyl)-2,3-dihydrobenzo[b][1,4]dioxine-6-carboxylic acid. The desired corresponding acyl halide is prepared from the carboxylic acid using any one of a variety of reagents, the specific reagent used being determined by desired halide moiety, other substituent groups, and reaction conditions desired in subsequent reactions. For example, thionyl chloride, oxalyl chloride (as shown above), or phosphorus pentachloride can be used to prepare acyl chlorides; phosphorus pentabromide can be used to prepare suitable acyl bromides; and cyanuric fluoride can be used to prepare suitable acyl fluorides. In the reaction above, treatment of 3-((benzyloxy)methyl)-2,3-dihydrobenzo[b][1,4]dioxine-6-carboxylic acid with oxalyl chloride in a suitable solvent, e.g. DCM, provides the desired acyl halide, 3-((benzyloxy)methyl)-2,3-dihydrobenzo[b][1,4]dioxine-6-carbonyl chloride.

f. Synthesis Scheme 6

In one aspect, substituted gemcitabine aryl amide analogs comprising an Ar¹ moiety with ester and amide groups can be prepared by generalized scheme shown below.

SCHEME 6A
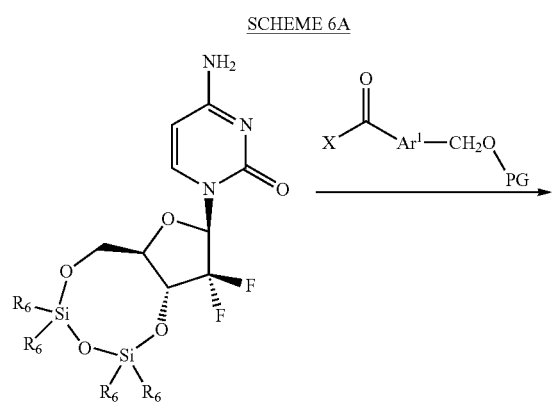
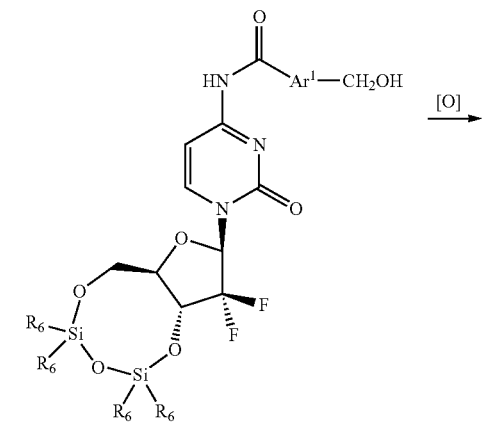
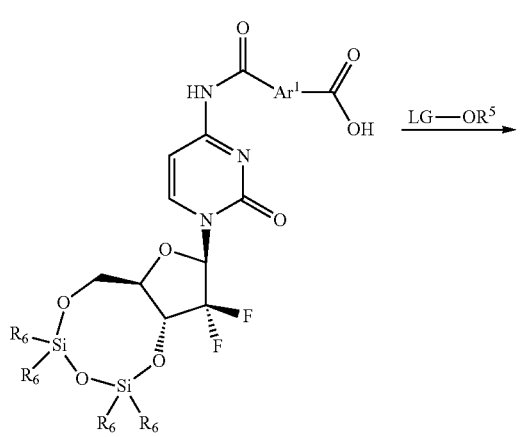
SCHEME 6B
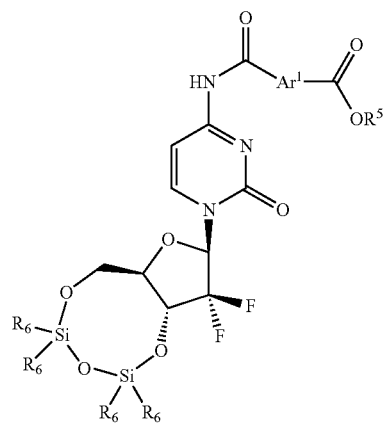
[O]: oxidant, e.g. KMnO₄
LG: Leaving group
PG: Protecting group
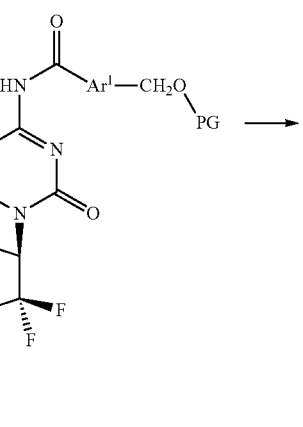

73
-continued
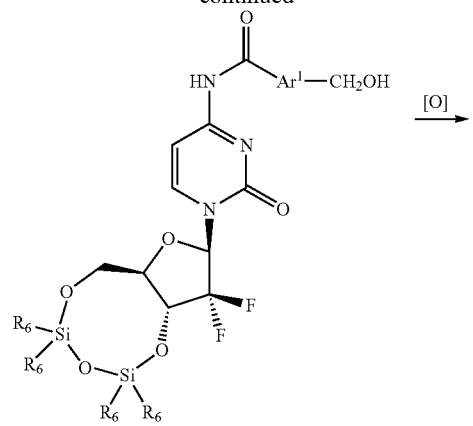
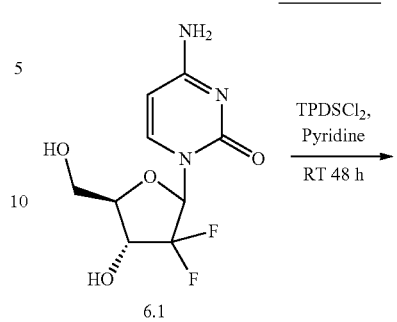
[O]: oxidant, e.g. KMnO₄
PG: Protecting group
Compounds are represented in generic form, with substituents as noted in compound descriptions elsewhere herein. More specific examples are set forth below.
74
SCHEME 6C
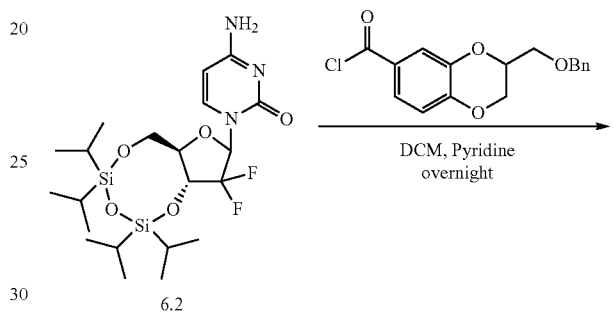
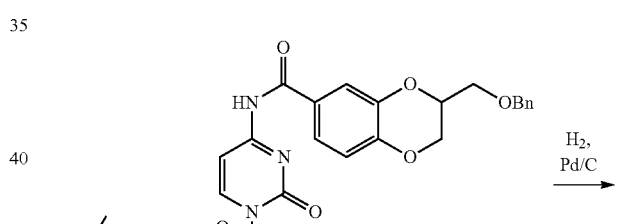
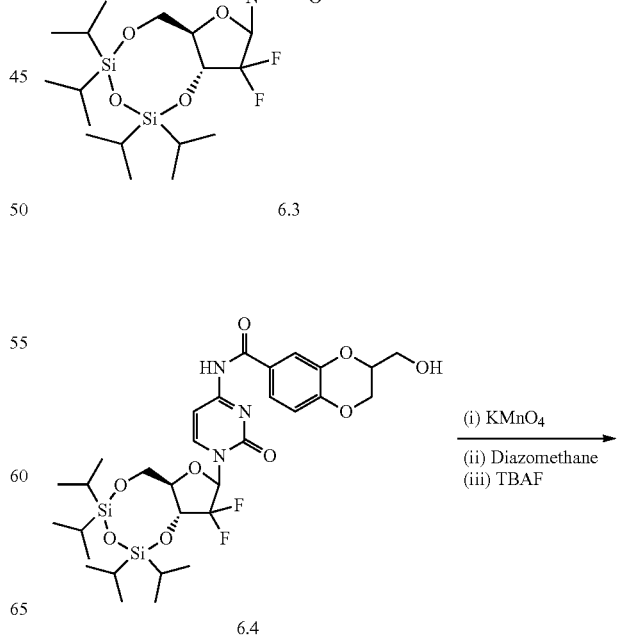

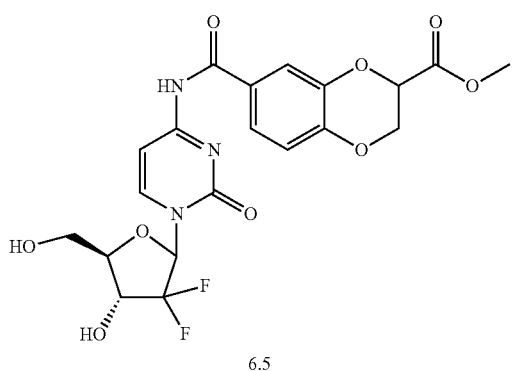 [SMILES: COC(=O)C1COc2ccc(C(=O)Nc3ccn(C4O[C@H](CO)[C@@H](O)C4(F)F)c(=O)n3)cc2O1]

6.5

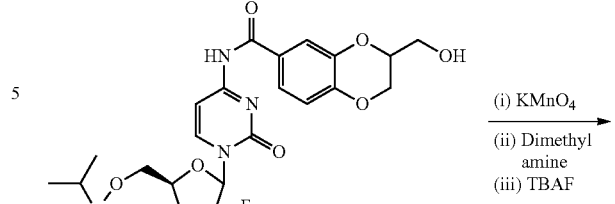

(i) KMnO₄
(ii) Dimethyl amine
(iii) TBAF 6.4

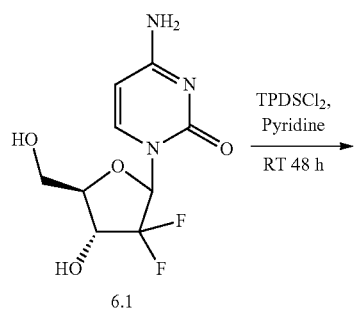

6.6

SCHEME 6D

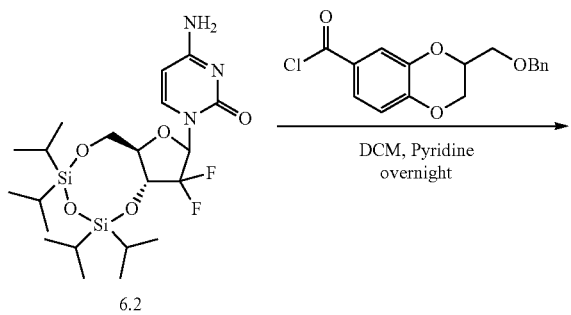

TPDSCl₂, Pyridine

RT 48 h 6.1

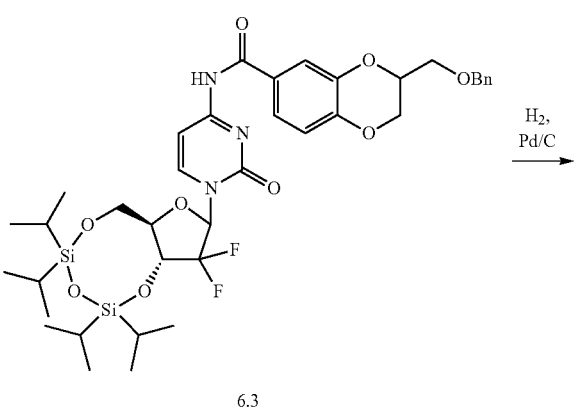

6.2

DCM, Pyridine overnight

H₂, Pd/C 6.3

As shown above, the initial steps (e.g. compound 6.1 through to compound 6.3) use conditions generally as described in the reaction schemes discussed herein above. difference is the use of an acyl halide derivative of Ar¹ with one or more protected hydroxyl moieties, prepared using methods described in Synthesis Scheme 5 above. The hydroxy moiety is deprotected (i.e. to prepare compound 6.4 from compound 6.3) using deprotection conditions appropriate to the particular protecting group used. As shown in the specific examples above, the benzyl group is removed in the presence of hydrogen and Pd/C. The compound thus prepared, i.e. an Ar¹ group with one or more free hydroxy groups, can be further derivatized to either a suitable ester or amide moiety (i.e. conversion of compound 6.4 to compound 6.5 and conversion of compound 6.4 to compound 6.6, respectively). As shown above, oxidation in the presence of KMnO₄ is used to convert the alcohol initial to the corresponding carboxylic acid. Other oxidation conditions can be used depending upon the presence what other substituent groups are present on the Ar¹ moiety. The carboxylic acid is the used to prepare the desired ester or amide as shown above. For example, the methyl ester can be prepared by initial reaction of the carboxylic acid with diazomethane, followed by treatment with tetra-n-butylammonium fluoride ("TBAF"). Esterification can also be carried out by other suitable methods as determined by one skilled in the art. Alternatively, following oxidation of the alcohol to the corresponding carboxylic acid, e.g. oxidation in the presence of KMnO₄ as shown above, a suitable amide can be prepared by reaction with a suitable amine, followed by treatment with TBAF.

g. Synthesis Scheme 7

In one aspect, acyl halide derivatives of Ar¹ can be prepared by generalized scheme shown below.

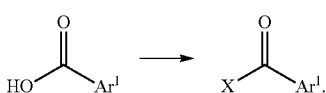

Compounds are represented in generic form, with substituents as noted in compound descriptions elsewhere herein. More specific examples are set forth below.

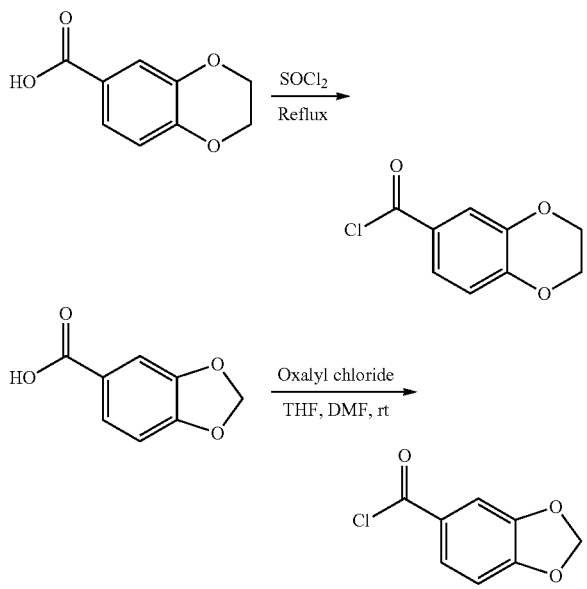

As shown above, and as described in part above, suitable acyl halides, e.g. acyl halide derivatives of Ar¹ (i.e. bicyclic fused ring system comprising an aryl ring fused to a 5-, 6-, or 7-membered heterocycloalkyl) can be prepared from the corresponding carboxylic acids. Such carboxylic acids can be obtained commercially, or prepared by oxidation of suitable alcohols, aldehydes, and alkenes derivatives of Ar¹, such compounds are generally commercially available. Once the appropriate carboxylic acid is available, whether it is obtained commercially or by oxidation of the precursor alcohol, aldehyde, or alkene, it can be used to prepare the appropriate acyl halide. As shown above, it is possible to use either thienyl chloride or oxalyl chloride to provide the corresponding acyl chloride by reaction at a suitable temperature (e.g. reflux or room temperature as shown). As already discussed, acyl halides can be prepared by alternative methods. For example, phosphorus pentachloride can be used to prepare acyl chlorides; phosphorus pentabromide can be used to prepare suitable acyl bromides; and cyanuric fluoride can be used to prepare suitable acyl fluorides.

2. Chiral Resolution

The disclosed methods of making can provide compounds that can contain one or more asymmetric centers and, thus, potentially give rise to enantiomers and diastereomers. Unless stated to the contrary, the compounds prepared by the disclosed methods include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

In one aspect, the disclosed methods of making can provide racemic or scalemic mixtures that can be resolved to pure or substantially pure enantiomers using chiral phase chromatography or other suitable methods known to one skilled in the art. As known to one skilled in the art, a variety specific columns and/or mobile phases can affect the desired resolution of enantiomers, and the specific choice can be determined by one skilled in the art. As known to one skilled in the art, chiral chromatography can be carried out in a variety of formats (e.g. SFC, HPLC, and SMB), and other formats can be used to obtain similar results. Moreover, other suitable methods known to one skilled in the art for the separation and isolation of individual enantiomers from a racemic or scalemic mixture can be used to isolate specific enantiomers as needed.

F. Pharmaceutical Compositions

In one aspect, the invention relates to pharmaceutical compositions comprising the disclosed compounds and products of disclosed methods. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In a further aspect, the effective amount is a therapeutically effective amount. In a still further aspect, the effective amount is a prophylactically effective amount. In a still further aspect, the pharmaceutical composition comprises a compound that is a product of a disclosed method of making.

In one aspect, the pharmaceutical composition is used to treat a mammal. In a yet further aspect, the mammal is a human. In a further aspect, the mammal has been diagnosed with a need for treatment of the disorder prior to the administering step. In a further aspect, the mammal has been identified to be in need of treatment of the disorder. In a further aspect, the pharmaceutical composition is used to treat a neurological and/or psychiatric disorder. In a yet further aspect, the disorder is a cancer. In a yet further aspect, the disorder is a hepatitis.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

Thus, in one aspect, the invention relates to a pharmaceutical composition comprising a pharmaceutically acceptable carrier and an effective amount of a disclosed compound or the product of a disclosed method. In a further aspect, the composition further comprises one or more of: (a) a drug known to treat a disorder of uncontrolled cellular proliferation; (b) a substance known to increase risk of uncontrolled cellular proliferation; (c) an antiviral agent; and (d) a substance known to increase risk of viral infection. In a further aspect, the composition further comprises carboplatin.

In various further aspects, the pharmaceutical composition comprises a compound having an $IC_{50}$ less than about 500 nM when determined using an HCV luciferase replicon cell-line in a luciferase assay. It is understood that the compound of the pharmaceutical composition comprises a disclosed compound and a compound that is a product of a disclosed method of making. In a further aspect, the pharmaceutical composition comprises a compound having an $IC_{50}$ less than about 250 nM when determined using an HCV luciferase replicon cell-line in a luciferase assay. In a still further aspect, the pharmaceutical composition comprises a compound having an $IC_{50}$ less than about 150 nM when determined using an HCV luciferase replicon cell-line in a luciferase assay. In a yet further aspect, the pharmaceutical composition comprises a compound having an $IC_{50}$ less than about 75 nM when determined using an HCV luciferase replicon cell-line in a luciferase assay.

In a further aspect, the pharmaceutical composition comprises a compound having a $TC_{50}$ greater than about 100 μM when determined using the Huh7 cell-line in an MTS cell viability assay. In a still further aspect, the pharmaceutical composition comprises a compound having a $TC_{50}$ greater than about 200 μM when determined using the Huh7 cell-line in an MTS cell viability assay. In a yet further aspect, the pharmaceutical composition comprises a compound having a $TC_{50}$ greater than about 400 μM when determined using the Huh7 cell-line in an MTS cell viability assay. In an even further aspect, the pharmaceutical composition comprises a compound having a $TC_{50}$ greater than about 800 μM when determined using the Huh7 cell-line in an MTS cell viability assay.

In a further aspect, the pharmaceutical composition comprises a compound having a therapeutic index ($TC_{50}/IC_{50}$) greater than about 1000. In a still further aspect, the pharmaceutical composition comprises a compound having a therapeutic index ($TC_{50}/IC_{50}$) greater than about 2500. In a yet further aspect, the pharmaceutical composition comprises a compound having a therapeutic index ($TC_{50}/IC_{50}$) greater than about 5000. In an even further aspect, the pharmaceutical composition comprises a compound having a therapeutic index ($TC_{50}/IC_{50}$) greater than about 7500.

It is understood that the disclosed compositions can be prepared from the disclosed compounds. It is also understood that the disclosed compositions can be employed in the disclosed methods of using.

G. Methods of Using the Compounds and Compositions

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders, including, for example, viral disorders (e.g., hepatitis) and disorders of uncontrolled cellular proliferation (e.g., cancers).

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

a. Treating a Subject for Viral Infection

In one aspect, the invention relates to a method for treating a subject for viral infection, the method comprising the step of administering to the subject an effective amount of a disclosed compound or a product of a disclosed method or a disclosed pharmaceutical composition. In one aspect, the amount is therapeutically effective. In a further aspect, the amount is prophylactically effective.

In one aspect, the subject is a mammal. In a further aspect, the mammal is a human. In a further aspect, the mammal has been diagnosed with a need for treatment of the infection prior to the administering step. In a further aspect, the method further comprises the step of identifying a mammal in need of treatment of the infection.

In a further aspect, the viral infection is viral hepatitis. In a further aspect, the viral infection is Hepatitis A, Hepatitis B, or Hepatitis C. In a further aspect, the viral infection is dengue virus, Human immunodeficiency virus, Herpes simplex, Cytomegalovirus, Epstein-Barr virus, yellow fever, or tick-borne encephalitis.

In various further aspects, a disclosed compound or a product of a disclosed method has an $IC_{50}$ less than about 500 nM when determined using an HCV luciferase replicon cell-line in a luciferase assay. It is understood that a compound refers to either a disclosed compound or a compound that is a product of a disclosed method of making. In a further aspect, a disclosed compound or a product of a disclosed method has an $IC_{50}$ less than about 250 nM when determined using an HCV luciferase replicon cell-line in a luciferase assay. In a still further aspect, a disclosed compound or a product of a disclosed method has an $IC_{50}$ less than about 150 nM when determined using an HCV luciferase replicon cell-line in a luciferase assay. In a yet further aspect, a disclosed compound or a product of a disclosed method has an $IC_{50}$ less than about 75 nM when determined using an HCV luciferase replicon cell-line in a luciferase assay.

In a further aspect, a disclosed compound or a product of a disclosed method has a $TC_{50}$ greater than about 100 μM when determined using the Huh7 cell-line in an MTS cell viability assay. In a still further aspect, a disclosed compound or a product of a disclosed method has a $TC_{50}$ greater than about 200 μM when determined using the Huh7 cell-line in an MTS cell viability assay. In a yet further aspect, a disclosed compound or a product of a disclosed method has a $TC_{50}$ greater than about 400 μM when determined using the Huh7 cell-line in an MTS cell viability assay. In an even further aspect, a disclosed compound or a product of a disclosed method has a TC$_{50}$ greater than about 800 µM when determined using the Huh7 cell-line in an MTS cell viability assay.

In a further aspect, a disclosed compound or a product of a disclosed method has a therapeutic index (TC$_{50}$/IC$_{50}$) greater than about 1000. In a still further aspect, a disclosed compound or a product of a disclosed method has a therapeutic index (TC$_{50}$/IC$_{50}$) greater than about 2500. In a yet further aspect, a disclosed compound or a product of a disclosed method has a therapeutic index (TC$_{50}$/IC$_{50}$) greater than about 5000. In an even further aspect, a disclosed compound or a product of a disclosed method has a therapeutic index (TC$_{50}$/IC$_{50}$) greater than about 7500.

b. Inhibiting Viral Replication

In one aspect, the invention relates to a method for inhibiting viral replication within at least one cell, the method comprising the step of administering to the cell an effective amount of a disclosed compound or the product of a disclosed method or a disclosed pharmaceutical composition. In one aspect, the cell is a mammalian. In a further aspect, the cell is a human cell. In a further aspect, administration to the cell is performed in vitro. In a further aspect, administration to the cell is performed in vivo.

In a further aspect, the viral infection is viral hepatitis. In a further aspect, the viral infection is hepatitis A, hepatitis B, or hepatitis C. In a further aspect, the viral infection is dengue virus, human immunodeficiency virus, herpes simplex, cytomegalovirus, Epstein-Barr virus, yellow fever, or tick-borne encephalitis.

c. Treating a Disorder of Uncontrolled Cellular Proliferation

In one aspect, the invention relates to a method for treating a disorder of uncontrolled cellular proliferation, the method comprising administering to a subject an effective amount of a disclosed compound or the product of a disclosed method or a disclosed pharmaceutical composition. In one aspect, the amount is therapeutically effective. In a further aspect, the amount is prophylactically effective.

In one aspect, the subject is a mammal. In a further aspect, the mammal is a human. In a further aspect, the mammal has been diagnosed with a need for treatment of the disorder prior to the administering step. In a further aspect, the method further comprises the step of identifying a mammal in need of treatment of the disorder.

In a further aspect, the disorder is cancer. In a further aspect, the disorder is carcinoma. In a further aspect, the disorder is selected from non-small cell lung cancer, pancreatic cancer, bladder cancer, liver cancer, and breast cancer. In a further aspect, the disorder is esophageal cancer. In a further aspect, the disorder is lymphoma.

d. Arresting Tumor Growth

In one aspect, the invention relates to a method for arresting tumor growth, the method comprising administering to at least one tumor cell an effective amount of a disclosed compound or the product of a disclosed method or a disclosed pharmaceutical composition. In one aspect, the cell is a mammalian. In a further aspect, the cell is a human. In a further aspect, administration to the cell is performed in vitro. In a further aspect, administration to the cell is performed in vivo.

In a further aspect, the disorder is cancer. In a further aspect, the disorder is carcinoma. In a further aspect, the disorder is selected from non-small cell lung cancer, pancreatic cancer, bladder cancer, liver cancer, and breast cancer. In a further aspect, the disorder is esophageal cancer. In a further aspect, the disorder is lymphoma.

2. Manufacture of a Medicament

In one aspect, the invention relates to a medicament comprising one or more disclosed compounds; or a pharmaceutically acceptable salt, hydrate, solvate, or polymorph thereof. In a further aspect, the one or more compounds is a product of a disclosed method of making.

Thus, in a further aspect, the invention relates to a method for manufacturing a medicament, the method comprising combining a pharmaceutically acceptable carrier with a disclosed compound or the product of a disclosed method or a disclosed pharmaceutical composition.

It is understood that the disclosed methods can be performed with the disclosed compounds, products, and pharmaceutical compositions. It is also understood that the disclosed methods can be employed in connection with the disclosed methods of using.

3. Use of Compounds

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In a further aspect, the use is associated with the treatment of viral infection (e.g., hepatitis) or disorder of uncontrolled cellular proliferation (e.g., cancer).

It is understood that the disclosed uses can be employed in connection with the disclosed compounds, products of disclosed methods of making, methods, compositions, and kits.

4. Kits

In one aspect, the invention relates to kits comprising at least one disclosed compound; or a pharmaceutically acceptable salt, hydrate, solvate, or polymorph thereof, at least one product of a disclosed method, or at least one disclosed pharmaceutical composition and one or more of:

(a) an antiviral agent;
(b) a substance known to increase risk of viral infection;
(c) instructions for treating a viral infection;
(d) a drug known to treat a disorder of uncontrolled cellular proliferation;

(e) a substance known to increase risk of uncontrolled cellular proliferation; and (f) instructions for treating a disorder of uncontrolled cellular proliferation.

In a further aspect, the at least one compound and the at least one agent are co-formulated. In a still further aspect, the at least one compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

In a further aspect, the drug known to treat a disorder of uncontrolled cellular proliferation is carboplatin.

In various further aspects, the at least one compound of the kit has an $IC_{50}$ less than about 500 nM when determined using an HCV luciferase replicon cell-line in a luciferase assay. It is understood that the at least one compound comprises a disclosed compound and a compound that is a product of a disclosed method of making. In a further aspect, the at least one compound of the kit has an $IC_{50}$ less than about 250 nM when determined using an HCV luciferase replicon cell-line in a luciferase assay. In a still further aspect, the at least one compound of the kit has an $IC_{50}$ less than about 150 nM when determined using an HCV luciferase replicon cell-line in a luciferase assay. In a yet further aspect, the at least one compound of the kit has an $IC_{50}$ less than about 75 nM when determined using an HCV luciferase replicon cell-line in a luciferase assay.

In a further aspect, the at least one compound of the kit has a $TC_{50}$ greater than about 100 µM when determined using the Huh7 cell-line in an MTS cell viability assay. In a still further aspect, the at least one compound of the kit has a $TC_{50}$ greater than about 200 µM when determined using the Huh7 cell-line in an MTS cell viability assay. In a yet further aspect, the at least one compound of the kit has a $TC_{50}$ greater than about 400 µM when determined using the Huh7 cell-line in an MTS cell viability assay. In an even further aspect, the at least one compound of the kit has a $TC_{50}$ greater than about 800 µM when determined using the Huh7 cell-line in an MTS cell viability assay.

In a further aspect, the at least one compound of the kit has a therapeutic index ($TC_{50}/IC_{50}$) greater than about 1000. In a still further aspect, the at least one compound of the kit has a therapeutic index ($TC_{50}/IC_{50}$) greater than about 2500. In a yet further aspect, the at least one compound of the kit has a therapeutic index ($TC_{50}/IC_{50}$) greater than about 5000. In an even further aspect, the at least one compound of the kit has a therapeutic index ($TC_{50}/IC_{50}$) greater than about 7500.

It is understood that the disclosed kits can be prepared from the disclosed compounds, products, and pharmaceutical compositions. It is also understood that the disclosed kits can be employed in connection with the disclosed methods of using.

H. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. General Methods

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

All solvents were dried with solvent-purification system (Innovative Technology, Inc). Analytical TLC was carried out on E. Merck silica gel 60 F254 aluminum-backed plates. The preparation TLC was carried out on silica gel 60 F254 plates (20×20 cm, 1 mm) from EMD Chemicals, Inc. The 230-400 mesh size of the absorbent was utilized for all chromatographic purifications. $^1$H NMR and high-resolution mass spectra were obtained at The Ohio State University Campus Chemical Instrumentation Center.

2. Synthetic Procedures a. Preparation of 2,3-dihydrobenzo[b][1,4]dioxine-6-carbonyl chloride

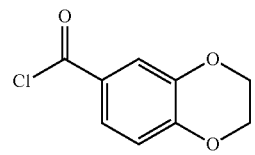 [SMILES: O=C(Cl)c1ccc2c(c1)OCCO2]

In a round bottom flask, 1,4-Benzodioxane-6-carboxylic acid (1.00 g, 0.5.55 mmol) and thionyl chloride (6.04 mL, 83.33 mmol) was mixed together and refluxed for 2 h. The reaction was concentrated in vacuo, then 25 mL of toluene was added to the residue, and the slurry was concentrated again to obtain the title product 6 as a solid (0.77 g, 70%).

b. Preparation of benzo[d][1,3]dioxole-5-carbonyl chloride

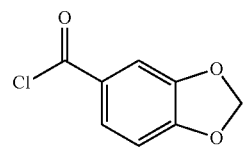 [SMILES: O=C(Cl)c1ccc2c(c1)OCO2]

To a stirred solution of piperonylic acid (1.00 g, 6.02 mmol) in THF was added oxalic acid (0.765 mL, 9.03 mmol) and DMF (0.5 mL) slowly at room temperature. The reaction mixture was stirred for overnight and then concentrated under reduced pressure to remove excess oxalyl chloride and THF. The residue obtained was dissolved in 25 ml of toluene, and the slurry was concentrated again to obtain the title product 8 as a solid (0.835 g, 75%).

c. Preparation of 4-amino-1-((6aR,9aR)-9,9-difluoro-2,2,4,4-tetraisopropyltetrahydro-6H-furo[3,2-f][1,3,5,2,4]trioxadisilocin-8-yl)pyrimidin-2(1H)-one

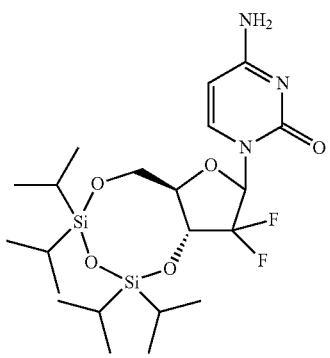 [SMILES: CC(C)[Si]1(C(C)C)OC[C@H]2OC(n3ccc(N)nc3=O)C(F)(F)[C@@H]2O[Si](C(C)C)(C(C)C)O1]

To the solution of gemcitabine (2 g, 7.60 mmol) in dry pyridine (20 mL), 1,3-dichloro-1,1,3,3-tetraisopropyldisloxane (TPDSCl$_2$) (2.91 mL, 9.12 mmol) was added slowly with stirring. The mixture was stirred at room temperature for 48 h. Pyridine was then removed under reduced pressure and the residue was subjected to a silica gel column chromatography, with a gradient of methanol (1-2.5%) in CH$_2$Cl$_2$ to give the title compound as a white foam (3.20 g, 84%). $^1$H NMR (600 MHz, DMSO-d$_6$) δ 7.48 (d, J=7.8 Hz, 1H), 7.42 (br s, 2H, NH$_2$) 6.11 (m, 1H), 5.78 (d, J=7.8 Hz, 1H), 4.26-4.48 (br s, 1H), 4.17 (dd, J=3.6 and 13.2 Hz, 1H), 3.952-4.42 (m, 2H), 0.98-1.10 (m, 28H).

d. Preparation of N-(1-aR,9aR)-9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-yl)benzo[D][1,3]dioxole-5-carboxamide

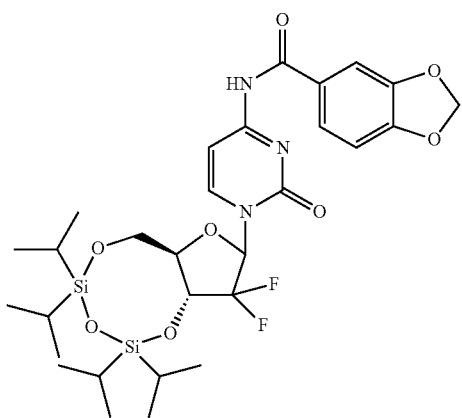 [SMILES: CC(C)[Si]1(C(C)C)OC[C@H]2OC(n3ccc(NC(=O)c4ccc5c(c4)OCO5)nc3=O)C(F)(F)[C@@H]2O[Si](C(C)C)(C(C)C)O1]

To a stirred solution of 4-amino-1-((6aR,9aR)-9,9-difluoro-2,2,4,4-tetraisopropyltetrahydro-6H-furo[3,2-f][1,3,5,2,4]trioxadisilocin-8-yl)pyrimidin-2(1H)-one, prepared as described herein above, (0.2 g, 0.39 mmol) in dry DCM (8 mL) was added pyridine (0.063 mL, 0.79 mmol) and benzo[d][1,3]dioxole-5-carbonyl chloride 8 (0.080 g, 0.43 mmol) under argon atmosphere. The reaction mixture was stirred overnight at room temperature and then solvent was evaporated under reduced pressure. The residue was extracted with DCM (3×10 mL), the organic layer was dried over sodium sulphate and concentrated to provide the title compound as a crude product, which was used in the next synthesis step without purification. $^1$H NMR (600 MHz, DMSO-d6): δ 0.96-1.12 (m, 28H), 3.98-4.10 (m, 2H), 4.23 (dd, J=3 Hz and 12.6 Hz, 1H), 4.35-4.58 (brs, 1H), 6.12 (s, 2H), 6.15-6.25 (brs, 1H), 7.0 (d, J=8.4 Hz, 1H), 7.40 (d, J=5.4 Hz, 1H), 7.55 (d, J=1.2 Hz, 1H), 7.65 (dd, J=8.4 and 1.8 Hz, 1H), 8.0 (s, 1H), 11.24 (s, 1H)

e. Preparation of N-(1-((4R,5R)-3,3-difluoro-4-hydroxy-5-(hydroxymethyl)tetrahydrofuran-2-yl)-2-yl)-1,2-dihydropyrimidin-4-yl)benzo[d][1,3]dioxole-5-carboxamide

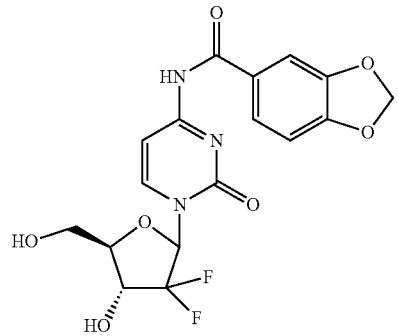 [SMILES: O=C(Nc1ccn(C2O[C@H](CO)[C@@H](O)C2(F)F)c(=O)n1)c1ccc2c(c1)OCO2]

To a stirred solution of compound prepared above, N-(1-((6aR,9aR)-9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-yl)benzo[d][1,3]dioxole-5-carboxamide, (0.150 g, 0.22 mmol) in THF (5 mL) was added 1M TBAF (1.0 mL, 1M in THF). The reaction mixture was stirred at room temperature for 2 h. Solvent was evaporated to dryness and the residue was purified by silica gel column chromatography using 3% methanol in DCM. The compound was further purified by preparative HPLC (gradient of water/acetonitrile). HPLC fractions were lyophilized to afford title compound as a white solid (60 mg). $^1$H NMR (600 MHz, CD$_3$OD): δ 3.80-3.87 (m, 1H), 3.95-4.04 (m, 2H), 4.28-4.29 (m, 1H), 6.09 (s, 2H), 6.28 (t, J=7.2 Hz, 1H), 6.97 (d, J=7.8 Hz, 1H), 7.46 (d, J=1.8 Hz, 1H), 7.61 (dd, J=8.4 and 1.2 Hz, 2H), 8.06 (d, J=7.2 Hz, 1H). $^{13}$C NMR (600 MHz, DMSO-d$_6$) δ 59.0, 68.6 (t, J=22 Hz), 81.2, 84.4 (t, J=30 Hz), 96.9, 102.3, 108.2, 108.5, 123.2, 124.7, 126.9, 144.7, 147.7, 151.4, 154.4, 164.0, 166.4. MS-ESI (m/z) Calcd for C$_{17}$H$_{15}$F$_2$N$_3$O$_7$ [M+Na]$^+$ 434.1. Found 434.0.

f. Preparation of N-(1-6aR,9aR)-9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-yl)-2,3-dihydrobenzo[b][1,4]dioxine-6-carboxamide

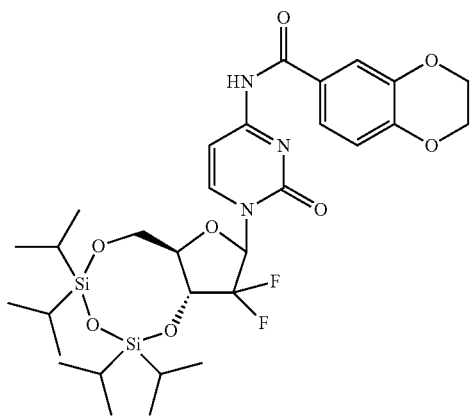 [SMILES: CC(C)[Si]1(C(C)C)OC[C@H]2OC(n3ccc(NC(=O)c4ccc5c(c4)OCCO5)nc3=O)C(F)(F)[C@@H]2O[Si](C(C)C)(C(C)C)O1]

To a stirred solution of 4-amino-1-((6aR,9aR)-9,9-difluoro-2,2,4,4-tetraisopropyltetrahydro-6H-furo[3,2-f][1,3,5,2,4]trioxadisilocin-8-yl)pyrimidin-2(1H)-one, prepared as described herein above, (0.2 g, 0.39 mmol) in dry DCM (8 mL) was added pyridine (0.063 mL, 0.79 mmol) and 2,3-dihydrobenzo[b][1,4]dioxine-6-carbonyl chloride 6 (0.086 g, 0.43 mmol) under argon atmosphere. The reaction mixture was stirred overnight at room temperature and then the solvent was evaporated under reduced pressure. The residue was extracted with DCM (3×10 mL), the organic layer was dried over sodium sulphate and concentrated to provide the title compound as a crude product that was used in the next synthesis step without further purification.

g. Preparation of N-(1-((4R,5R)-3,3-difluoro-4-hydroxy-5-(hydroxymethyl)tetrahydrofuran-2-yl)-2-oxo-1,2-dihydropyrimidin-4-yl)-2,3-dihydrobenzo[b][1,4]dioxine-6-carboxamide

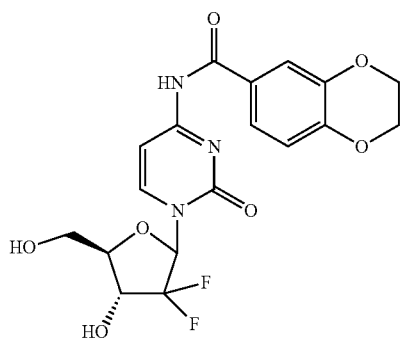 [SMILES: O=C(Nc1ccn(C2O[C@H](CO)[C@@H](O)C2(F)F)c(=O)n1)c1ccc2c(c1)OCCO2]

To a stirred solution of N-(1-((6aR,9aR)-9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-yl)-2,3-dihydrobenzo[b][1,4]dioxine-6-carboxamide, prepared as described herein above, (0.130 g, 0.19 mmol) in THF (4 mL) was added TBAF (1.0 mL, 1 M in THF) and the reaction mixture was stirred at room temperature for 2 h. The solvent was evaporated to dryness and the residue was purified by silica gel column chromatography using 4% methanol in DCM. The compound was further purified by preparative HPLC (gradient of water/Acetonitrile). HPLC fractions were lyophilized to afford the title compound as a white solid (47 mg). $^1$H NMR (600 MHz, DMSO-d6): δ 3.61-3.69 (m, 1H), 3.76-3.84 (m, 1H), 3.86-3.93 (m, 1H), 4.14-4.24 (m, 1H), 4.25-4.35 (m, 4H), 5.33 (t, J=5.4 Hz, 1H), 6.18 (t, J=7.8 Hz, 1H), 6.34 (d, J=5.4 Hz, 1H), 6.95 (d, J=8.4 Hz, 1H), 7.35 (brs, 1H), 7.52-7.62 (m, 2H), 8.26 (d, J=6.0 Hz, 1H), 11.20 (brs, 1H). $^{13}$C NMR (600 MHz, DMSO-d$_6$): δ9.0, 64.2, 64.7, 68.6 (t, J=22.2 Hz), 81.2, 84.4 (t, J=30.7 Hz), 97.0, 117.2, 117.9, 122.6, 123.2 (t, J=257.1 Hz), 126.1, 143.2, 144.6, 147.8, 154.4, 164.0, 166.7. MS-ESI (m/z) Calcd for $C_{18}H_{17}F_2N_3O_7$ [M+Na]$^+$ 448.1. Found 448.1.

h. General Procedures for Synthesis of Substituted Gemcitabine Aryl Amide Analogs

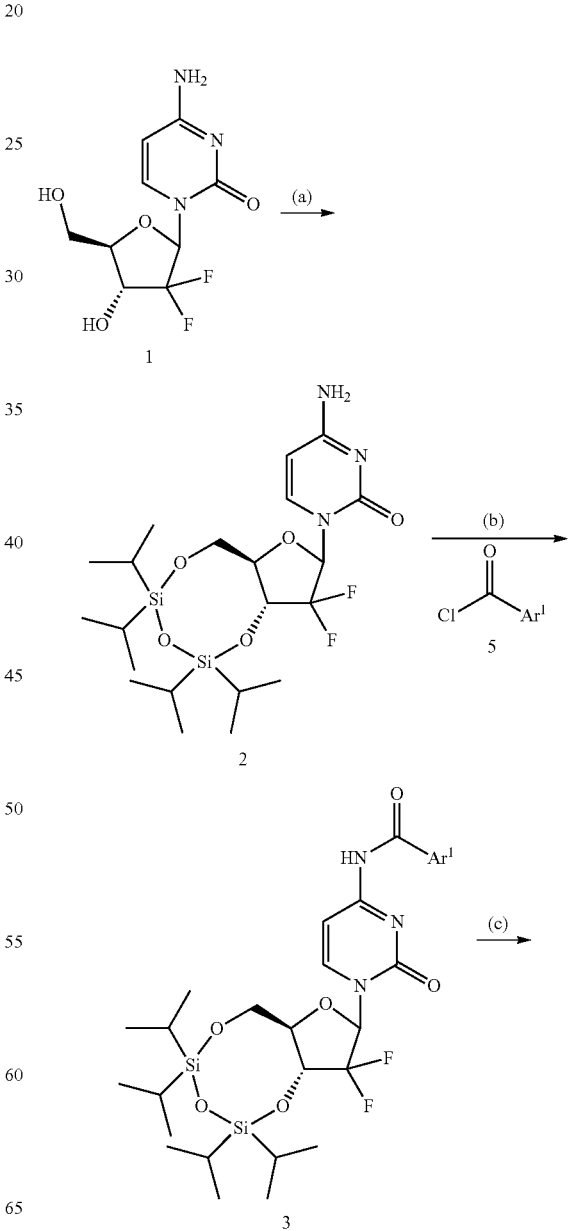

91
-continued

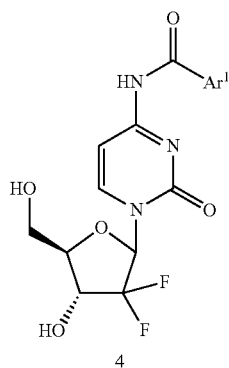

4

Substituted gemcitabine aryl amide analogs of the present invention can be prepared using the synthesis scheme provided immediately above, and using the reaction conditions as described herein above. Briefly, compound 2 is prepared as previously described herein above (see preparation of 4-amino-1-((6aR,9aR)-9,9-difluoro-2,2,4,4-tetraisopropyltetrahydro-6H-furo[3,2-f][1,3,5,2,4]trioxadisilocin-8-yl)pyrimidin-2(1H)-one above). Preparation of compound 3 is accomplished as follows: to a solution of compound 2 (0.054 mmol) in dry DCM (5 mL) is added pyridine (2 eq.), then the acyl chloride derivative of $Ar^1$ (compound 5; 1.5 eq.) is added slowly with stirring. The mixture is stirred at room temperature overnight (about 12-18 h). The solvent is removed and the residue (compound 3) is used to the next reaction without further purification. TBAF (1 M in THF, 0.5 mL) is then added to the crude compound 3 and the resulting solution is stirred at room temperature for about 1.5 h. After the removal of the solvent, the residue is subjected to silica gel column chromatography, with a stepwise gradient of methanol (1-5%) in $CH_2Cl_2$ to give the raw product (compound 4). The raw product can be further purified by semi-preparative HPLC (e.g. a gradient of water/acetonitrile was used to obtain N-(1-((4R,5R)-3,3-difluoro-4-hydroxy-5-(hydroxymethyl)tetrahydrofuran-2-yl)-2-oxo-1,2-dihydropyrimidin-4-yl)benzo[d][1,3]dioxole-5-carboxamide and N-(1-((4R,5R)-3,3-difluoro-4-hydroxy-5-(hydroxymethyl)tetrahydrofuran-2-yl)-2-oxo-1,2-dihydropyrimidin-4-yl)-2,3-dihydrobenzo[b][1,4]dioxine-6-carboxamide, described above). HPLC fractions containing the desired compound 4 can be lyophilized overnight to yield a dried product with expected yield of about 60-80% yield and an expected a purity of >99%.

Using the procedures described herein above, additional representative disclosed compounds of the present invention are shown in Table 1 with the corresponding NMR and MS spectral data.

TABLE 1

| No. | Compound | $^1$H NMR | $^{13}$C NMR | $[M + Na]^+$ |
|---|---|---|---|---|
| 3 | (structure) | $^1$H NMR (400 MHz, DMSO-$d_6$) δ 2.10-2.20 (m, 2H), 3.62-3.71 (m, 1H), 3.78-3.86 (m, 1H), 3.90 (dt, J = 8.4 and 2.8 Hz, 1H), 4.15-4.30 (m, 5H), 5.31 (t, J = 5.2 Hz, 1H), 6.20 (t, J = 7.6 Hz, 1H), 6.32 (d, J = 6.4 Hz, 1H), 7.04 (dd, J = 7.2 and 1.2 Hz, 1H), 7.30-7.42 (m, 1H), 7.62-7.68 (m, 2H), 8.28 (d, J = 7.6 Hz, 1H), 11.23 (s, 1H) | $^{13}$C NMR (100 MHz, DMSO-$d_6$) δ 30.7, 58.7, 68.3 (t, J = 22 Hz), 70.3, 70.4, 81.0, 84.1 (t, J = 32 Hz), 96.7, 121.2, 122.2, 124.1, 127.7, 144.4, 150.2, 154.1, 154.8, 163.6, 166.3 | MS-ESI (m/z) Calcd for $C_{19}H_{19}F_2N_3O_7$ $[M + Na]^+$ 462.1; found 462.1 |
| 4 | (structure) | $^1$H NMR (400 MHz, DMSO-$d_6$) δ 1.56 (m, 6H), 3.14 (s, 2H), 3.63-3.72 (m, 1H), 3.78-3.87 (m, 1H), 3.91 (dt, J = 8.4 and 3.2 Hz, 1H), 4.15-4.29 (m, 1H), 5.33 (t, J = 5.6 Hz, 1H), 6.20 (t, J = 7.2 Hz, 1H), 6.33 (s, 1H), 7.02 (dd, J = 7.2 and 7.6 Hz, 1H), 7.46 (d, J = 7.6 Hz, 1H), 7.51 (dd, J = 7.2 and 1.2 Hz 1H), 7.73 (dd, J = 8.0 and 1.2 Hz, 1H), 8.36 (d, J = 7.6 Hz, 1H), 10.14 (s, 1H) | $^{13}$C NMR (100 MHz, DMSO-$d_6$) δ 27.8, 41.0, 58.7, 68.3 (t, J = 23 Hz), 81.1, 84.2 (t, J = 32 Hz), 90.9, 96.1, 114.1, 121.0, 128.3, 129.5, 130.7, 145.3, 154.0, 156.5, 162.4, 163.6 | MS-ESI (m/z) Calcd for $C_{20}H_{21}F_2N_3O_6$ $[M + Na]^+$ 460.1; found 460.1 |

TABLE 1-continued

| No. | Compound | $^1$H NMR | $^{13}$C NMR | [M + Na]$^+$ |
|---|---|---|---|---|
| 5 | | $^1$H NMR (400 MHz, DMSO-d$_6$) δ 3.23 (t, J = 8.8 Hz, 2H), 3.62-3.72 (m, 1H), 3.78-3.86 (m, 1H), 3.90 (dt, J = 8.0 and 3.2 Hz, 1H), 4.15-4.29 (m, 1H), 4.64 (t, J = 8.8 Hz, 2H), 5.31 (t, J = 5.2 Hz, 1H), 6.20 (t, J = 7.6 Hz, 1H), 6.32 (d, J = 6.4 Hz, 1H), 6.85 (d, J = 8.4 Hz, 1H), 7.38 (d, J = 6.0 Hz, 1H), 7.86 (dd, J = 8.4 and 2.0 Hz, 1H), 7.94 (d, J = 1.2 Hz, 1H), 8.27 (d, J = 7.6 Hz, 1H), 11.13 (s, 1H) | $^{13}$C NMR (100 MHz, DMSO-d$_6$) δ 28.4, 58.8, 68.3 (t, J = 22 Hz), 72.0, 81.0, 84.1 (t, J = 31 Hz), 96.6, 108.6, 126.0, 127.9, 130.0, 144.3, 154.1, 163.7, 166.8 | MS-ESI (m/z) Calcd for C$_{18}$H$_{17}$F$_2$N$_3$O$_6$ [M + Na]$^+$ 432.1; found 432.1 |
| 6 | | $^1$H NMR (400 MHz, DMSO-d$_6$) δ 3.61-3.70 (m, 1H), 3.77-3.85 (m, 1H), 3.90 (dt, J = 8.4 and 2.8 Hz, 1H), 4.13-4.26 (m, 1H), 5.30 (t, J = 5.6 Hz, 1H), 6.11 (s, 2H), 6.17 (t, J = 7.2 Hz, 1H), 6.31 (d, J = 6.4 Hz, 1H), 6.96 (d, J = 8.4 Hz, 1H), 7.12 (d, J = 8.0 Hz, 1H), 7.30 (d, J = 7.6 Hz, 1H), 8.34 (d, J = 7.6 Hz, 1H), 11.59 (s, 1H) | $^{13}$C NMR (100 MHz, DMSO-d$_6$) δ 58.7, 68.3 (t, J = 23 Hz), 81.1, 84.3 (t, J = 31 Hz), 96.0, 102.7, 109.4, 110.8, 119.3, 125.3, 145.4, 146.0, 147.2, 154.0, 162.7, 163.8 | MS-ESI (m/z) Calcd for C$_{17}$H$_{14}$BrF$_2$N$_3$O$_7$ [M + Na]$^+$ 512.0; found 512.0 |
| 7 | | $^1$H NMR (600 MHz, DMSO-d$_6$) δ 3.65-3.70 (m, 1H), 3.80-3.85 (m, 1H), 3.90-3.94 (m, 1H), 4.18-4.26 (m, 1H), 5.33 (t, J = 4.8 Hz, 1H), 6.21 (t, J = 6.0 Hz, 1H), 6.34 (d, J = 6.6 Hz, 1H), 7.39 (d, J = 7.2 Hz, 1H), 7.57 (d, J = 8.4 Hz, 1H), 7.94 (d, J = 7.8 Hz, 1H), 8.05 (s, 1H), 8.34 (d, J = 6.6 Hz, 1H), 11.46 (br s, 1H) | $^{13}$C NMR (600 MHz, DMSO-d$_6$) δ 59.0, 68.6 (t, J = 23 Hz), 81.3, 84.5 (t, J = 32 Hz), 96.8, 100.3, 110.2, 110.7, 123.2, 126.6, 129.8, 131.5, 142.9, 145.9, 154.4, 163.8, 166.0 | MS-ESI (m/z) Calcd for C$_{17}$H$_{13}$F$_4$N$_3$O$_7$ [M + Na]$^+$ 470.1; found 470.0 |

TABLE 1-continued

| No. | Compound | $^1$H NMR | $^{13}$C NMR | [M + Na]$^+$ |
|---|---|---|---|---|
| 8 | 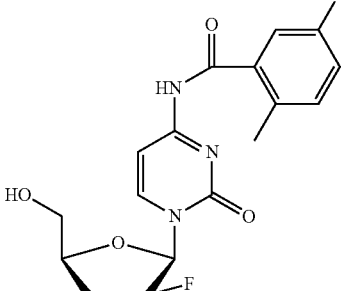 | $^1$H NMR (600 MHz, DMSO-d$_6$) δ 2.35 (s, 3H), 3.61-3.69 (m, 1H), 3.76-3.84 (m, 1H), 3.86-3.93 (m, 1H), 4.14-4.24 (m, 1H), 4.25-4.35 (m, 4H), 5.33 (t, J = 5.4 Hz, 1H), 6.18 (t, J = 7.8 Hz, 1H), 6.34 (d, J = 5.4 Hz, 1H), 6.95 (d, J = 8.4 Hz, 1H), 7.31 (s, 1H), 7.52 (s, 1H), 8.26 (d, J = 6.0 Hz, 1H), 11.12 (br s, 1H) | $^{13}$C NMR (600 MHz, DMSO-d$_6$): 19.3, 59.0, 64.2, 64.6, 68.6 (t, J = 22.2 Hz), 81.2, 84.4 (t, J = 30.4 Hz), 96.7, 118.0, 119.4, 123.2 (t, J = 257.3 Hz), 127.2, 130.8, 140.8, 144.7, 145.6, 154.4, 163.7, 168.8 | MS-ESI (m/z) Calcd for C$_{19}$H$_{19}$F$_2$N$_3$O$_7$ [M + Na]$^+$ 462.1; found 462.1 |
| 9 | 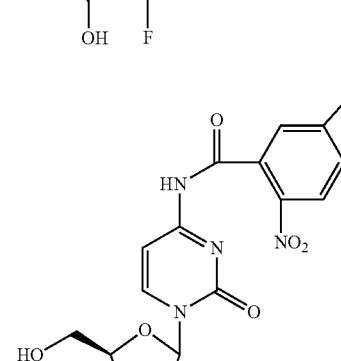 | $^1$H NMR (600 MHz, DMSO-d$_6$) δ 3.65-3.70 (m, 1H), 3.80-3.86 (m, 1H), 3.90-3.94 (m, 1H), 4.18-4.26 (m, 1H), 5.33 (br s, 1H), 6.19 (t, J = 7.2 Hz, 1H), 6.29 (s, 1H), 6.31-6.35 (m, 3H), 7.33 (s, 1H), 7.76 (s, 1H), 8.35 (d, J = 7.2 Hz, 1H), 11.62 (br s, 1H) | $^{13}$C NMR (600 MHz, DMSO-d$_6$): 59.0, 68.6 (t, J = 22.1 Hz), 81.3, 84.5 (t, J = 32.0 Hz), 96.3, 104.3, 104.8, 108.2, 123.2 (t, J = 259.2 Hz), 128.7, 140.5, 145.4, 149.0, 152.4, 154.2, 163.1, 166.6 | MS-ESI (m/z) Calcd for C$_{17}$H$_{14}$F$_2$N$_4$O$_9$ [M + Na]$^+$ 479.1; found 479.1 |

3. Analytical Procedures

The following procedures can be used to determine various aspects of the disclosed compounds and compositions.

a. IC$_{50}$ Assay with HCV Replicon Cell-Line

Plating Cells: The cells used in these assays were a liver-derived Huh7 cell line containing an HCV replicon bearing a luciferase reporter gene. The Huh7 cell-line can be obtained from various sources including the Japanese Collection of Research Bioresources (JCRB), Osaka, Japan. The Huh7 cell line containing an HCV replicon bearing a luciferase reporter gene can be prepared essentially as described by Vrolijk J M, et al. (J Virol Methods. (2003) 110(2):201-9). Cells were passaged when they reached about 70% confluency. These cells were counted by using a hemocytometer and diluted to 1×10$^5$ cells per mL in DMEM+10% FBS+0.25 µg/mL G415. These cells were plated in 100 µL volumes (10,000 cells per well) in a white-walled 96-well plate and allowed to attach for 24 hours at 37° C.

Treating of the cells: The media (DMEM+2% FBS) was pre-warmed to 37° C. The 100 mM stocks of the HPLC purified compounds were diluted to 0.5 mM in DMEM+2% FBS. These 0.5 mM dilutions were then used to further serially dilute the compounds in DMEM+2% FBS+0.5% DMSO to keep the concentration of DMSO in each condition identical. The 96-well plate was then removed from the 37° C. incubator and the media on the plate was replaced with the serial dilutions of the compounds in triplicate. The plate was then returned to 37° C. for 48 h.

Luciferase Assay: Bright-Glo reagent (Promega Corporation, Madison, Wis.) was removed from the −80° C. freezer and thawed at 4° C. in the dark. The amount of reagent necessary for the experiment (3.65 mL) was removed, and the stock container returned to −80° C. The Glo Lysis Buffer and the Bright Glow reagent was allowed to warm to room temperature for about 30 min in the dark. The 96 well plate was removed from the incubator, and the cells were allowed to cool to room temperature for about 30 min. The media was removed from cells, and the cells were gently washed with about 100 µL of phosphate buffered saline (PBS). The PBS was removed, and 50 µL of the Glo Lysis Buffer was added to each well. The plates were gently rocked for about 15 min at room temperature in the dark to ensue complete cell lysis, then about 50 µL of the Bright Glo reagent was added to each well of the 96-well plate, and the reagent was mixed well with the cell lysate. It should be noted that luciferin has a half-life of approximately 30 min at room temperature after it is added to the plate. The plate was then inserted into the plate reader (GloMax 96 Microplate Luminometer used in these assays; Promega Corporation, Madison, Wis.) and allowed to sit for 5 min in the dark for the luciferase reaction to reach a steady state. The luminescence on the plate was read by using the pre-installed "Bright Glo" Promega program. The data was saved and used to calculate the percent inhibition of luciferase activity at each drug concentration. The data were fit to a 4 parameter logistic curve using Kaleidagraph (Synergy Software, Reading, Pa.). Curve equation: (m1−m2)/(1+(x/m3)^m4); m1=100; m2=0.01; m3=0.01; m4=0.01; the equation is:

$$y = \frac{(\text{Top Plateau} - \text{Bottom Plateau})}{\left(1 + \left(\frac{x}{IC_{50}}\right)\right)^{\text{Hill Slope}}}$$

b. Experimental Procedures for TC$_{50}$ Assays with Huh7 Cells

Plating Cells: Huh7 cells (a hepatocellular carcinoma cell-line; these cells can be obtained from the Japanese Collection of Research Bioresources (JCRB), Osaka, Japan) were used to determine the TC$_{50}$ for representative compounds of the present invention. Briefly, Huh7 cells were passaged when they reached about 70% confluency. The cells were counted using a hemocytometer following dilution of the cells to about 0.5×10$^5$ cells per mL in DMEM with 10% fetal bovine serum (FBS). The cells were plated in a clear 96-well plate (about 5,000 cells in 100 μL per well). The cells were allowed to attach for about 24 hours at 37° C.

Treating of the cells: The DMEM media without phenol red containing 2% FBS was pre-warmed to 37° C. Gemcitabine analogs were diluted to 0.5 mM in DMEM without phenol red+2% FBS from 100 mM master stocks. Following dilution, the final DMSO concentration was about 0.5% (v/v). The 0.5 mM dilutions were used for further serial dilutions of the test compound, with dilutions made in DMEM without phenol red+2% FBS+0.5% DMSO, thus maintaining the identical concentration of DMSO at each test compound dilution. The 96-well plate was removed from the 37° C. incubator, and the media on the plate replaced with each test compound dilution in triplicate. The plates were then returned to the incubator and incubated with the cells for 48 h at 37° C.

MTS Assay: The reagents from CellTiter 96 kit (Promega Corporation, Madison, Wis.) were thawed at room temperature in the dark for 1 h. The 96-well plate with cells incubated with test compound was removed from the 37° C. incubator. The appropriate amounts of the MTS and PMS reagents were removed from the kit and mixed well. The reagents were maintained in the dark due to their light sensitivity. At 48 h after drug treatment, 20 μL of the combined MTS/PMS reagent were added to each well of the plate, mixed well and the plate returned to 37° C. The absorbance of each well at 490 nm and 650 nm was then read by using the Flexstation 3 (Molecular Devices, LLC, Sunnyvale, Calif.) in endpoint mode every hour for 3 h. The solutions were mixed completely in the wells prior to each reading. The data were then fit to the Emax model: $y = (E_{max} \cdot x)/(TC_{50}+x)$, where $E_{max}$ is the maximum inhibition and TC$_{50}$ is the half maximal (50%) toxicity concentration.

The IC5$_0$, TC$_{50}$, and therapeutic index values for representative disclosed compounds were determined using the assays described herein above and the results obtained are summarized in Table 2 below, and compared to the compound gemcitabine (indicated as "Gem" in the table). All test compounds were purified by HPLC to provide a purity of >99%.

TABLE 2

| No. | Test Compound-Structure | MW | IC$_{50}$ (nM) | TC$_{50}$ (μM) | Therapeutic Index |
|---|---|---|---|---|---|
| Gem* | 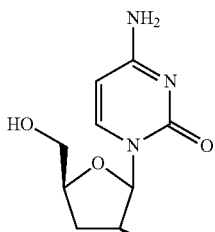 | 263.2 | 58 ± 6 | 35 ± 12 | 597 |
| 1 | 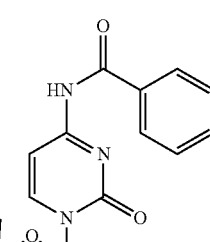 | 411.31 | 60 ± 8 | 473 ± 74 | 7910 |

TABLE 2-continued

| No. | Test Compound-Structure | MW | IC$_{50}$ (nM) | TC$_{50}$ (μM) | Therapeutic Index |
|---|---|---|---|---|---|
| 2 | | 425.34 | 127 ± 9 | 855 ± 166 | 6790 |
| 3 | | 439.11 | 92 ± 8 | 881 ± 287 | 9628 |
| 4 | | 437.14 | 177 ± 45 | 1162 ± 204 | 6565 |
| 5 | | 409.11 | 145 ± 17 | 954 ± 247 | 6579 |

TABLE 2-continued

| No. | Test Compound-Structure | MW | IC$_{50}$ (nM) | TC$_{50}$ (µM) | Therapeutic Index |
|---|---|---|---|---|---|
| 6 | | 489.00 | 340 ± 45 | 2214 ± 821 | 6512 |
| 7 | | 447.07 | 46 ± 27 | 188 ± 50 | 4051 |
| 8 | | 439.12 | 1690 ± 1060 | 626 ± 191 | 370 |
| 9 | | 456.1 | 47 ± 4 | >500 | >10,700 |

*Gemcitabine; used as a control compound.

c. Stability Test of Disclosed Compounds at Different pH Conditions

In order for a prodrug to be orally bioavailable, it is advantageous for it be stable over a wide range of pH values. To assess the pH stability of the bicyclic gemcitabine analogs, stocks of a test compound comprising a disclosed compound were prepared (1 mM in ddH$_2$O). The stocks of test compound were diluted to 200 μM in buffered solutions with pH values of 1.0 to 8.0 and incubated at 40° C. for 4 h (Table 3). The relative amount of intact prodrug was then determined by separating the intact prodrug from any degradation products by using reverse-phase high performance liquid chromatography (HPLC) and subsequently quantifying the relative amount of remaining prodrug by UV spectrophotometry.

TABLE 3

| Test Condition (pH) | Preparation |
|---|---|
| pH 8 | 40 μl test compound stock (1 mM) |
|  | 40 μl 100 mM HEPES buffer pH 8.0 at 40° C. |
|  | 120 μl ddH$_2$O |
| pH 6 | 40 μl test compound stock (1 mM) |
|  | 40 μl 100 mM MES buffer pH 8.0 at 40° C. |
|  | 120 μl ddH$_2$O |
| pH 4 | 40 μl test compound stock (1 mM) |
|  | 40 μl 100 mM Citrate buffer pH 8.0 at 40° C. |
|  | 120 μl ddH$_2$O |
| pH 2 | 40 μl test compound stock (1 mM) |
|  | 40 μl 0.05M HCl |
|  | 120 μl ddH$_2$O |
| pH 1 | 40 μl test compound stock (1 mM) |
|  | 40 μl 0.5M HCl |
|  | 120 μl ddH$_2$O |

HPLC analysis: 100 μl of the incubated solution was loaded onto a Vydac C18 analytical column 4.6/250, and the mobile phase run at 1 mL/min water with the following procedures: a. Inject 100 μl the incubated solution; b. Water for 5 minutes at 1 ml/min; c. 0-100% acetonitrile over 30 minutes; d. Back to 100% water.

Analysis: Standard HPLC analysis software was used to quantitate the area under each peak. Degradation peaks were quantitated as a percentage of the peak of the same amount of control sample (no heat treatment).

Results are presented in Table 4 below. The data show that tested compounds have good stability in a broad pH range, i.e. about 80% or greater of compound remaining intact for 4 h at 40° C. over pH 2-8.

TABLE 4

| | Compound* remaining (%) | |
|---|---|---|
| Condition | 1 | 2 |
| Pretreatment | 100 | 100 |
| pH 1 | 64 | 71 |
| pH 2 | 100 | 100 |
| pH 4 | 100 | 100 |
| pH 6 | 100 | 100 |
| pH 8 | 92 | 100 |

*Compound number refers to the compound number, and corresponding structure, shown in Table 2.

d. TC$_{50}$ Assays—Inhibition of ENT1

Plating Cells: Huh7 cells or PK9 cells were seeded in 96-well plates at a density of 5,000 cells/well or 2,500 cells/well, respectively, and the plates were incubated at 37° C. for 24 h to allow for cell attachment.

Treatment with equilibrative nucleoside transporter 1 (ENT1) Inhibitor: The media was then removed from the plates and replaced with media containing 2% FBS, 0.5% DMSO, and either 10 μM dipyramidole or 10 μM S-(4-nitrobenzyl)-6-thioinosine (NBTI). The cells were then incubated at 37° C. for 1 h to allow for inhibition of the ENT1 inhibitor.

Treating with Control & Compound 1: After incubation with the ENT1 inhibitor, the cells were treated with each compound at final concentrations ranging from 500 μM to 0 μM in triplicate in media containing 2% FBS, 0.5% DMSO, and either 10 μM dipyridamole or 10 μM NBTI. After 48 h of treatment at 37° C., the TC$_{50}$ value of each compound was then determined. Compound 1 refers to the compound number, and corresponding structure, shown in Table 2.

TABLE 5

| | ENT1 Inhibitor | TC$_{50}$ Values (μM) | |
|---|---|---|---|
| Cells | Compound* | Control* | 1* |
| Huh7 cells (48 h) | None | 35 ± 12 | 473 ± 74 |
|  | dipyridamole | >500 | 410 ± 110 |
|  | NBTI | >500 | 440 ± 190 |
| PK9 cells (48 h) | None | 0.095 ± 0.035 | 1.63 ± 0.10 |
|  | dipyridamole | 193 ± 20 | 0.61 ± 0.31 |
|  | NBTI | 1.92 ± 0.78 | 2.92 ± 0.41 |

*Control is gemcitabine; compound 1 refers to the compound number, and corresponding structure, shown in Table 2.

Gemcitabine is known to enter cells principally through Equilibrative Nucleoside Transporter 1 (ENT1). Loss of human ENT1 activity results in gemcitabine resistance (see Kroep, J. R., et al. (20020 Mol. Cancer Ther. 1, 371-376). To determine if the disclosed compounds utilize the ENT1 transporter for cell entry, a cytotoxicity assay was performed in the presence of either dipyridamole or S-(4-nitrobenzyl)-6-thioinosine (NBTI), which are ENT1 inhibitors Representative data obtained using the methods described herein above is shown in Table 5. The TC$_{50}$ values of each compound in the presence or absence of the ENT1 inhibitors were then compared. The disclosed analogs do not require the ENT1 inhibitor for cell entry. Without wishing to be bound by theory, cells that have lost ENT1 activity may therefore be sensitive to compound 1 and other disclosed analogs, whereas these cells are resistant to a compound such as gemcitabine.

e. TC$_{50}$ Assays—Effect of Deficient Deoxycytidine Kinase Activity

Plating Cells: PK9 or RPK9 cells were seeded in 96-well plates at a density of 2,500 cells/well or 2,500 cells/well, respectively, and the plates were incubated at 37° C. for 24 h to allow for cell attachment.

Treating with Control & Compound 1: The cells were treated with each compound at final concentrations ranging from 500 μM to 0 μM in triplicate in media containing 2% FBS and 0.5% DMSO. After 48 h of treatment at 37° C., the TC$_{50}$ value of each compound was then determined. Compound 1 refers to the compound number, and corresponding structure, shown in Table 2.

The RPK9 cells—a gemcitabine-resistant cell-line—are deficient for deoxycitidine kinase (dCK) activity, which is required for the initial phosphorylation of dFdC to dFdCMP. dCK is frequently inactivated in acquired gemcitabine-resistant human cancer cell lines. The RPK9 cells are described in Saiki, T., et al. (2012) *Biochim. Biophys. Res. Commun.* 421, 98-104). Without wishing to be bound by theory, these data suggest that both gemcitabine and 1 are not effective when treating dCK-deficient cancer cells and patients. The cytotoxicity of 1 compared to gemcitabine after 48 h treatment of PK9 and RPK9 cells is shown in Table 6.

TABLE 6

| Compound | TC$_{50}$ ($\mu$M), 48 h treatment | |
|---|---|---|
| | PK9 cells | RPK9 cells |
| Gem* | 0.095 ± 0.035 | >500 |
| 1* | 1.63 ± 0.10 | >500 |

*"Gem" is gemcitabine; compound 1 refers to the compound number, and corresponding structure, shown in Table 2.

f. TC$_{50}$ Assays in Different Human Cell Lines

Plating Cells: Huh7, HEPG2, HEK293, MCF-7, or BxPC3 cells (which can be obtained from American Type Culture Collection, ATCC) were passaged when they were about 70% confluent. The cells were counted by using a hemocytometer and diluted to about 1×10$^4$ cells per mL in DMEM+10% FBS. Cells were plated in 100 µL volumes (1,000 cells per well) in a clear 96-well plate. The cells following passaging were allowed to attach for about 24 hours at 37° C.

Treating of the cells: DMEM media without phenol red+2% FBS media was pre-warmed to 37° C. Stock solutions (100 mM) of test compounds were diluted to 0.5 mM in DMEM without phenol red+2% FBS, which has a DMSO concentration following dilution of the stock solution of 0.5% (v/v). The 0.5 mM dilution of test compound was serially diluted in DMEM without phenol red+2% FBS+0.5% DMSO, thus the concentration of DMSO was constant in all test compound dilutions. The 96-well plate was then removed from the 37° C. incubator, and the media on the plate was replaced with the diluted test compound in DMEM without phenol red+2% FBS+0.5% DMSO. The plates were then returned to the incubator, and cells incubated for about 96 h at 37° C.

MTS Assay: Assay was carried out as described above. The TC$_{50}$ data obtained are illustrated in Table 7.

TABLE 7

| Compound* | Huh7 ($\mu$M) | HEPG2 ($\mu$M) | HEK293 ($\mu$M) | MCF-7 ($\mu$M) | BxPC3 ($\mu$M) |
|---|---|---|---|---|---|
| Gem | 3.41 +/− 1.36 | 0.311 +/− 0.055 | 0.56 +/− 0.13 | 0.067 +/− 0.014 | 0.0029 +/− 0.0003 |
| 1 | 7.04 +/− 1.42 | 2.81 +/− 0.53 | 4.09 +/− 0.73 | 1.19 +/− 0.33 | 0.72 +/− 0.18 |
| 2 | 3.34 +/− 1.01 | 1.13 +/− 0.25 | 5.61 +/− 0.80 | 1.44 +/− 0.40 | 1.15 +/− 0.23 |

*"Gem" is gemcitabine; compound 1 and 2 refer to the compound numbers, and corresponding structures, shown in Table 2.

g. In Vivo Toxicology Assessment

All in vivo toxicology assays were performed with CD-1 ICR mice (female, 4-6 week old; 20-30 gram body weight). Groups of one to five mice were treated at each dose level. In one study, compound 1 was prepared at concentrations ranging from 0.1 mg/mL to 30 mg/mL in dimethyl sulfoxide (DMSO) and 200 µL of each solution was administered via oral gavage to mice at final doses of 0.67, 2.0, 6.7, 20, 67 and 200 mg/kg. All of the evaluated doses were well-tolerated and no toxicity was observed during the 24 hour period of observation. Compound 1 refers to the compound number, and corresponding structure, shown in Table 2.

A second study was carried out using a different vehicle. As above, CD-1 ICR mice (female, 4-6 week old; 20-30 gram body weight) were used. Groups of one to five mice were treated at each dose level. Compound 1 was prepared in Formulation I (5% DMSO/10% Solutol/17% (2-Hydroxypropyl)-β-cyclodextrin in aqueous solution) at concentrations ranging from 0.03 mg/mL to 1.0 mg/mL, and administered orally. Briefly, mice were treated with 200 µL of compound 1 in Formulation I via oral gavage at final doses of 2.4 mg/kg and 8.0 mg/kg. In a parallel study, compound 1 was administered intravenously. Briefly, mice were injected with 100 µL of compound 1 in Formulation I at final doses ranging from 0.12 mg/kg to 4.0 mg/kg. All of the evaluated doses administered either orally or by IV using Formulation I were well-tolerated and no toxicity was observed during the 48 hour observation period.

h. In Vivo Pharmacokinetic Assessment

All pharmacokinetic studies were performed with CD-1 ICR mice (female, 4-6 week old; 20-30 gram body weight), and three mice were used at each dose level and at each time point for each compound tested. Mice were treated orally with either compound 1 at doses of 1.0, 4.0 and 8.0 mg/kg, or gemcitabine at doses of 4.0 and 8.0 mg/kg. For consistency, both compound 1 and gemcitabine were prepared in Formulation I. At 5, 30, 60 and 90 min post treatment, mice were euthanized, and plasma and liver samples were collected. It should be noted that compound 1 refers to the compound number, and corresponding structure, shown in Table 2.

Tetrahydrouridine (THU) was immediately added to plasma samples at a final concentration of 25 µg/mL to prevent deamination of dFdC after collection, and the samples were subsequently flash-frozen and stored at −80° C. until analysis.

Approximately 200-300 mg of each mouse liver was dissected and homogenized in 150 µL of phosphate buffered saline (PBS) containing 25 µg/mL THU, resulting in 2 mg liver/µL saline homogenate. These liver homogenates were also flash-frozen and stored at −80° C. until analysis.

Equivalent amounts of blood plasma and liver tissue were also collected from untreated mice and used to prepare calibration standards and quality controls. An LC-MS/MS assay was utilized to simultaneously quantify the concentrations of compound 1, dFdC and dFdU in each of the plasma and liver samples.

Figure 3:
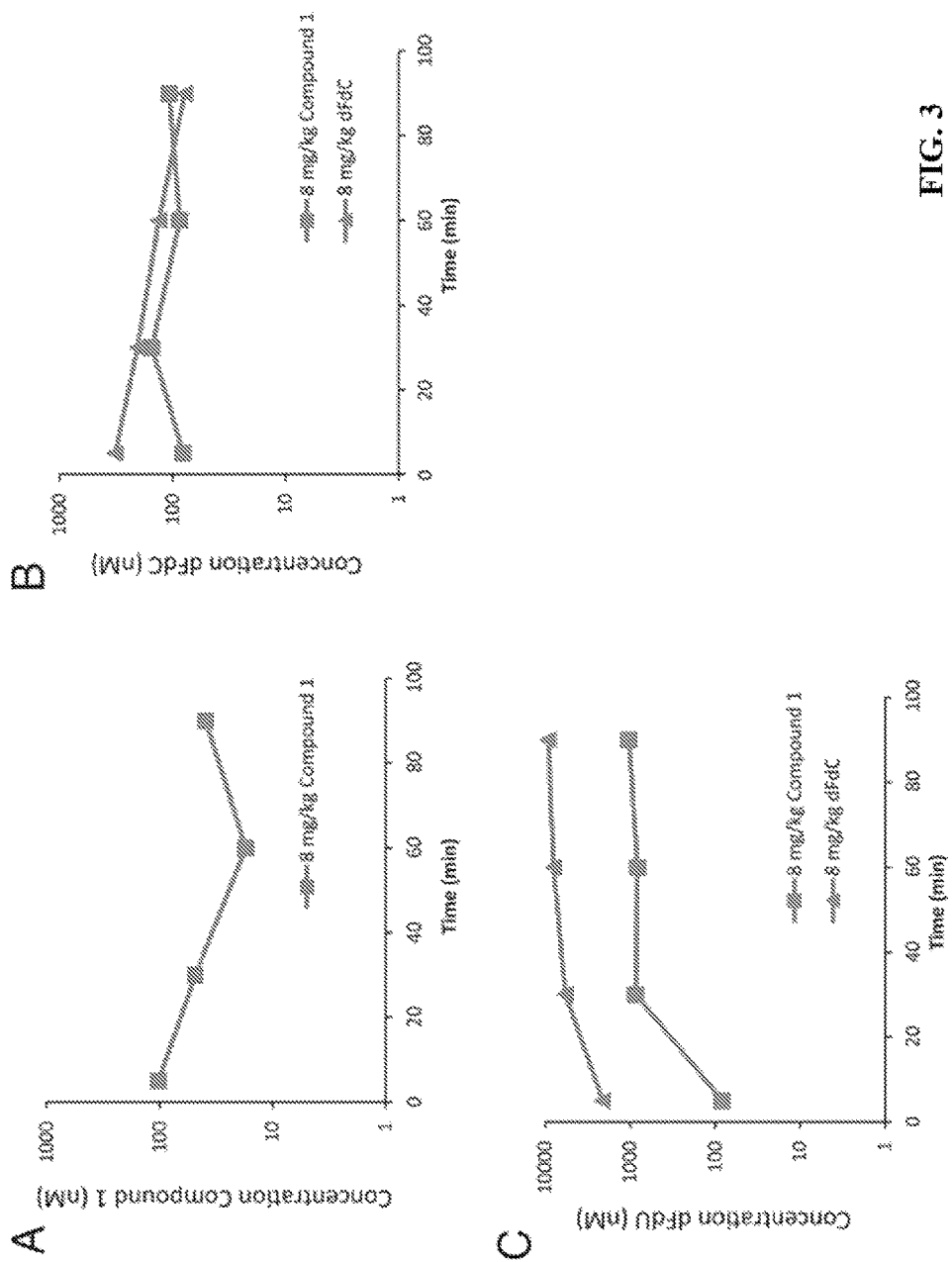
FIG. 3 shows representative in vivo pharmacokinetic data for a representative disclosed compound. Briefly, mice were treated orally with either compound 1 or gemcitabine at doses of 8.0 mg/kg (panels A, B and C), 4.0 mg/kg (panels D, E and F), or 1.0 mg/kg (G, H and I). At 5, 30, 60 and 90 min after treatment, mice were euthanized and plasma and liver samples were collected. The concentration of compound 1 (panels A, D, and G), gemcitabine (panels B, E and H), and dFdU (panels C, F, and I) in each plasma sample was then determined by using an LC/MS/MS assay. Each data point represents the average concentration of each compound or metabolite within the plasma samples collected from three separate mice. Notably, mice were neither treated with 4 mg/kg gemcitabine for 90 min nor treated with 1 mg/kg gemcitabine. In the figure panels, gemcitabine is indicated as "dFdC." Compound 1 refers to the compound number, and corresponding structure, shown in Table 2.
Figure 3:
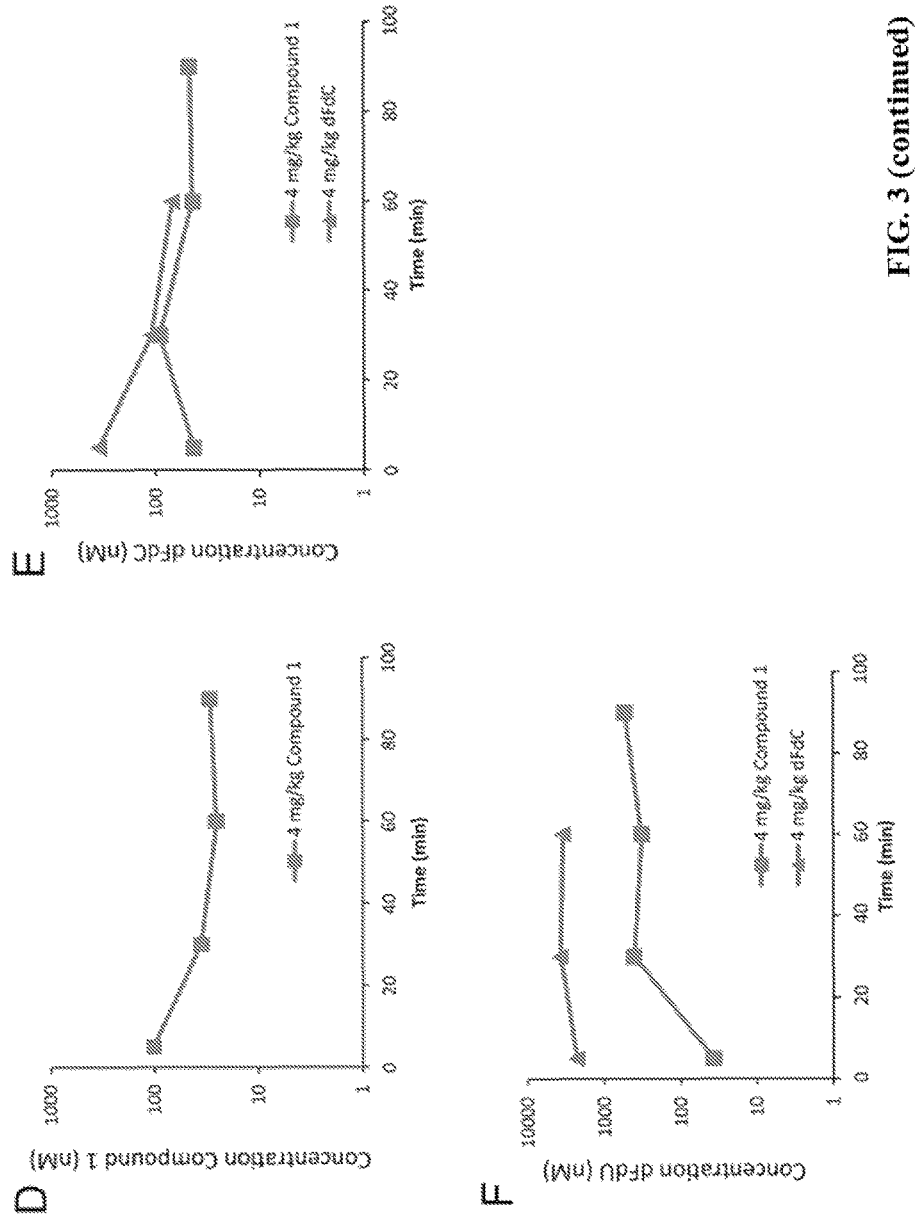
Figure 3:
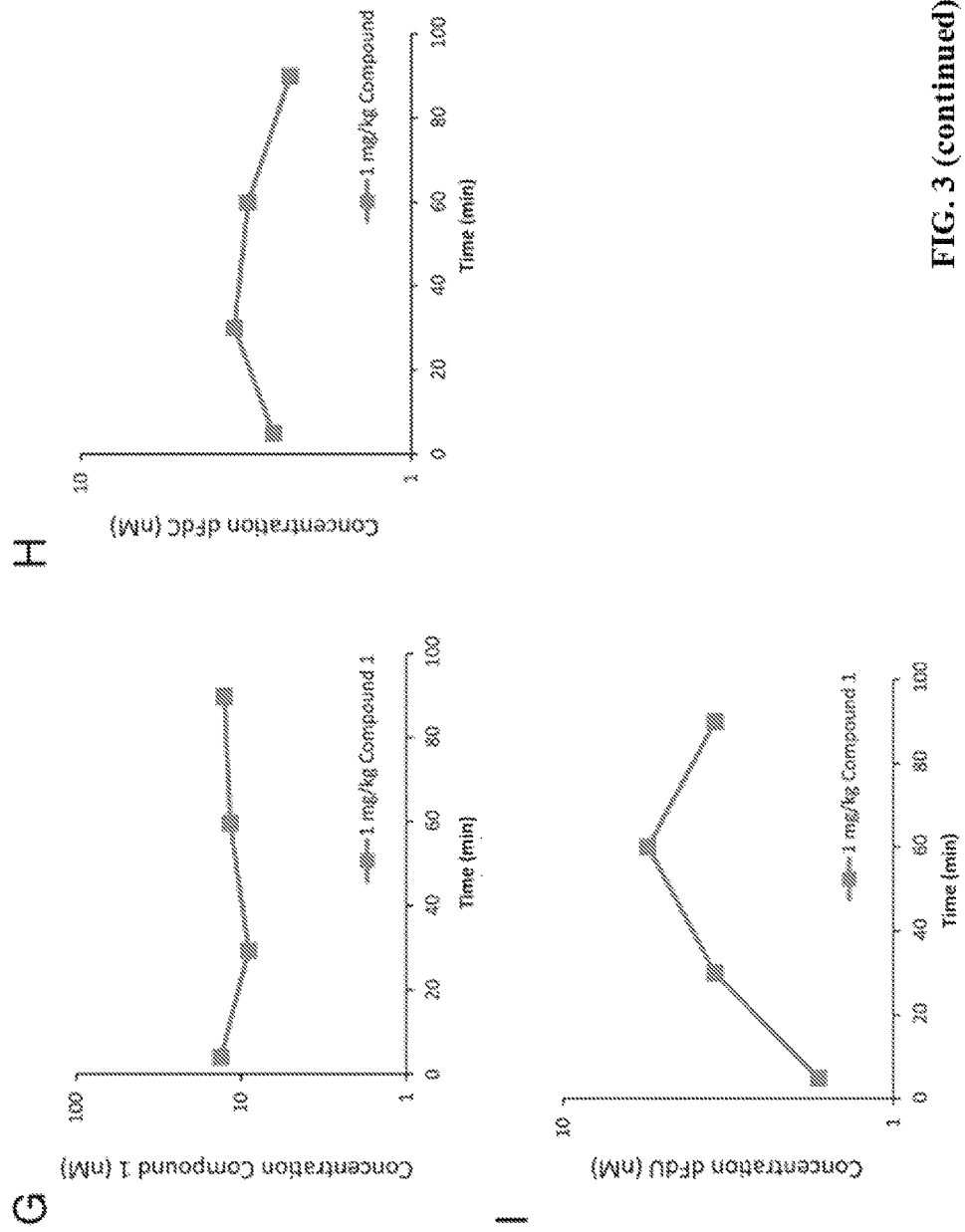
Figure 4:
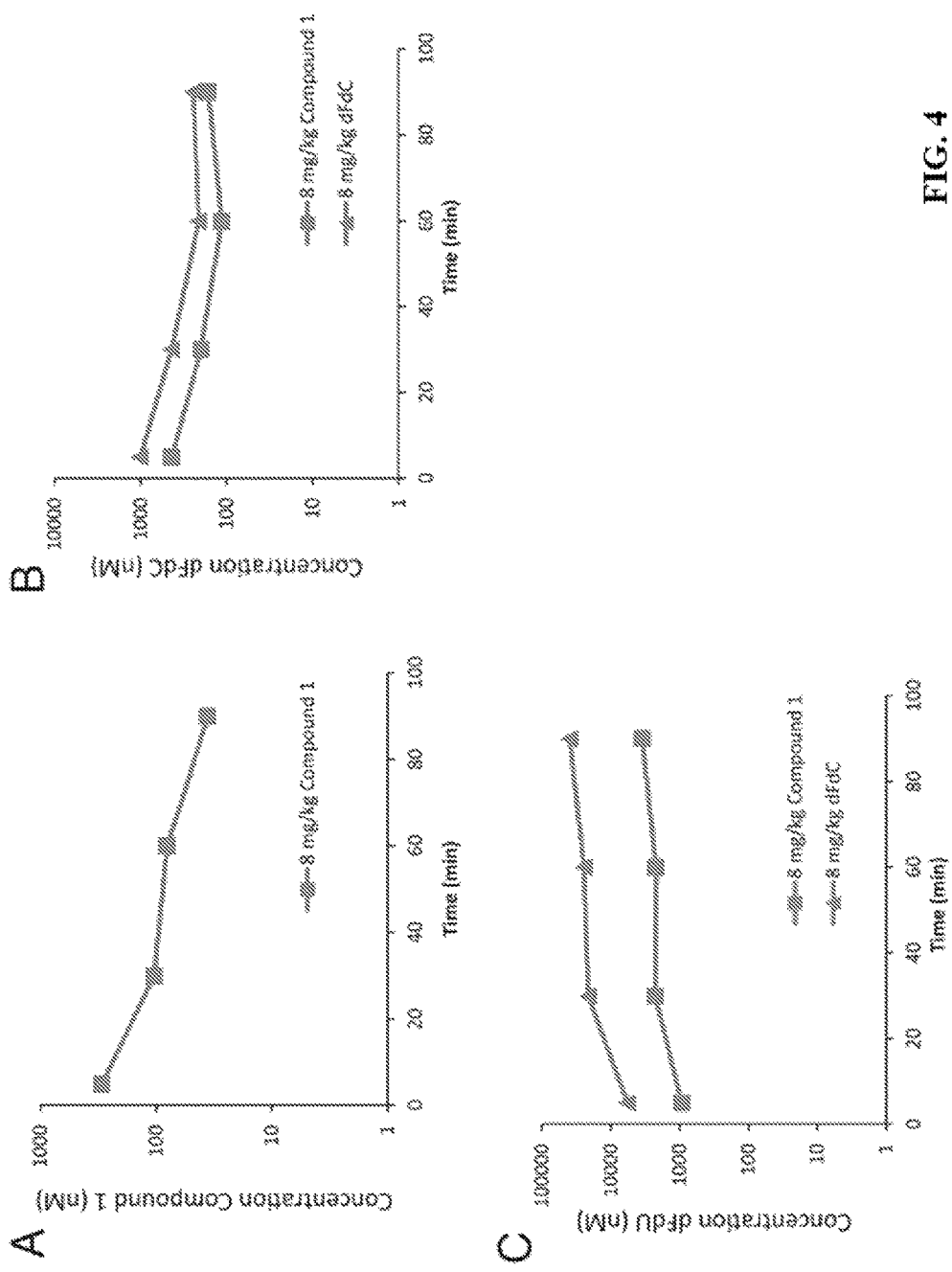
FIG. 4 shows representative in vivo pharmacokinetic data for a representative disclosed compound. Briefly, mice were treated orally with either compound 1 or gemcitabine at doses of 8.0 mg/kg (panels A, B and C), 4.0 mg/kg (panels D, E and F), or 1.0 mg/kg (G, H and I). At 5, 30, 60 and 90 min after treatment, mice were euthanized and plasma and liver samples were collected. The concentration of compound 1 (panels A, D, and G), gemcitabine (panels B, E and H), and dFdU (panels C, F, and I) in each liver sample was then determined by using an LC/MS/MS assay. Each data point represents the average concentration of each compound or metabolite within the liver tissue collected from three separate mice. Notably, mice were neither treated with 4 mg/kg gemcitabine for 90 min nor treated with 1 mg/kg gemcitabine. In the figure panels, gemcitabine is indicated as "dFdC." Compound 1 refers to the compound number, and corresponding structure, shown in Table 2.
Figure 4:
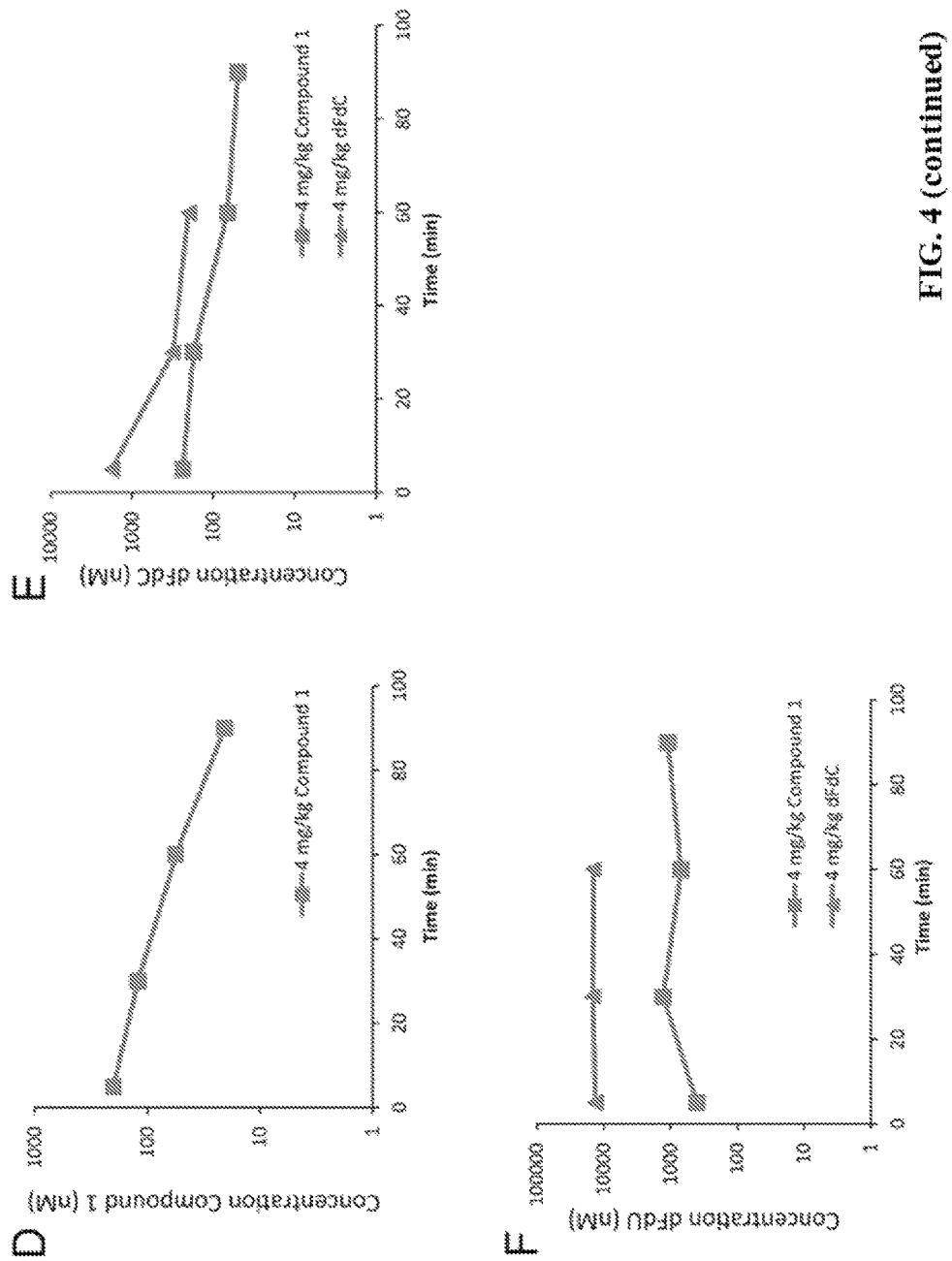
Figure 4:
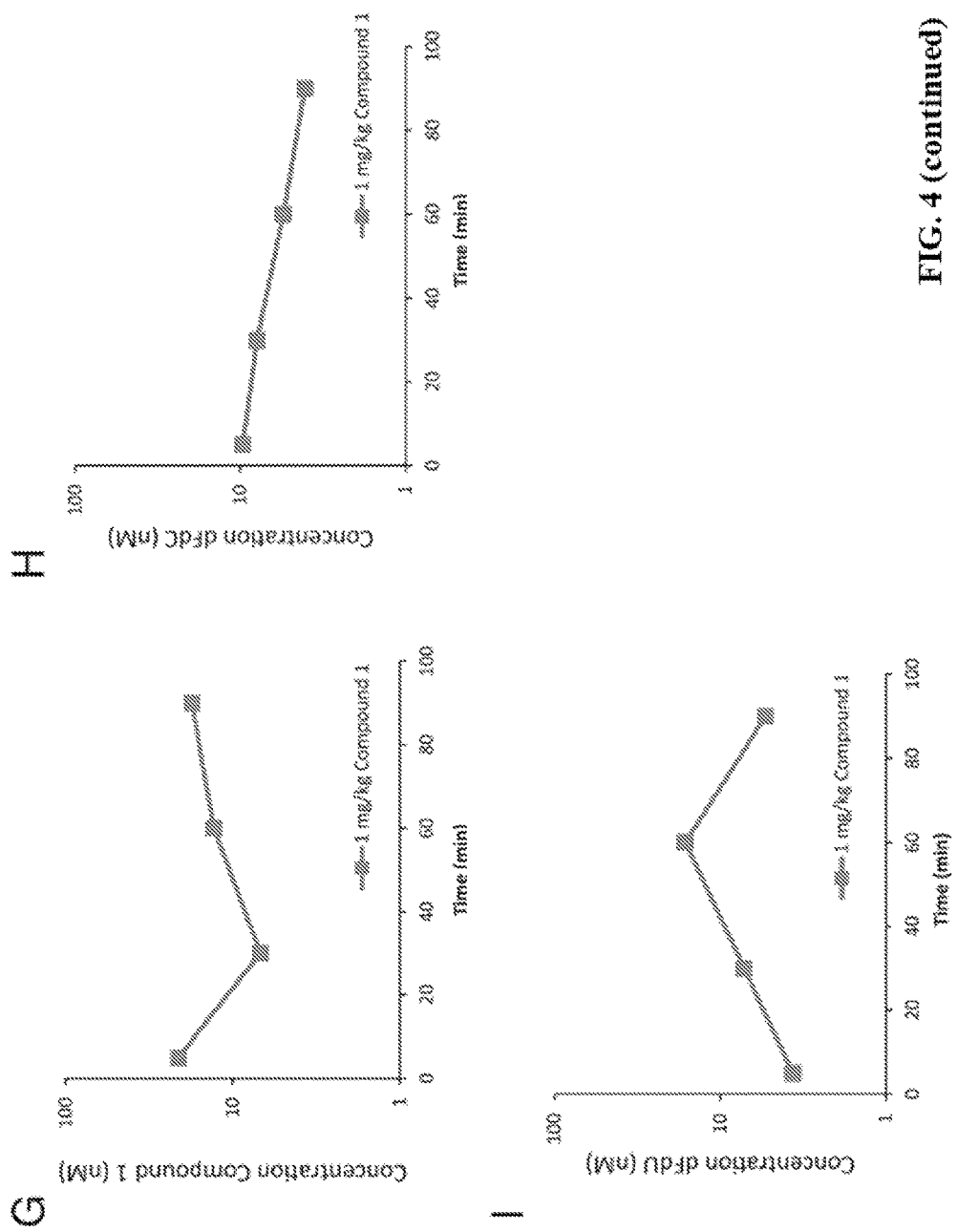

Gemcitabine administered orally exhibited extensive first-pass metabolism and was rapidly converted to the inactive metabolite dFdU, which was observed at relatively high concentrations in both plasma and liver samples (see FIG. 3 and FIG. 4). In contrast, compound 1 produced less of the inactive metabolite dFdU in plasma and liver samples. During the experimental time window (5-90 min), the maximum observed concentration (C$_{max}$) of gemcitabine converted from compound 1 in plasma and liver samples were 152 nM and 473 nM, respectively, after treating mice with 8.0 mg/kg of Compound 1. In contrast, $C_{max}$ values of dFdC in plasma and liver samples from mice treated with 8.0 mg/kg of dFdC were 321 nM and 1007 nM, respectively. Therefore, the maximum detected concentration of gemcitabine in plasma and liver samples after treating mice with 8.0 mg/kg of compound 1 were only 2- to 3-fold lower than the maximum detected concentration of gemcitabine detected after treating mice with a similar dose of gemcitabine.

Overall, this pharmacokinetic analysis demonstrated that when compound 1 was administered orally, it was successfully converted to gemcitabine in the liver and the gemcitabine produced by the hydrolysis of compound 1 was present at a higher concentration in the liver than in plasma. Moreover, without wishing to be bound by a particular theory, compound 1 appears to have reduced first pass metabolism to the inactive metabolite dFdU. The data show that dFdC produced from the hydrolysis of Compound 1 exhibited linear pharmacokinetics in terms of dFdC exposure vs. compound 1 dosage within the investigated dose range. Data for the systemic exposure, calculated as the observed area under the curve ($AUC_{obs}$) for the liver and plasma for both compound 1 and gemcitabine released from compound 1 are shown in Tables 8 and 9, respectively. Pharmacokinetic data are shown in FIGS. 3 and 4 for plasma and liver samples, respectively.

TABLE 8*

| Dose (mg/kg) | Plasma $AUC_{obs}$ (μmol/L*min)** | Liver $AUC_{obs}$ (μmol/L*min)** |
|---|---|---|
| 1.0 | 0.95 | 1.10 |
| 4.0 | 3.45 | 7.84 |
| 8.0 | 3.71 | 9.53 |

*Compound 1 was used in these studies; the number refers to the compound number, and corresponding structure, shown in Table 2.
**$AUC_{obs}$ is for compound 1 in the plasma or liver, as indicated.

TABLE 9*

| Dose (mg/kg) | Plasma $AUC_{obs}$ (μmol/L*min)** | Liver $AUC_{obs}$ (μmol/L*min)** |
|---|---|---|
| 1.0 | 0.26 | 0.56 |
| 4.0 | 5.03 | 10.46 |
| 8.0 | 9.45 | 16.71 |

*Compound 1 was used in these studies; the number refers to the compound number, and corresponding structure, shown in Table 2.
**$AUC_{obs}$ is for dFdC converted from compound 1 in the plasma or liver, as indicated.

i. Prospective Time Course Assay of HCV Luciferase Replicon Inhibition

The disclosed compounds are expected to reach 50% of maximal effect at about 20-30 h after treatment, and maximum effect (80-90% inhibition) at about 30-40 h after treatment.

Plating Cells: Carried out as described above for $IC_{50}$ determination.

Treating the cells: Carried out as generally described above. Cells are then harvested at specific time points. Briefly, cells are harvested by first washing the cells in 100 μL of PBS, followed by lysis in 50 μL of the Glo Lysis Buffer (Promega). The cells are gently rocked for 10 min to allow for cell lysis, mixed by pipetting and transferred to separate microfuge tubes. The samples are flash frozen in liquid nitrogen and stored at −80° C. The plate with remaining cells is returned to the 37° C. incubator. The cells are harvested at desired time points. For example, time points at 3 h, 6 h, 9 h, 12 h, 24 h, 48 h, 72 h, 96 h and 120 h are reasonable for a time course assay of HCV luciferase replicon inhibition.

Luciferase Assay: Carried as described above for $IC_{50}$ determination.

j. Prospective Inhibition of the HCV Luciferase Replicon in the Presence of Carboxylesterase Inhibitors The carboxylesterase inhibitor benzil is expected to decrease the potency (increase the $IC_{50}$ value) of the disclosed compounds about 1- to 3-fold, and the carboxylesterase inhibitor bis-p-nitrophenol phosphate (BNPP) is expected to decrease the potency (increase the $IC_{50}$ value) of the disclosed compounds about 1- to 3-fold.

Plating Cells: Carried as described above.

Treating the cells: DMEM+2% FBS media is pre-warmed to 37° C. Stock solutions (100 mM) of benzyl and bis-p-nitrophenol phosphate (BNPP) are diluted to 100 μM in DMEM+2% FBS. The DMSO concentration is adjusted to 0.5% final. 96-well plates with cells are removed from the 37° C. incubator. The media on the plate is replaced with 50 μL of the diluted carboxylesterase inhibitors, and the plate is returned to 37° C. for 1 h. Dilutions of test compounds are prepared as previously described herein above, but the dilutions contain 100 μM of benzil or BNPP. At the end of the 1 h incubation, the 96-well plate is removed from the 37° C. incubator and the diluted test compound (50 μL)+100 μM of benzil or BNPP is added to the wells. In addition, additional wells of cells are incubated with solutions of test compounds with either benzil or BNPP, or media without any test compound, benzil, or BNPP. Each test condition is carried out on triplicate wells. The plate is then returned to the incubator, and cells incubated at 37° C. for 48 h.

Luciferase Assay: Carried out as described above.

k. Prospective Assessment of Reversal of Anti-HCV Activity by Exogenous Nucleosides The disclosed compounds are expected to be effective in the presence of cytidine, but inhibitory effects are expected to be reversed by a large excess of deoxycytidine.

Plating Cells: The Luciferase replicon cell line is passaged and plated as described above.

Treating the cells: Generally as described above, but that media comprises cytidine or deoxycytidine at concentrations of 50 μM with gemcitabine or a test compound (i.e. a disclosed compound). The concentration of gemcitabine or test compound tested is as follows: 1 μM, 100 nM, 25 nM or 0 nM in DMEM+2% FBS+0.5% DMSO (final).

Luciferase Assay: As described herein above.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

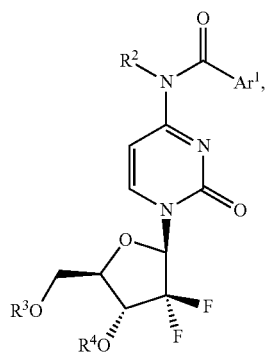

wherein $Ar^1$ is a bicyclic fused ring system having an aryl ring fused to a 5-, 6-, or 7-membered heterocycloalkyl;
wherein the aryl ring is selected from phenyl, pyridinyl, pyrimidinyl, pyridazinyl, pyrazinyl, and triazinyl;
wherein the aryl ring is substituted with 0, 1, 2, or 3 groups independently selected from halogen, —OH, —CN, —NH$_2$, C$_1$-C$_6$ alkyl, C$_1$-C$_6$ alkoxy, C$_1$-C$_6$ monohaloalkyl, C$_1$-C$_6$ polyhaloalkyl, C$_1$-C$_6$ alkylamino, and C$_1$-C$_6$ dialkylamino;
wherein the heterocycloalkyl is substituted with 0, 1, 2, 3, 4, or 5 groups independently selected from halogen, —OH, —CN, —NH$_2$, oxo, C$_1$-C$_6$ alkyl, C$_1$-C$_6$ alkoxy, C$_1$-C$_6$ monohaloalkyl, C$_1$-C$_6$ polyhaloalkyl, C$_1$-C$_6$ alkylamino, C$_1$-C$_6$ dialkylamino, C$_1$-C$_6$ aminoalkyl, C$_1$-C$_6$ hydroxyalkyl, —(C=O)OR$^5$, and —(C=O)NR$^{6a}$R$^{6b}$;
wherein each R$^5$ is independently selected from hydrogen, C$_1$-C$_8$ alkyl, and a hydroxyl protecting group;
wherein each of R$^{6a}$ and R$^{6b}$ is independently selected from hydrogen, C$_1$-C$_4$ alkyl, and an amine protecting group;
wherein R$^2$ is selected from hydrogen, C$_1$-C$_4$ alkyl, and an amine protecting group;
wherein R$^3$ is selected from hydrogen and a hydroxyl protecting group; and
wherein R$^4$ is selected from hydrogen, C$_1$-C$_8$ alkyl, and a hydroxyl protecting group, or wherein R$^3$ and R$^4$ together comprise a divalent moiety having a structure represented by a formula:

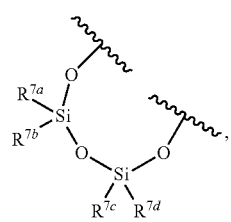

wherein each of R$^{7a}$, R$^{7b}$, R$^{7c}$, and R$^{7d}$ is independently selected from methyl, ethyl, propyl, and butyl;
or a pharmaceutically acceptable salt, or polymorph thereof.

2. The compound of claim 1, wherein $Ar^1$ is a bicyclic fused ring system having a phenyl ring fused to a 5-, 6-, or 7-membered heterocycloalkyl.

3. The compound of claim 1, wherein the heterocycloalkyl is substituted with 0, 1, or 2 groups independently selected from —F, —CN, —NH$_2$, methyl, —CH$_2$F, —CHF$_2$, —CF$_3$, —OCH$_3$, —NHCH$_3$, —N(CH$_3$)$_2$, —CH$_2$OH, —CH$_2$NH$_2$, —(C=O)OH, —(C=O)OCH$_3$, —(C=O)NHCH$_3$, and —(C=O)N(CH$_3$)$_2$.

4. The compound of claim 1, wherein the heterocycloalkyl is unsubstituted.

5. The compound of claim 1, wherein each of R$^2$, R$^3$, and R$^4$ are hydrogen.

6. The compound of claim 1 selected from the group consisting of:

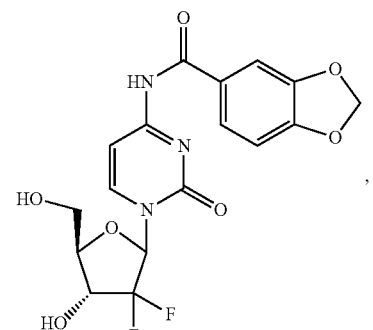

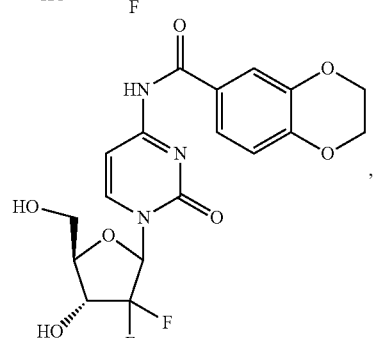

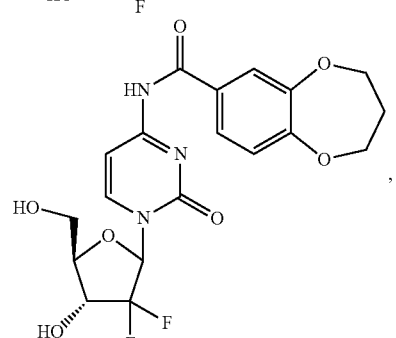

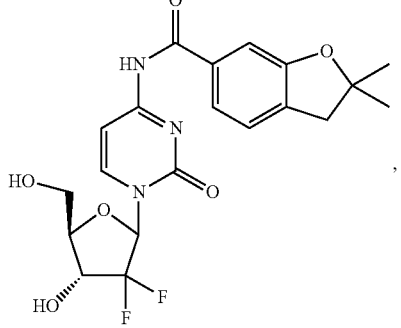

-continued

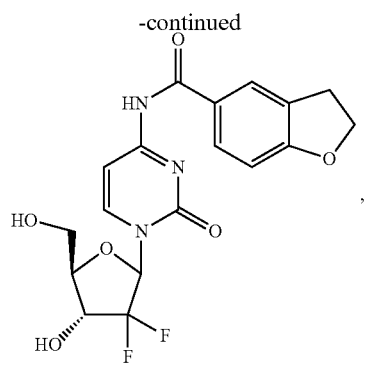

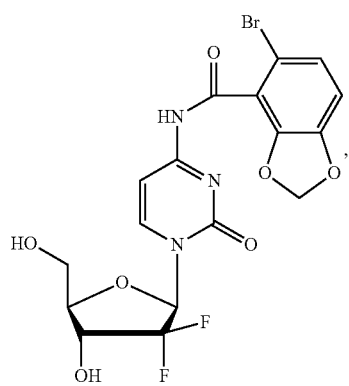

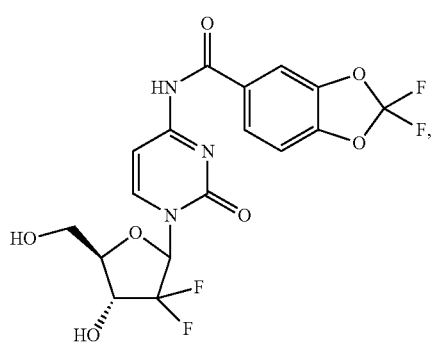

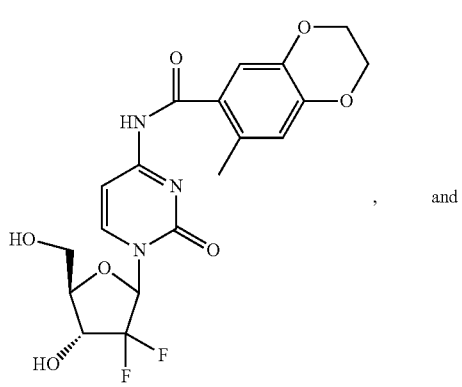
and

-continued

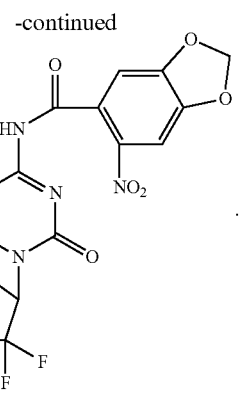

7. A method of making a compound of claim 1, comprising the steps of:
(a) providing a first compound having a structure represented by a formula:

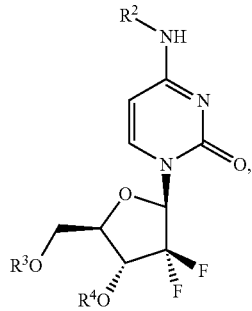

wherein $R^2$ is an amine protecting group;
wherein $R^3$ is a hydroxyl protecting group; and
wherein $R^4$ is a hydroxyl protecting group, or wherein $R^3$ and $R^4$ together comprise a hydroxyl protecting group; and
(b) reacting with a second compound having a structure represented by a formula:

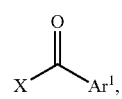

wherein X is halogen or pseudohalogen;
wherein $Ar^1$ is a bicyclic fused ring system having an aryl ring fused to a 5-, 6-, or 7-membered heterocycloalkyl;
wherein the aryl ring is selected from phenyl, pyridinyl, pyrimidinyl, pyridazinyl, pyrazinyl, and triazinyl;
wherein the aryl ring is substituted with 0, 1, 2, or 3 groups independently selected from halogen, —OH, —CN, —NH$_2$, $C_1$-$C_6$ alkyl, $C_1$-$C_6$ alkoxy, $C_1$-$C_6$ monohaloalkyl, $C_1$-$C_6$ polyhaloalkyl, $C_1$-$C_6$ alkylamino, and $C_1$-$C_6$ dialkylamino;
wherein the heterocycloalkyl is substituted with 0, 1, 2, 3, 4, or 5 groups independently selected from halogen, —OH, —CN, —NH$_2$, oxo, $C_1$-$C_6$ alkyl, $C_1$-$C_6$ alkoxy, $C_1$-$C_6$ monohaloalkyl, $C_1$-$C_6$ polyhaloalkyl, $C_1$-$C_6$ alkylamino, $C_1$-$C_6$ dialkylamino, $C_1$-$C_6$ aminoalkyl, $C_1$-$C_6$ hydroxyalkyl, —(C=O)OR$^5$, and —(C=O)NR$^{6a}$R$^{6b}$;

wherein each $R^5$ is independently selected from hydrogen, $C_1$-$C_8$ alkyl, and a hydroxyl protecting group;

wherein each of $R^{6a}$ and $R^{6b}$ is independently selected from hydrogen, $C_1$-$C_4$ alkyl, and an amine protecting group;

thereby forming an amide bond.

8. The method of claim 7, wherein providing the first compound further comprises converting a compound having the structure:

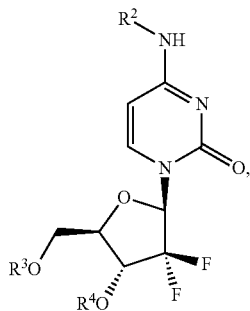

wherein $R^2$ is hydrogen, to the first compound wherein $R^2$ is an amine protecting group.

9. The method of claim 7, wherein providing the first compound further comprises converting a compound having the structure:

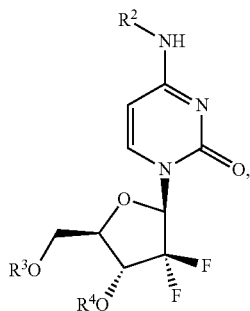

wherein $R^3$ is hydrogen, to the first compound wherein $R^3$ is a hydroxyl protecting group.

10. The method of claim 7, wherein providing the first compound further comprises converting a compound having the structure:

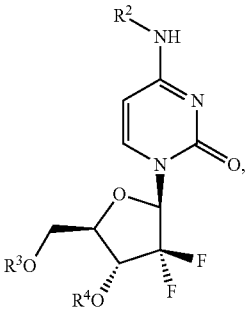

wherein $R^4$ is hydrogen, to the first compound wherein $R^4$ is a hydroxyl protecting group.

11. The method of claim 7, wherein $R^3$ and $R^4$ together are a divalent moiety having a structure represented by a formula:

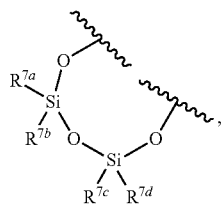

wherein each of $R^{7a}$, $R^{7b}$, $R^{7c}$, and $R^{7d}$ is independently selected from methyl, ethyl, propyl, and butyl.

12. The method of claim 7, further comprising deprotecting $R^2$.

13. The method of claim 7, further comprising deprotecting $R^3$.

14. The method of claim 7, further comprising deprotecting $R^4$.

15. A method for treating a subject for a viral infection comprising a hepatitis C virus, comprising administering to a subject in need thereof an effective amount of the compound of claim 6.

16. The method of claim 15, wherein the compound is:

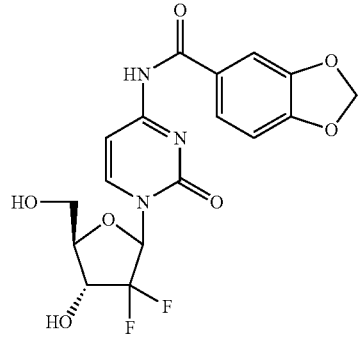

* * * * *